(12) United States Patent
Hirotsuka et al.

(10) Patent No.: US 9,314,234 B2
(45) Date of Patent: Apr. 19, 2016

(54) PRE-TIED SURGICAL KNOTS FOR USE WITH SUTURE PASSERS

(71) Applicant: Ceterix Orthopaedics, Inc., Menlo Park, CA (US)

(72) Inventors: Mark Y. Hirotsuka, San Jose, CA (US); Michael Murillo, Menlo Park, CA (US); Yoav Ben-Haim, San Francisco, CA (US); Justin D. Saliman, Los Angeles, CA (US); Christopher P. Bender, Oakland, CA (US); Michael J. Hendricksen, Redwood City, CA (US)

(73) Assignee: Ceterix Orthopaedics, Inc., Menlo Park, CA (US)

( * ) Notice: Subject to any disclaimer, the term of this patent is extended or adjusted under 35 U.S.C. 154(b) by 194 days.

(21) Appl. No.: 13/758,994

(22) Filed: Feb. 4, 2013

(65) Prior Publication Data

US 2014/0074157 A1 Mar. 13, 2014

Related U.S. Application Data

(60) Provisional application No. 61/698,528, filed on Sep. 7, 2012.

(51) Int. Cl.
*A61B 17/04* (2006.01)
*A61B 17/06* (2006.01)

(52) U.S. Cl.
CPC ............. *A61B 17/04* (2013.01); *A61B 17/0401* (2013.01); *A61B 17/0469* (2013.01);
(Continued)

(58) Field of Classification Search
CPC ............... A61B 17/04; A61B 17/0401; A61B 17/0469; A61B 17/0482; A61B 17/06; A61B 17/12; A61B 17/00; A61B 17/062

USPC ............. 606/228, 139, 144–148; 289/1.2, 1.5
See application file for complete search history.

(56) References Cited

U.S. PATENT DOCUMENTS

| 1,037,864 A | 9/1912 | Carlson et al. |
| 2,738,790 A | 3/1956 | Todt, Sr. et al. |

(Continued)

FOREIGN PATENT DOCUMENTS

| CN | 201263696 Y | 7/2009 |
| CN | 101961256 A | 2/2011 |

(Continued)

OTHER PUBLICATIONS

Saliman; U.S. Appl. No. 14/292,695 entitled "Suture methods for forming locking loops stitches," filed May 30, 2014.

(Continued)

*Primary Examiner* — Eric Rosen
*Assistant Examiner* — George J Ulsh
(74) *Attorney, Agent, or Firm* — Shay Glenn LLP

(57) ABSTRACT

Sutures with pre-tied knots for use in percutaneous surgical procedures. Described herein are pre-tied sutures and methods of using them that may be used with a suture passer for percutaneously suturing tissue, including percutaneously passing and securing a loop of suture around a tear in a meniscus tissue of the knee. A suture with a pre-tied knot may include a length of suture and a knot body on the length of suture, and a leader snare tied to the length of suture by the knot body. The leader snare typically has an opening loop (bight or snare) through which an end of the suture may be passed. The tail of the leader snare may be pulled to remove the leader snare for the knot body and draw the end of the suture through the knot body to close the knot, which can then be tightened to secure the tissue.

17 Claims, 46 Drawing Sheets

(52) U.S. Cl.
CPC ......... *A61B17/0482* (2013.01); *A61B 17/0483* (2013.01); *A61B 2017/0474* (2013.01); *A61B 2017/0477* (2013.01); *A61B 2017/0496* (2013.01); *A61B 2017/06042* (2013.01)

(56) References Cited

U.S. PATENT DOCUMENTS

| | | | |
|---|---|---|---|
| 2,748,773 | A | 6/1956 | Vacheresse, Jr. |
| 3,470,875 | A | 10/1969 | Johnson |
| 3,580,256 | A | 5/1971 | Wilkinson et al. |
| 3,807,407 | A | 4/1974 | Schweizer |
| 3,842,840 | A | 10/1974 | Schweizer |
| 3,901,244 | A | 8/1975 | Schweizer |
| 4,021,896 | A | 5/1977 | Stierlein |
| 4,109,658 | A | 8/1978 | Hughes |
| 4,164,225 | A | 8/1979 | Johnson et al. |
| 4,236,470 | A | 12/1980 | Stenson |
| 4,345,601 | A | 8/1982 | Fukuda |
| 4,440,171 | A | 4/1984 | Nomoto et al. |
| 4,553,543 | A | 11/1985 | Amarasinghe |
| 4,605,002 | A | 8/1986 | Rebuffat |
| 4,706,666 | A | 11/1987 | Sheets |
| 4,836,205 | A | 6/1989 | Barrett |
| 4,957,498 | A | 9/1990 | Caspari et al. |
| 4,981,149 | A | 1/1991 | Yoon et al. |
| 5,002,561 | A | 3/1991 | Fisher |
| 5,011,491 | A | 4/1991 | Boenko et al. |
| 5,037,433 | A | 8/1991 | Wilk et al. |
| 5,059,201 | A | 10/1991 | Asnis |
| 5,112,344 | A | 5/1992 | Petros |
| 5,129,912 | A | 7/1992 | Noda et al. |
| 5,156,608 | A | 10/1992 | Troidl et al. |
| 5,193,473 | A | 3/1993 | Asao et al. |
| 5,219,358 | A | 6/1993 | Bendel et al. |
| 5,222,962 | A | 6/1993 | Burkhart |
| 5,250,053 | A | 10/1993 | Snyder |
| 5,250,055 | A | 10/1993 | Moore et al. |
| 5,281,237 | A | 1/1994 | Gimpelson |
| 5,312,422 | A | 5/1994 | Trott |
| 5,330,488 | A | 7/1994 | Goldrath |
| 5,336,229 | A | 8/1994 | Noda |
| 5,342,389 | A | 8/1994 | Haber et al. |
| 5,364,410 | A | 11/1994 | Failla et al. |
| 5,368,601 | A | 11/1994 | Sauer et al. |
| 5,389,103 | A | 2/1995 | Melzer et al. |
| 5,391,174 | A | 2/1995 | Weston |
| 5,397,325 | A | 3/1995 | Della Badia et al. |
| 5,403,328 | A | 4/1995 | Shallman |
| 5,405,352 | A * | 4/1995 | Weston ........................ 606/148 |
| 5,405,532 | A | 4/1995 | Loew et al. |
| 5,431,666 | A | 7/1995 | Sauer et al. |
| 5,437,681 | A | 8/1995 | Meade et al. |
| 5,454,823 | A | 10/1995 | Richardson et al. |
| 5,454,834 | A | 10/1995 | Boebel et al. |
| 5,468,251 | A | 11/1995 | Buelna |
| 5,474,057 | A | 12/1995 | Makower et al. |
| 5,478,344 | A | 12/1995 | Stone et al. |
| 5,478,345 | A | 12/1995 | Stone et al. |
| 5,480,406 | A | 1/1996 | Nolan et al. |
| 5,496,335 | A | 3/1996 | Thomason et al. |
| 5,499,991 | A | 3/1996 | Garman et al. |
| 5,507,757 | A | 4/1996 | Sauer et al. |
| 5,520,702 | A | 5/1996 | Sauer et al. |
| 5,540,704 | A | 7/1996 | Gordon et al. |
| 5,540,705 | A | 7/1996 | Meade et al. |
| 5,562,686 | A | 10/1996 | Sauer et al. |
| 5,569,301 | A | 10/1996 | Granger et al. |
| 5,571,090 | A | 11/1996 | Sherts |
| 5,571,119 | A | 11/1996 | Atala |
| 5,575,800 | A | 11/1996 | Gordon |
| 5,578,044 | A | 11/1996 | Gordon et al. |
| 5,601,576 | A | 2/1997 | Garrison |
| 5,607,435 | A | 3/1997 | Sachdeva et al. |
| 5,616,131 | A | 4/1997 | Sauer et al. |
| 5,618,290 | A | 4/1997 | Toy et al. |
| 5,626,588 | A | 5/1997 | Sauer et al. |
| 5,632,751 | A | 5/1997 | Piraka |
| 5,643,289 | A | 7/1997 | Sauer et al. |
| 5,645,552 | A | 7/1997 | Sherts |
| 5,653,716 | A | 8/1997 | Malo et al. |
| 5,665,096 | A | 9/1997 | Yoon |
| 5,669,917 | A | 9/1997 | Sauer et al. |
| 5,674,229 | A | 10/1997 | Tovey et al. |
| 5,674,230 | A | 10/1997 | Tovey et al. |
| 5,681,331 | A | 10/1997 | de la Torre et al. |
| 5,690,652 | A | 11/1997 | Wurster et al. |
| 5,713,910 | A | 2/1998 | Gordon et al. |
| 5,728,107 | A | 3/1998 | Zlock et al. |
| 5,728,113 | A | 3/1998 | Sherts |
| 5,730,747 | A | 3/1998 | Ek et al. |
| 5,741,278 | A | 4/1998 | Stevens |
| 5,749,879 | A | 5/1998 | Middleman et al. |
| 5,755,728 | A | 5/1998 | Maki |
| 5,759,188 | A | 6/1998 | Yoon |
| 5,766,183 | A | 6/1998 | Sauer |
| 5,792,153 | A | 8/1998 | Swain et al. |
| 5,800,445 | A | 9/1998 | Ratcliff et al. |
| 5,814,054 | A | 9/1998 | Kortenbach et al. |
| 5,824,009 | A | 10/1998 | Fukuda et al. |
| 5,827,300 | A | 10/1998 | Fleega |
| 5,843,126 | A | 12/1998 | Jameel |
| 5,865,836 | A | 2/1999 | Miller |
| 5,871,490 | A | 2/1999 | Schulze et al. |
| 5,876,411 | A | 3/1999 | Kontos |
| 5,876,412 | A | 3/1999 | Piraka |
| 5,895,393 | A | 4/1999 | Pagedas |
| 5,895,395 | A | 4/1999 | Yeung |
| 5,897,563 | A | 4/1999 | Yoon et al. |
| 5,899,911 | A | 5/1999 | Carter |
| 5,906,630 | A | 5/1999 | Anderhub et al. |
| 5,908,428 | A | 6/1999 | Scirica et al. |
| 5,910,148 | A | 6/1999 | Reimels et al. |
| 5,935,138 | A | 8/1999 | McJames, II et al. |
| 5,938,668 | A | 8/1999 | Scirica et al. |
| 5,944,739 | A | 8/1999 | Zlock et al. |
| 5,947,982 | A | 9/1999 | Duran |
| 5,980,538 | A | 11/1999 | Fuchs et al. |
| 5,993,466 | A | 11/1999 | Yoon |
| 6,042,601 | A | 3/2000 | Smith |
| 6,048,351 | A | 4/2000 | Gordon et al. |
| 6,051,006 | A | 4/2000 | Shluzas et al. |
| 6,053,933 | A | 4/2000 | Balazs et al. |
| 6,056,771 | A | 5/2000 | Proto |
| 6,071,289 | A | 6/2000 | Stefanchik et al. |
| 6,077,276 | A | 6/2000 | Kontos |
| 6,099,550 | A | 8/2000 | Yoon |
| 6,113,610 | A | 9/2000 | Poncet |
| 6,126,666 | A | 10/2000 | Trapp et al. |
| 6,129,741 | A | 10/2000 | Wurster et al. |
| 6,139,556 | A | 10/2000 | Kontos |
| 6,152,934 | A | 11/2000 | Harper et al. |
| 6,159,224 | A | 12/2000 | Yoon |
| 6,190,396 | B1 | 2/2001 | Whitin et al. |
| 6,221,085 | B1 | 4/2001 | Djurovic |
| 6,238,414 | B1 | 5/2001 | Griffiths |
| 6,264,694 | B1 | 7/2001 | Weiler |
| 6,277,132 | B1 | 8/2001 | Brhel |
| 6,322,570 | B1 | 11/2001 | Matsutani et al. |
| 6,325,808 | B1 | 12/2001 | Bernard et al. |
| 6,355,050 | B1 | 3/2002 | Andreas et al. |
| 6,368,334 | B1 | 4/2002 | Sauer |
| 6,443,963 | B1 * | 9/2002 | Baldwin et al. ................ 606/148 |
| 6,511,487 | B1 | 1/2003 | Oren et al. |
| 6,533,795 | B1 | 3/2003 | Tran et al. |
| 6,533,796 | B1 | 3/2003 | Sauer et al. |
| 6,551,330 | B1 | 4/2003 | Bain et al. |
| 6,585,744 | B1 | 7/2003 | Griffith |
| 6,626,917 | B1 | 9/2003 | Craig |
| 6,626,929 | B1 | 9/2003 | Bannerman |
| 6,638,283 | B2 | 10/2003 | Thal |
| 6,638,286 | B1 | 10/2003 | Burbank et al. |
| 6,641,592 | B1 | 11/2003 | Sauer et al. |
| 6,719,765 | B2 | 4/2004 | Bonutti |
| 6,723,107 | B1 | 4/2004 | Skiba et al. |

(56) References Cited

U.S. PATENT DOCUMENTS

| | | | |
|---|---|---|---|
| 6,770,084 B1 | 8/2004 | Bain et al. |
| 6,896,686 B2 | 5/2005 | Weber |
| 6,921,408 B2 | 7/2005 | Sauer |
| 6,923,806 B2 | 8/2005 | Hooven et al. |
| 6,923,819 B2 | 8/2005 | Meade et al. |
| 6,936,054 B2 | 8/2005 | Chu |
| 6,984,237 B2 | 1/2006 | Hatch et al. |
| 6,991,635 B2 | 1/2006 | Takamoto et al. |
| 6,997,931 B2 | 2/2006 | Sauer et al. |
| 6,997,932 B2 | 2/2006 | Dreyfuss et al. |
| 7,004,951 B2 | 2/2006 | Gibbens, III |
| 7,029,480 B2 | 4/2006 | Klein et al. |
| 7,029,481 B1 | 4/2006 | Burdulis, Jr. et al. |
| 7,041,111 B2 | 5/2006 | Chu |
| 7,063,710 B2 | 6/2006 | Takamoto et al. |
| 7,087,060 B2 | 8/2006 | Clark |
| 7,112,208 B2 | 9/2006 | Morris et al. |
| 7,118,583 B2 | 10/2006 | O'Quinn et al. |
| 7,131,978 B2 | 11/2006 | Sancoff et al. |
| 7,166,116 B2 | 1/2007 | Lizardi et al. |
| 7,175,636 B2 | 2/2007 | Yamamoto et al. |
| 7,211,093 B2 | 5/2007 | Sauer et al. |
| 7,232,448 B2 | 6/2007 | Battles et al. |
| 7,235,086 B2 | 6/2007 | Sauer et al. |
| 7,311,715 B2 | 12/2007 | Sauer et al. |
| 7,344,545 B2 | 3/2008 | Takemoto et al. |
| 7,390,328 B2 | 6/2008 | Modesitt |
| 7,481,817 B2 | 1/2009 | Sauer |
| 7,491,212 B2 | 2/2009 | Sikora et al. |
| 7,588,583 B2 | 9/2009 | Hamilton et al. |
| 7,594,922 B1 | 9/2009 | Goble et al. |
| 7,632,284 B2 | 12/2009 | Martinek et al. |
| 7,674,276 B2 | 3/2010 | Stone et al. |
| 7,722,630 B1 | 5/2010 | Stone et al. |
| 7,731,727 B2 | 6/2010 | Sauer |
| 7,736,372 B2 | 6/2010 | Reydel et al. |
| 7,749,236 B2 | 7/2010 | Oberlaender et al. |
| 7,842,050 B2 | 11/2010 | Diduch et al. |
| 7,879,046 B2 | 2/2011 | Weinert et al. |
| 7,883,519 B2 | 2/2011 | Oren et al. |
| 7,951,147 B2 | 5/2011 | Privitera et al. |
| 7,951,159 B2 | 5/2011 | Stokes et al. |
| 7,959,650 B2 | 6/2011 | Kaiser et al. |
| 7,972,344 B2 | 7/2011 | Murray et al. |
| 8,394,112 B2 | 3/2013 | Nason |
| 8,398,673 B2 | 3/2013 | Hinchliffe et al. |
| 8,449,533 B2 | 5/2013 | Saliman et al. |
| 2003/0023250 A1 | 1/2003 | Watschke et al. |
| 2003/0065336 A1 | 4/2003 | Xiao |
| 2003/0065337 A1 | 4/2003 | Topper et al. |
| 2003/0078599 A1 | 4/2003 | O'Quinn et al. |
| 2003/0181926 A1 | 9/2003 | Dana et al. |
| 2003/0204194 A1 | 10/2003 | Bittar |
| 2003/0216755 A1 | 11/2003 | Shikhman et al. |
| 2003/0233106 A1 | 12/2003 | Dreyfuss |
| 2004/0249392 A1 | 12/2004 | Mikkaichi et al. |
| 2004/0249394 A1 | 12/2004 | Morris et al. |
| 2004/0267304 A1 | 12/2004 | Zannis et al. |
| 2005/0033319 A1 | 2/2005 | Gambale et al. |
| 2005/0033365 A1 | 2/2005 | Courage |
| 2005/0080434 A1 | 4/2005 | Chung et al. |
| 2005/0090837 A1 | 4/2005 | Sixto, Jr. et al. |
| 2005/0090840 A1 | 4/2005 | Gerbino et al. |
| 2005/0154403 A1 | 7/2005 | Sauer et al. |
| 2005/0228406 A1 | 10/2005 | Bose |
| 2005/0288690 A1 | 12/2005 | Bourque et al. |
| 2006/0020272 A1 | 1/2006 | Gildenberg |
| 2006/0047289 A1 | 3/2006 | Fogel |
| 2006/0084974 A1 | 4/2006 | Privitera et al. |
| 2006/0282098 A1 | 12/2006 | Shelton et al. |
| 2007/0032799 A1 | 2/2007 | Pantages et al. |
| 2007/0219571 A1 | 9/2007 | Balbierz et al. |
| 2007/0250118 A1 | 10/2007 | Masini |
| 2007/0260260 A1 | 11/2007 | Hahn et al. |
| 2007/0260278 A1 | 11/2007 | Wheeler et al. |
| 2008/0086147 A1 | 4/2008 | Knapp |
| 2008/0091219 A1 | 4/2008 | Marshall et al. |
| 2008/0097489 A1 | 4/2008 | Goldfarb et al. |
| 2008/0140091 A1 | 6/2008 | DeDeyne et al. |
| 2008/0228204 A1 | 9/2008 | Hamilton et al. |
| 2008/0234725 A1 | 9/2008 | Griffiths et al. |
| 2008/0243147 A1 | 10/2008 | Hamilton et al. |
| 2008/0269783 A1 | 10/2008 | Griffith |
| 2008/0294256 A1 | 11/2008 | Hagan et al. |
| 2009/0012538 A1 | 1/2009 | Saliman |
| 2009/0018554 A1 | 1/2009 | Thorne et al. |
| 2009/0062816 A1 | 3/2009 | Weber |
| 2009/0062819 A1 | 3/2009 | Burkhart et al. |
| 2009/0105751 A1 | 4/2009 | Zentgraf |
| 2009/0131956 A1 | 5/2009 | Dewey et al. |
| 2009/0209998 A1 | 8/2009 | Widmann |
| 2009/0216268 A1 | 8/2009 | Panter |
| 2009/0228041 A1 | 9/2009 | Domingo |
| 2009/0259233 A1 | 10/2009 | Bogart et al. |
| 2009/0281619 A1 | 11/2009 | Le et al. |
| 2009/0306684 A1 | 12/2009 | Stone et al. |
| 2009/0306776 A1 | 12/2009 | Murray |
| 2010/0057109 A1 | 3/2010 | Clerc et al. |
| 2010/0106169 A1 | 4/2010 | Niese et al. |
| 2010/0114137 A1 | 5/2010 | Vidal et al. |
| 2010/0121352 A1 | 5/2010 | Murray et al. |
| 2010/0130990 A1 | 5/2010 | Saliman |
| 2010/0145364 A1 | 6/2010 | Keren et al. |
| 2010/0185232 A1 | 7/2010 | Hughett et al. |
| 2010/0198235 A1 | 8/2010 | Pierce et al. |
| 2010/0217286 A1 | 8/2010 | Gerber et al. |
| 2010/0228271 A1 | 9/2010 | Marshall et al. |
| 2010/0241142 A1 | 9/2010 | Akyuz et al. |
| 2010/0249809 A1 | 9/2010 | Singhatat et al. |
| 2010/0280530 A1 | 11/2010 | Hashiba |
| 2010/0305581 A1 | 12/2010 | Hart |
| 2010/0305583 A1 | 12/2010 | Baird et al. |
| 2010/0331863 A2 | 12/2010 | Saliman |
| 2011/0022063 A1 | 1/2011 | McClurg et al. |
| 2011/0028998 A1 | 2/2011 | Adams et al. |
| 2011/0060350 A1 | 3/2011 | Powers et al. |
| 2011/0087246 A1 | 4/2011 | Saliman et al. |
| 2011/0100173 A1 | 5/2011 | Stone et al. |
| 2011/0112555 A1 | 5/2011 | Overes et al. |
| 2011/0112556 A1 | 5/2011 | Saliman |
| 2011/0118760 A1 | 5/2011 | Gregoire et al. |
| 2011/0130773 A1 | 6/2011 | Saliman et al. |
| 2011/0152892 A1 | 6/2011 | Saliman et al. |
| 2011/0190815 A1 | 8/2011 | Saliman |
| 2011/0218557 A1 | 9/2011 | Saliman |
| 2011/0251626 A1 | 10/2011 | Wyman et al. |
| 2011/0270280 A1 | 11/2011 | Saliman |
| 2012/0179254 A1 | 7/2012 | Saliman |
| 2012/0239062 A1 | 9/2012 | Saliman et al. |
| 2012/0283750 A1 | 11/2012 | Saliman et al. |
| 2012/0283753 A1 | 11/2012 | Saliman et al. |
| 2012/0283754 A1 | 11/2012 | Murillo et al. |
| 2012/0303046 A1 | 11/2012 | Stone et al. |
| 2013/0072948 A1 | 3/2013 | States, III et al. |
| 2013/0238040 A1 | 9/2013 | Saliman et al. |
| 2013/0253647 A1 | 9/2013 | Saliman et al. |
| 2014/0188136 A1 | 7/2014 | Cournoyer et al. |
| 2015/0142022 A1 | 5/2015 | George et al. |
| 2015/0297215 A1 | 10/2015 | Hendricksen et al. |

FOREIGN PATENT DOCUMENTS

| | | |
|---|---|---|
| EP | 0647431 A2 | 4/1995 |
| JP | 3032847 U | 3/1991 |
| JP | 2009138029 A | 6/2009 |
| JP | 2009538190 | 11/2009 |
| SU | 376089 A | 4/1973 |
| SU | 7288848 A1 | 4/1980 |
| SU | 1725847 A1 | 4/1992 |
| WO | WO 92/05828 A1 | 4/1992 |
| WO | WO 95/13021 A1 | 5/1995 |
| WO | WO 98/31288 A1 | 7/1998 |
| WO | WO 99/34744 A1 | 7/1999 |
| WO | WO 99/42036 A1 | 8/1999 |

(56) References Cited

FOREIGN PATENT DOCUMENTS

| WO | WO 99/47050 A2 | 9/1999 |
| WO | WO 01/56478 A1 | 8/2001 |
| WO | WO 02/07607 A1 | 1/2002 |
| WO | WO 02/096296 A1 | 12/2002 |
| WO | WO 03/077771 A1 | 9/2003 |
| WO | WO 2006/001040 A1 | 1/2006 |
| WO | WO 2006/040562 A1 | 4/2006 |
| WO | WO 2010/141695 A1 | 12/2010 |
| WO | WO 2011/057245 A2 | 5/2011 |

OTHER PUBLICATIONS

Nord et al.; Posterior lateral meniscal root tears and meniscal repair; Orthopedics Today; 5 pgs; Nov. 2010; retrieved from the internet on Aug. 21, 2014 (http://www.healio.com/orthopedics/arthroscopy/news/print/orthopedics-today/%7B1b52a700-e986-4524-ac7d-6043c9799e15%7D/posterior-lateral-meniscal-root-tears-and-meniscal-repair).

Duerig, T. et al., "An overview of nitinol medical applications" Materials Science and Engineering A273-275, May 1999.

Murillo et al.; U.S. Appl. No. 13/893,154 entitled "Suture passer devices and methods," filed May 13, 2013.

Saliman et al.; U.S. Appl. No. 14/451,293 entitled "Transosteal anchoring methods for tissue repair," filed Aug. 4, 2014.

George et al.; U.S. Appl. No. 14/494,561 entitled "Arthroscopic knot pusher and suture cutter," filed Sep. 23, 2014.

Murillo et al.; U.S. Appl. No. 14/572,485 entitled "Automatically reloading suture passer devices and methods," filed Dec. 16, 2014.

Saliman et al.; U.S. Appl. No. 14/546,942 entitled "Suture passer and method for hip labrum repair," filed Nov. 18, 2014.

Asik et al.; Strength of different meniscus suturing techniques; Knee Sur, Sports Traumotol, Arthroscopy; vol. 5; No. 2; pp. 80-83; (year of publication is sufficiently earlier than the effective U.S. filing date and any foreign priority date) 1997.

Asik et al; Failure strength of repair devices versus meniscus suturing techniques; Knee Surg, Sports Traumatol, Arthrosc; vol. 10; No. 1; pp. 25-29; Jan. 2002.

Arthrex®, Arthrex, Inc., "The Next Generation in Shoulder Repair Technology," Product Brochure from Arthrex, Inc; Naples, Florida, (year of pub. sufficiently earlier than effective US filing date and any foreign priority date) 2007, 22 pages.

ArthroCare® Sportsmedicine, Sunnyvale, CA, SmartStitch® Suture Passing System with the PerfectPasserTM, Product brochure, (year of pub. sufficiently earlier than effective US filing date and any foreign priority date) 2006, 4 pages.

BiPass(TM) Suture Punch, Biomet® Sports Medicine, Inc., accessed Feb. 29, 2008 at <http://www.arthrotek.com/prodpage.cfm?c=0A05&p=090706> 2 pages.

Boenisch et al.; Pull-out strength and stiffness of meniscal repair using absorbable arrows or Ti-Cron vertical and horizontal loop sutures; Amer. J. of Sports Med.; vol. 27; No. 5 pp. 626-631; Sep.-Oct. 1999.

Cayenne Medical; CrossFix® II System (product webpage); 4 pgs.; downloaded Nov. 21, 2011 (www.cayennemedical.com/products/crossfix/).

Covidien Surgical; Endo Stitch 10 mm Suturing Device; accessed Dec. 4, 2012 at <http://www.autosuture.com/autosuture/pagebuilder.aspx?topicID=7407&breadcrumbs=0:63659,30691:0,309:0> 2pages.

Depuy Mitek, Inc; Raynham, MA, "Versalok Surgical Technique for Rotator Cuff Repair: The next generation in rotator cuff repair," Product brochure, (year of pub. sufficiently earlier than effective US filing date and any foreign priority date) 2007, 18 pages.

Linvatec Conmed Company, Largo, Florida, Product descriptions B17-19, B21; Tissue Repair Systems, Tissue Repair Accessories, and Master Arthroscopy Shoulder Instrument Set, (printed on or before Aug. 2007), 4 pages.

Ma et al; "Biomechanical Evaluation of Arthroscopic Rotator Cuff Stitches," J Bone Joint Surg Am, Jun. 2004; vol. 86(6):1211-1216.

Medsfera; Suturing devices; accessed Dec. 4, 2012 at <http://www.medsfera.ru/shiv.html> 13 pages.

Nho et al; "Biomechanical fixation in Arthroscopic Rotator Cuff Repair," Arthroscopy: J of Arthroscop and Related Surg; vol. 23. No. 1, Jan. 2007: pp. 94-102.

Rimmer et al.; Failure Strength of Different Meniscal Suturing Techniques; Arthroscopy: The Journal of Arthroscopic and Related Surgery; vol. 11; No. 2; pp. 146-150; Apr. 1995.

Schneeberger, et al; "Mechanical Strength of Arthroscopic Rotator Cuff Repair Techniques: An in Vitro Study," J Bone Joint Surg Am., Dec. 2002; 84:2152-2160.

Smith&Nephew; Fast-Fix Meniscal Repair System (product webpage); 4 pgs.; downloaded Nov. 21, 2011 (http://endo.smith-nephew.com/fr/node.asp?NodeId=3562).

Strobel; Manual of Arthroscopic Surgery (1st Edition); Springer Verlag, Hiedelberg © 2002; pp. 127-129; Dec. 15, 2001.

USS SportsMedicine ArthoSewTM Single Use Automated Suturing Device with 8.6 mm ArthroPort Cannula Set, Instructions for Use, <http:www.uss-sportsmed.com/imageServer.aspx?contentID=5020&contenttype=application/pdf> accessed Apr. 25, 2007, 2 pages.

USS SportsMedicine ArthroSewTM Suturing Device, <http://www.uss-sportsmed.com/SportsMedicine/pageBuilder.aspx?webPageID=0&topicID=7141&xsl=xsl/productPagePrint.xsl>, product description, accessed Apr. 25, 2007, 3 pages.

McCutcheon et al.; U.S. Appl. No. 13/759,000 entitled "Methods And Devices For Preventing Tissue Bridging While Suturing," filed Feb. 4, 2013.

Saliman, J.; U.S. Appl. No. 13/759,006 entitled "Suture Passers," filed Feb. 4, 2013.

Hendricksen et al.; U.S. Appl. No. 13/844,252 entitled "Suture passers and methods of passing suture," filed Mar. 15, 2013.

Hendricksen et al.; U.S. Appl. No. 14/265,848 entitled "Suture passer with radiused upper jaw," filed Apr. 30, 2014.

Hendricksen et al.; U.S. Appl. No. 14/659,471 entitled "Suture passer with radiused upper jaw," filed Mar. 16, 2015.

Hendricksen et al.; U.S. Appl. No. 14/697,494 entitled "Suture passers adapted for use in constrained regions," filed Apr. 27, 2015.

* cited by examiner

USE SUTURE CUTTER TO CUT TAILS

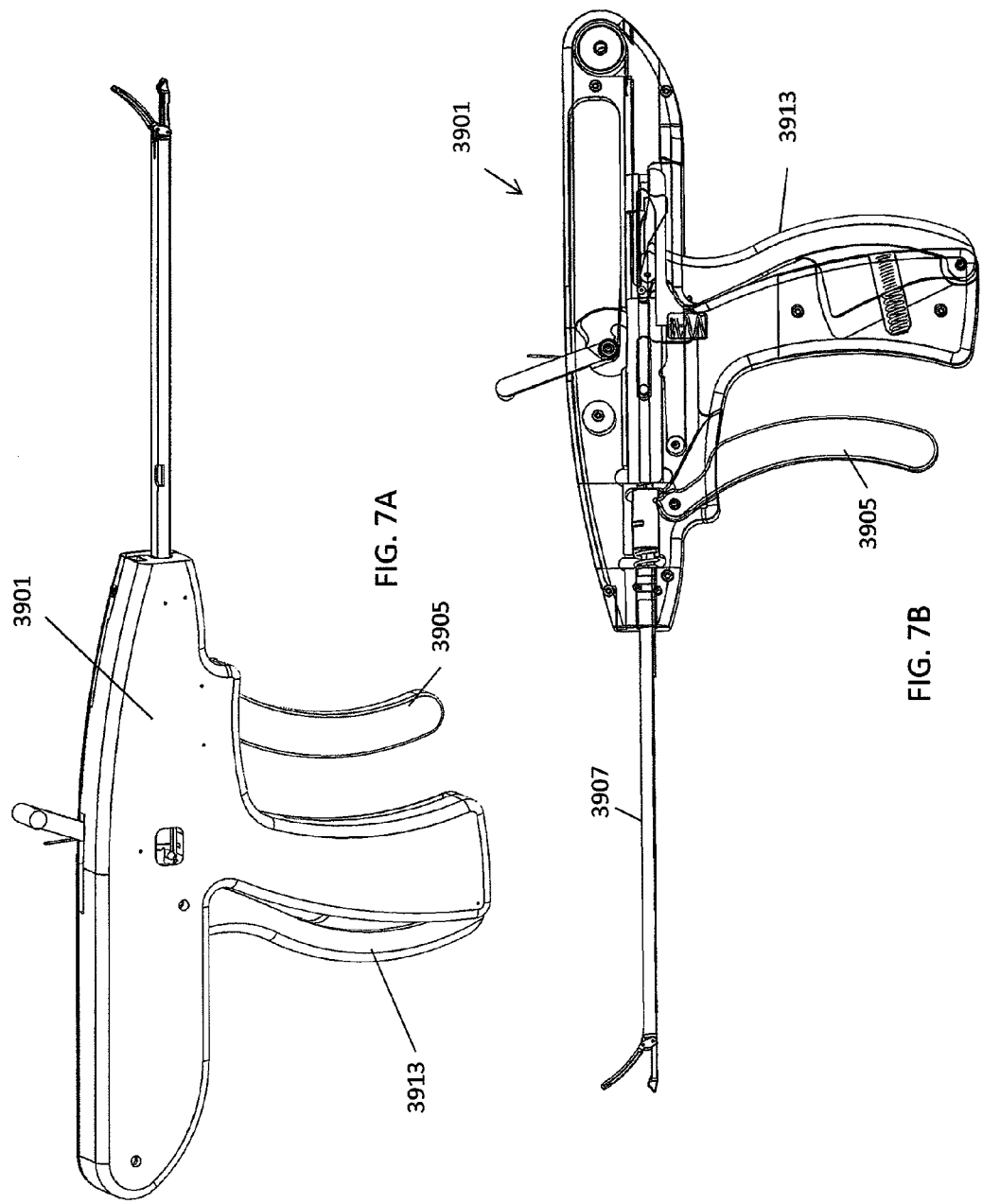

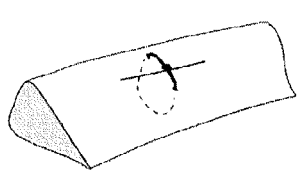
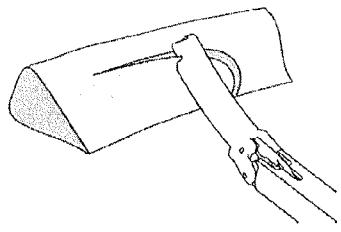
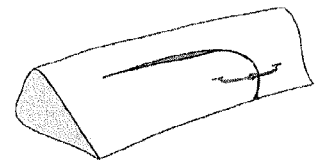
FIG. 12A
FIG. 12B
FIG. 12C

PRE-TIED SURGICAL KNOTS FOR USE WITH SUTURE PASSERS

CROSS REFERENCE TO RELATED APPLICATIONS

This patent application claims priority to U.S. Provisional Patent Application No. 61/698,528, filed on Sep. 7, 2012 and titled "PRE-TIED SURGICAL KNOTS FOR USE WITH SUTURE PASSERS," herein incorporated by reference in its entirety.

The pre-tied knots described herein may be used, in particular, with, or as part of any of the suture passer devices and systems described in the following patent applications, each of which is herein incorporated by reference in its entirety. Specifically: U.S. patent application Ser. No. 11/773,388, filed on Jul. 3, 2007, titled "METHODS AND DEVICES FOR CONTINUOUS SUTURE PASSING," now Publication No. US-2009-0012538-A1; U.S. patent application Ser. No. 12/972,222, filed on Dec. 17, 2010, titled "METHODS AND DEVICES FOR CONTINUOUS SUTURE PASSING," now Publication No. US-2011-0087246-A1; U.S. patent application Ser. No. 13/462,760, filed on May 2, 2012, titled "METHODS OF MENISCUS REPAIR," now Publication No. US-2012-0239062-A1; U.S. patent application Ser. No. 13/006,966, filed on Jan. 14, 2011, titled "METHODS FOR CONTINUOUS SUTURE PASSING," now Publication No. US-2011-0130773-A1; U.S. patent application Ser. No. 13/090,089, filed on Apr. 19, 2011, titled "METHODS OF MENISCUS REPAIR," now Publication No. US-2011-0218557-A1; U.S. patent application Ser. No. 12/291,159, filed on Nov. 5, 2008, titled "SUTURE PASSING INSTRUMENT AND METHOD," now Publication No. US-2010-0331863-A2; U.S. patent application Ser. No. 12/972,168, filed on Dec. 17, 2010, titled "SUTURE PASSING INSTRUMENT AND METHOD," now Publication No. US-2011-0152892-A1; U.S. patent application Ser. No. 13/062,664, filed on Apr. 19, 2011, titled "KNOTLESS SUTURE ANCHORS," now Publication No. US-2011-0190815-A1; U.S. patent application Ser. No. 12/620,029, filed on Nov. 17, 2009, titled "METHODS OF SUTURING AND REPAIRING TISSUE USING A CONTINUOUS SUTURE PASSER DEVICE," now Publication No. US-2010-0130990-A1; U.S. patent application Ser. No. 12/942,803, filed on Nov. 9, 2010, titled "DEVICES, SYSTEMS AND METHODS FOR MENISCUS REPAIR," now Publication No. US-2011-0112556-A1; U.S. patent application Ser. No. 13/462,728, filed on May 2, 2012, titled "DEVICES, SYSTEMS AND METHODS FOR MENISCUS REPAIR," now Publication No. US-2012-0265221-A1; U.S. patent application Ser. No. 13/114,983, filed on May 24, 2011, titled "SUTURING AND REPAIRING TISSUE USING IN VIVO SUTURE LOADING," now Publication No. US-2011-0270280-A1; U.S. patent application Ser. No. 13/347,184, filed on Jan. 10, 2012, titled "IMPLANT AND METHOD FOR REPAIR OF THE ANTERIOR CRUCIATE LIGAMENT," now Publication No. US-2012-0179254-A1; U.S. patent application Ser. No. 13/247,892, filed on Sep. 28, 2011, titled "MENISCUS REPAIR," now Publication No. US-2012-0283750-A1; U.S. patent application Ser. No. 13/323,391, filed on Dec. 12, 2011, titled "SUTURE PASSER DEVICES AND METHODS," now Publication No. US-2012-0283753-A1; and U.S. patent application Ser. No. 13/462,773, filed on May 2, 2012, titled "SUTURE PASSER DEVICES AND METHODS," now Publication No. US-2012-0283754-A1, each of which is incorporated by reference in its entirety.

Many of the pre-tied knot variations described herein were developed for use with one or more of these suture passer devices, and thus may be particularly well adapted for use with these systems. However, the pre-tied knot methods and systems described herein may also be used with other suture passers, or even without suture passers, in order to secure one or more sutures.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present invention relates to suturing techniques, devices and methods, including pre-tied knots for surgical use and methods of forming these knots as well as sutures, suture passers, and other devices including such pre-tied knots. More particularly, described herein are pre-tied suturing knots and methods of using them minimally invasively (e.g., endoscopically). Also described herein are suture methods that use a pre-tied knot (or other fastener) attached to the suture to aid in passing the suture, as well as suture passers adapted for use with suture that has a knot, fastener or other enlarged-diameter region so that the enlarged region (e.g., knot) may be passed through tissue.

BACKGROUND

Suturing of tissue during surgical procedures is time consuming and can be particularly challenging in difficult to access body regions and regions that have limited clearance, such as regions partially surrounded or covered by bone. For many surgical procedures, it is necessary to make a large opening in the human body to expose the area requiring surgical repair. However, in many cases, accessing the tissue in this manner is undesirable, increasing recovery time, and exposing the patient to greater risk of infection.

Suturing instruments ("suture passers" or "suturing devices") have been developed to assist in accessing and treating internal body regions, and to generally assist a physician in repairing tissue. Although many such devices are available for endoscopic and/or percutaneous use, these devices suffer from a variety of problems, including limited ability to navigate and be operated within the tight confines of the body, risk of injury to adjacent structures, problems controlling the position and/or condition of the tissue before, during, and after passing the suture, as well as problems with the reliable functioning of the suture passer.

For example, some surgical instruments used in endoscopic procedures are limited by the manner in which they access the areas of the human body in need of repair. In particular, the instruments may not be able to access tissue or organs located deep within the body or that are in some way obstructed. In addition, many of the instruments are limited by the way they grasp tissue, apply a suture, or recapture the needle and suture. Furthermore, many of the instruments are complicated and expensive to use due to the numerous parts and/or subassemblies required to make them function properly. Suturing remains a delicate and time-consuming aspect of most surgeries, including those performed endoscopically.

During or after performance of a surgical procedure, tissues must be stitched or sutured to allow or encourage healing. Suturing, that is, the tying a tissue with a suture (e.g., thread), is well-known in the art. Moreover, pre-tied sutures and methods of suturing for external surgical use likewise are known, such as is described in U.S. Pat. No. 3,580,256 to Wilkinson et al. The Wilkinson patent describes a pre-tied suture that is encased in a see-through material, taking the form of a thin, flat wafer. In use, the surgeon stitches the tissue together and then directs the needle through the loops in the wafer and draws it tight in order to make the knot. Clearly, such a convention could not be used for endoscopic and other internal surgical techniques.

In contrast, minimally invasive surgery, such as endoscopic surgery, is performed within the interior of a body, including a body cavity or hollow organ, with the help of an endoscope or similar device to visualize the interior portions of the body where the surgery is to be performed. Small, low-profile or compact devices, such as suture passers, may be used to pass a suture through the tissue, and subsequently tie off the suture. The surgeon may observe the surgical procedure through a visual device whose output is displayed on a video monitor.

In order to perform the suturing within patient's body, a suture passer with a tissue penetrator (e.g., needle) element may pass through the tissue one or more times (including through a tissue and a non-tissue material, such as an implant, graft, etc.). The tissue penetrator may pass a suture directly, or it may pass an element that can later pull a suture through the tissue. A problem may arise in manipulating the tissue penetrator (e.g., needle) for easily tying a knot for closing the surgical incision in situ. It is challenging to tie off or otherwise secure the free end or ends of a suture, particularly minimally invasively. Thus, it is to be appreciated that a pre-tied suture, employable with a suture passer or grasping instrument, could greatly facilitate minimally invasive and other surgical procedures (even including open procedures). The present invention is directed to such methods and systems for knotting suture that allow a pre-tied knot to be present, pre-attached or pre-tied onto the suture before performing the surgical procedure.

It is also desirable to suture tissue using a suture passer that can reliably transfer a suture through the tissue without dropping the suture. Described herein are suture passers and methods of passing sutures that enhance reliability by passing a suture that is pre-knotted or otherwise includes an enlarged region on the suture (e.g., near the end region of a suture) to reliably pass the suture (including the knot) through the tissue.

SUMMARY OF THE DISCLOSURE

The present invention relates to pre-tied knots. In particular, described herein are pre-tied knots that maybe used percutaneously with a suture passer. The pre-tied knots may include a knot body and a leader snare. The suture with a pre-tied knot may (prior to being knotted to the other end or a different suture) be passed through the tissue. Thus, the pre-tied knots described herein are particularly helpful for use with suture passers that may be used minimally invasively (e.g. percutaneously). Also described are methods of knotting a suture using the pre-tied knots described herein, including in particular, methods of percutaneously repairing a torn meniscus using these pre-tied knots.

In general, described herein are sutures including pre-tied knots. The pre-tied knot may include a knot body that is secured to, and may be formed of, the suture. The pre-tied knot may also include a leader snare that is tied to the suture by the knot body. The leader snare typically includes a first end with a loop region (e.g., a bight) that can be threaded to hold an end of the suture, and a second end which is a tail or pull tail that can be pulled on to pull the leader snare out of the knot body. When an end of the suture is threaded into the loop/bight region, pulling the tail of the leader snare results in closing the loop of suture at the knot body. The loop can then be cinched and/or the knot body tightened to securely knot the loop.

For example a suture may have a pre-tied knot including: an elongate flexible length of suture (formed of suture material) having a first end and a second end; a knot body formed from the suture material at a region near the first end of the suture, the knot body having one or more loops of the suture material, wherein each loop has at least one crossing point; and a leader snare formed of a length of linear and flexible material that is distinct from the suture material forming the knot body, the leader snare passing through the one or more loops of the knot body, wherein the leader snare comprises a loop or bight extending from a first end of the knot body and a pull end extending from a second end of the knot body, wherein the knot body and leader snare are sufficiently flexible and narrow of profile to be pulled through a tissue behind a tissue penetrator. The tissue penetrator may be any of the tissue penetrators incorporated by reference above as part of a suture passer, or it may be a simple needle (including curved needles).

The knot body may have one, two, three, four, five or more loops of suture material. In some variations, the knot body includes three or more loops of suture material.

The leader snare may be formed of a second piece of suture material. The loop or bight of the leader snare may extend towards the second end of the suture and the pull end of the leader snare may extend towards the first end of the suture. In some variations, the material forming the leader snare has a larger diameter than the suture.

In some variations, the knot body is configured to slide along the length of the suture. In other variations the knot body is relatively fixed along the length of the suture.

Although the examples provided above include knot bodies formed of the suture (e.g., of the length of suture), in some variations the knot body is a separate length of material (e.g., suture material) that is tied to the length of suture. Alternatively, the knot body may be formed of a some other material (non-suture material) including polymeric materials, metals, alloys, ceramics, etc.

The pre-tied knot may be positioned at any position along the length of the elongate suture. In some variations the pre-tied knot body is located at the proximal or distal ends. In some variations the pre-tied knot is locate near the middle region of the suture. In some variations, the pre-tied knot is located proximal to the distal end of the device. As mentioned above, in some variations, the pre-tied knot body may be formed of a region of the elongate length of suture.

Any of the sutures having pre-tied knots described herein may be used to suture tissue, and in particular to knot a loop of suture through and/or around tissue. For example, described herein are methods of percutaneously tying a loop of suture around tissue using a pre-tied knot, wherein the suture has a proximal end, a distal end, and a pre-tied knot formed between the proximal and distal ends, wherein the pre-tied knot is tied around a leader snare so that a loop of the leader snare extends from the pre-tied knot in a first direction and a tail of the leader snare extends from the pre-tied knot in a second direction, the method comprising: percutaneously passing the distal end of the suture through the tissue; percutaneously passing the leader snare through the tissue; passing the distal end of the suture through the loop of the leader snare; forming a loop of suture by pulling the tail of the leader snare to draw the suture through the pre-tied knot while removing the leader snare from the pre-tied knot; and cinching the loop of suture around the tissue.

As mentioned, in some variation the methods may be used to knot a loop of suture using a suture passer. For example, percutaneously passing the distal end of the suture comprises using a suture passer to pass the distal end of the suture. Percutaneously passing the leader snare may comprise using the suture passer to pass the leader snare. Percutaneously passing the leader snare may comprise percutaneously passing the loop of the leader snare through the tissue.

Any of these methods may also be used to form a loop of suture around a torn meniscus. For example, percutaneously passing the distal end of the suture may comprise percutaneously passing the distal end of the suture from the inferior to the superior side of a meniscus.

Cinching may comprise pulling the distal end of the suture, which may reduce the size of the loop. Cinching may also or alternatively comprise tightening the pre-tied knot over the suture. For example, the knot body may be tightened by pulling an end of the length of material forming the knot body to reduce the size (e.g., diameter) of any loops forming the knot body. As mentioned, in some variations, the knot body of the pre-tied knot is formed from the suture; in some variations the knot body is formed of a separate length of suture or other material.

In one variation, a method of percutaneously forming a loop of suture around a tear in a meniscus using a pre-tied knot, wherein the suture has a proximal end, a distal end, and a pre-tied knot formed between the proximal and distal ends, and wherein the pre-tied knot is tied around a leader snare so that a loop of the leader snare extends from the pre-tied knot in a first direction and a tail of the leader snare extends from the pre-tied knot in a second direction, may include the steps of: percutaneously passing the distal end of the suture from an inferior surface to a superior surface of the meniscus; percutaneously passing the leader snare from the inferior surface to the superior surface of the meniscus; passing the distal end of the suture through the loop of the leader snare; forming a loop of suture by pulling the tail of the leader snare to draw the distal end of the suture from the superior surface to the inferior surface and through the pre-tied knot while removing the leader snare from the pre-tied knot; and cinching the loop of suture around the meniscus.

In some variations, a method of percutaneously forming a loop of suture around a tear in a meniscus using a pre-tied knot, wherein the suture has a proximal end, a distal end, and a pre-tied knot formed between the proximal and distal ends, wherein the pre-tied knot is tied around a leader snare so that a loop of the leader snare extends from the pre-tied knot in a first direction and a tail of the leader snare extends from the pre-tied knot in a second direction, includes: percutaneously passing the distal end of the suture from a superior surface to an inferior surface of the meniscus; percutaneously passing the leader snare from the superior surface to the inferior surface of the meniscus; passing the distal end of the suture through the loop of the leader snare; forming a loop of suture by pulling the tail of the leader snare to draw the distal end of the suture from the inferior surface to the superior surface and through the pre-tied knot while removing the leader snare from the pre-tied knot; and cinching the loop of suture around the meniscus.

Also described herein are methods of using a suture having a pre-tied suture knot. For example, described herein are methods of suturing tissue using a length of suture with a pre-tied knot, these methods including the steps of: passing a suture through a tissue, wherein the suture comprises a knot body at a region of a first end of the suture, the knot body having one or more loops of the suture around a leader snare, wherein each loop has at least one crossing point, and further wherein the leader snare comprises a loop or bight formed of a length of linear and flexible material extending from a first end of the knot body and a pull end extending from a second end of the knot body; passing a second end of the suture through the loop or bight of the leader snare; pulling the pull end of the leader snare to draw the second end of the suture through the knot body and removing the leader snare from the knot body; and tightening the knot body around the second end of the suture and knotting the suture.

The step of passing the suture through the tissue may further comprises passing the knot body through the tissue. As mentioned, the pre-tied knot may be sufficiently flexible and narrow diameter to pass through the tissue behind a tissue penetrator.

In some variations, the method also includes the step of sliding the knot body along the suture.

In some variations, the knot body may be tightened by pulling the first and second ends of the suture. Once the knot is tightened, the free ends of the suture may be cut and removed.

The step of passing the suture through the tissue may include passing the suture endoscopically using a suture passer. As mentioned above, in particular, the methods described herein may be used to repair a torn meniscus of the knee. Thus, the method may include passing the suture through the meniscus tissue. In some variations, passing the suture comprises passing the second end of the suture through a first region of the tissue and passing the first end of the suture and the knot body through a second region of the tissue.

In some variations, described herein are method of passing a suture through tissue using a tissue passers in which the portion of the suture passed by the tissue passer includes a knot (or other enlarged region) that is driven through the tissue. Although it is counterintuitive to pass a knotted portion of a suture through the tissue during repair of the tissue, the inventors have found this method to be surprisingly effective. Also described herein are suture passers that may be used in even the most constricted anatomical regions for minimally invasively (e.g., arthroscopically) passing a suture including a knotted region through the tissue. In some variations the devices and methods may be adapted to pass multiple lengths of suture (having multiple knots or enlarged regions on the suture) through the tissue using the same device without having to remove the device from the tissue to reload between passes.

BRIEF DESCRIPTION OF THE DRAWINGS

FIGS. 5B and 5K show the pre-tied knot used with a suture anchor.

FIGS. 7A-7C show one variation of a suture passer.

FIGS. 11A-11G and 12A illustrate one method of suturing a tissue in a loop using a suture passer such as the suture passer shown in FIG. 7A.

FIGS. 12B and 12C illustrate suturing complex meniscal tears, including those having a radial tear, using a suture passer such as the one shown in FIG. 7A.

DETAILED DESCRIPTION

Figure 1A:
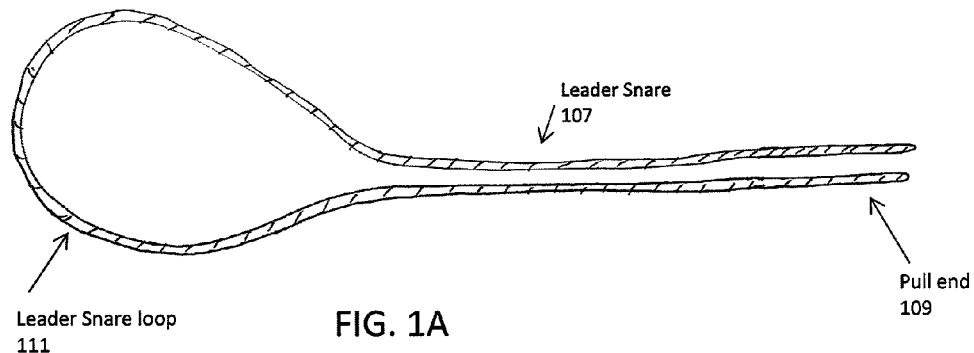
FIGS. 1A to 1D show variations of pre-tied suture knots (FIGS. 1C and 1D) including a leader snare (FIG. 1A) that passes through one or more loops of a knot body (FIGS. 1B, 1C and 1D).

Described herein are sutures with pre-tied suture knots that are compatible for use in minimally invasive surgical techniques using a suture passer. The structure of different types of pre-tied knots are described herein, including variations that may result in different knots, variations formed of the suture material themselves, and variations formed of different material(s) that may be connected to the suture. In addition, methods of forming, placing and tying pre-tied knots are also described. Finally, examples of the use of a pre-tied knot to repair, anchor and otherwise fix tissue or tissue and implants (e.g., explants, implantable medical devices, and the like) are also provided herein.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all subranges subsumed therein.

The pre-tied knots described herein may be used with any appropriate type of suture material, including any appropriate size, length and/or diameter of suture material. Examples of suture materials may include: surgical-grade sutures such as catgut (plain, chromic), silk, polyglycolic acid, polylactic acid, polydioxanone, nylon, polypropylene, etc.

A pre-tied knot may refer to one or more knots formed in a length of suture, and may generally include both the knot body as well as a leader snare that is knotted to the length of suture by the knot body. The pre-tied knot may be formed exclusively of suture material, or it may include one or more additional materials, and/or it may modify the suture material, or it may be formed of non-suture materials (such as metals, alloys, etc.). The pre-tied knot (e.g., the knot body of the pre-tied knot) may be loose or taut, and may be movable along a portion of the length of a suture or it may be fixed relative to a position on the length of suture. The knot body of the pre-tied knot may be formed of the same material as the suture on which the pre-tied knot is located, or it may be formed of a different material. The knot body may be fixed or moveable along the length of the suture from where it is positioned. The knot-body may also be tightenable. In some variations the knot body is formed at the end of the length of suture from the end of the suture material.

Structure of a Pre-Tied Knot

In general, a pre-tied suture knot as described herein may include a knot body region and a leader snare that passes through the knot body. The knot body ties the leader snare to the length of suture. In some variations the pre-tied knot is configured to tie together a first length of suture to second length of suture. The first and second lengths of suture may be on the same suture (e.g., forming a loop of suture) or they may be from different sutures.

As mentioned, any appropriate suture may be used with the pre-tied knots described herein. Thus a length of suture may be formed of any appropriate material, and particularly linear materials compatible for surgical use. A suture may be referred to as a suture or a suture thread, suture length, suture wire, suture braid, or the like. The suture may be made from appropriate materials, including biological materials, such as catgut suture and silk and synthetic materials, including the polyglycolic acid, polylactic acid, and polydioxanone, nylon and polypropylene. Sutures may be coated (e.g., with antimicrobial substances, growth-promoting substances, or the like), and may come in any appropriate sizes or ranges of sized. For example a suture of diameter from less than 0.01 mm diameter to greater than 0.8 mm may be used to form the suture. The suture may be monofilament or multifilament (e.g., braided).

In some variations, the knot-body of the pre-tied suture typically may include one or more loops through which the leader snare, and ultimately one or more ends of the suture, is positioned. The loop or loops may be cinched, tighten, and/or closed around the leader snare and/or suture, as described in more detail below. The loop(s) of the knot body typically extends along a region of the length of the suture.

In some variations, the knot body may be configured as a suture trap that allows one-way movement of a length of suture through the suture trap.

In some variations the knot body is formed and/or positioned near one end, e.g., a first end, of the suture. Although generally the knot body may be formed from a portion of the length of the suture, in some variations the knot body is instead formed of a separate material that is not part of the suture length. In some variations the knot body is formed of a different length of suture material. In other variations the knot body is not formed of suture material, for example, the knot body may be formed as a trap, clasp, or the like that can be cinched down onto the suture and/or that allows the suture to be pulled through in only one direction, while preventing withdrawal (and loosening) of the suture from the knot body.

As mentioned, the knot body may be slideable along the length of the suture, or it may be relatively fixed along the length of the suture.

A leader snare typically includes a flexible elongate (e.g., linear) body that extend through the knot body. One end of the leader snare may include a snare region, which may be a loop, hook, clasp, or the like, for holding an end of the suture, and a pull end which may be used to draw the leader snare through the knot body after a portion (e.g., the end) of the suture is coupled to the leader snare. This end of the leader snare may be referred to as a loop region or bight region. Drawing the leader snare through the knot body by pulling on the pull end of the leader snare may result in pulling the end of the suture through the knot body, removing the leader snare, and allowing the knot body to form a knot with the knot body to knot the suture. Both ends of the suture may then be drawn to shorten the suture and knot it in the tissue, as illustrated below.

The leader snare may be formed of a separate material from the suture and/or knot body. However, in principle, the leader snare could be formed of one end (e.g., the first end of the suture. In use, the leader snare is configured to be pulled through the knot body after one end of the leader snare is coupled with a length (e.g., the second end region) of the suture. Thus, the leader snare may be held within one or more loops of the knot body. The leader snare may be loosely held, e.g., without tightening the loop(s) of the knot body to tightly over the leader snare. In some variations the leader snare comprises a material that reduces the friction between the leader snare and the suture material. For example, the leader snare may be coated with a "slippery" material (e.g., wax, polymeric coatings, etc.). In some variation the leader snare may have a tapered width so that it can be readily drawn out in one direction (e.g., towards the first end of the suture) by pulling on the pull end. For example the length of the leader snare body held within the loop(s) of the knot body may have a larger diameter at the proximal end (closest to the pull end) that tapers towards the opposite end (the coupling end of the leader snare, e.g., the loop end. In some variations the diameter of the leader snare may be greater than the diameter of the suture. For example, the leader snare may be formed of a suture material that has a larger (e.g., 1.5×, 2×, 3×, etc.) diameter than the diameter of the suture and/or the knot body. This may allow the end of the suture that is pulled through the knot body by the leader snare to be readily slid through the knot body to tighten the suture before knotting it.

As mentioned, the leader snare may be formed of any appropriate material. In some variations, the leader snare is formed of a flexible material. The leader snare may be completely or partially flexible. For example, the leader snare may be formed of a suture material that is identical or similar to the material forming the suture and/or knot body. In some variations, the leader snare is relatively incompressible. For example, at least a portion of the leader snare may be formed of a relatively non-compressible material, including plastics (e.g., polymeric materials). Preventing compression of the body region of the leader snare may help keep the knot body open even when pulling on the ends of the suture to pull the suture through the tissue (e.g., pulling on the first end of the suture proximal to the knot body).

In some variations, the pre-tied knot may include a second pull-string that is passed through the knot body, completely or in part. Removing this pull-string (which may be a string, wire, rod, etc.) may loosen the knot body around the leader snare, and allow it to be more readily drawn through the knot body, and may also allow the end of the suture pulled through the knot body to be more easily slid through the knot body (allowing it to be more easily tightened over the tissue).

The leader snare includes a suture coupling end which may secure a portion (e.g., the second or distal end) of the suture so that it can be pulled through the knot body. As illustrated herein, in some variations the leader snare includes a bight or loop region through which the suture can be placed. Any appropriate coupling means may be used, including non-loop configurations, such as hooks, graspers (e.g., clamps), adhesives, or the like. A bight may refer to any curved section and/or loop in a linear material (e.g., string, wire, rope, fiber, braid, suture, etc.).

Figure 2A:
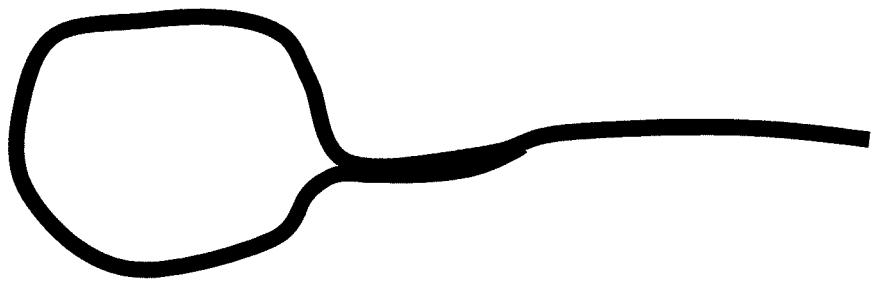
FIGS. 2A and 2B show two variations of leader snares similar to that shown in FIG. 1A.
Figure 2B:
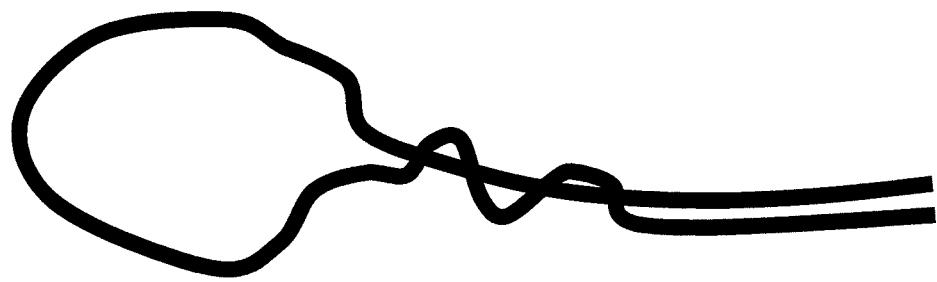

FIGS. 1A, 2A and 2B illustrate variations of leader snares that may be used with the pre-tied knots described herein. For example, in FIG. 1A, the leader snare includes a distal loop region 111 that is formed from the suture material forming the leader snare 107. The loop is formed by doubling the suture material over on itself. The end of the leader snare opposite the loop is the pull end 109, and consists of the two ends of the suture. In some variations (e.g., FIG. 2A) the pull end is only a single end. For example, the loop of the leader snare may be formed by securing the ends of the loop together leaving a single end region. In FIG. 2B, the suture forming the leader snare has been shaped into the loop region and the suture has been wrapped around itself; alternatively, the ends of the fiber forming the leader snare may be connected, woven or otherwise attached to each other.

Figure 1B:
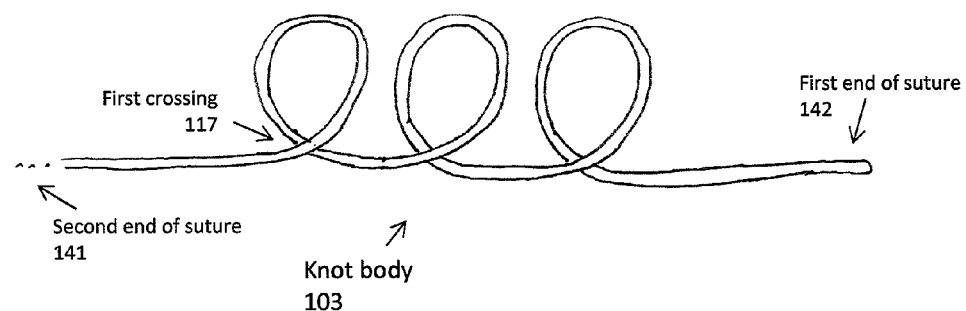
Figure 1C:
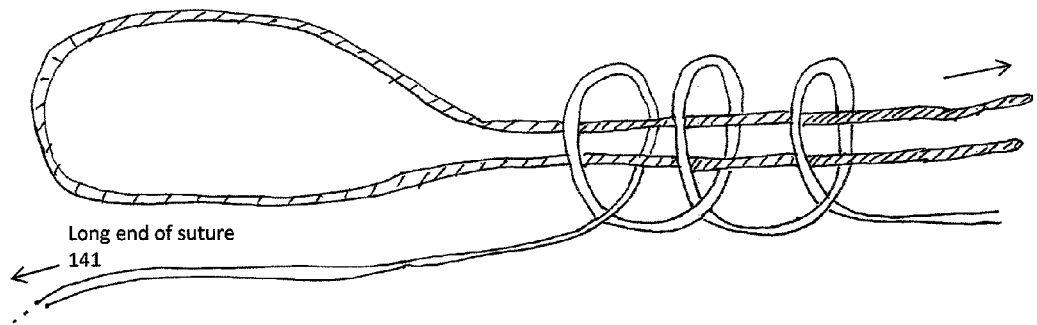

FIG. 1B shows one variation of a knot body that may be used as part of a pre-tied knot, as shown in FIG. 1C. In this example, the knot body 103 includes three loops, where each loop includes a single crossing 117. The loops are formed from the suture material near the first end of the suture 142. The leader snare 107 shown in FIG. 1A is positioned within the knot body 103 as shown in FIG. 1C, so that the leader snare loop 111 extends towards the long end of the suture (the second end 141) while the pull end of the leader snare extends proximally towards the first end of the suture 142.

Figure 1D:
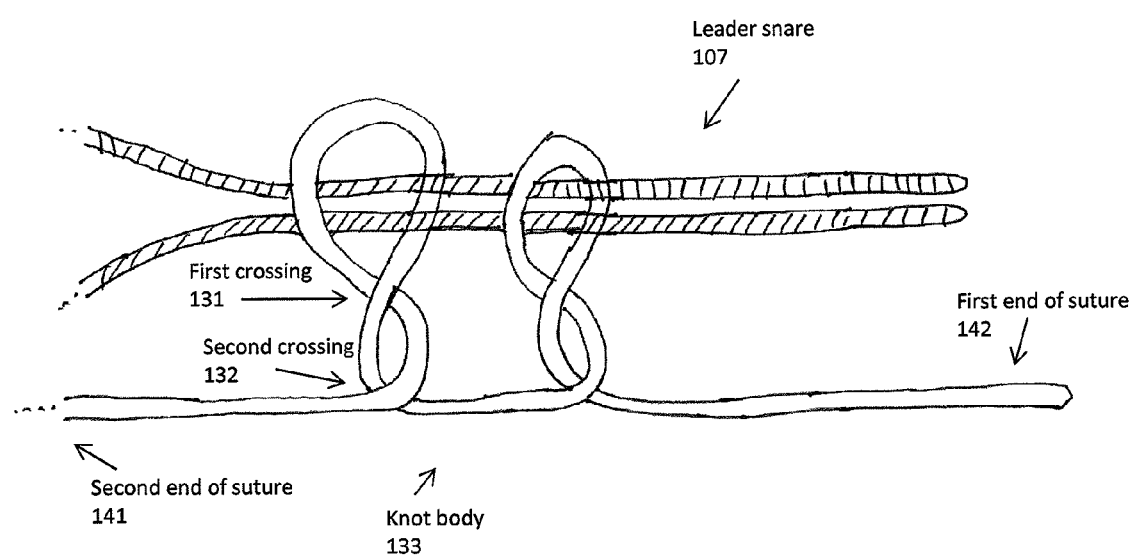

Another variation of a pre-tied knot is shown in FIG. 1D. In this example, the same leader snare 107 shown in FIG. 1A is illustrated within a knot body 133 formed from two loops (though more could be used), each loop formed to have two crossings 131, 132.

In some variations, the pull-string described above may be passed through the same loop as the leader snare, or it may be passed through a separate region of the knot body (such as the loop(s) formed between the first and second crossings 131, 132.

Figure 2C:
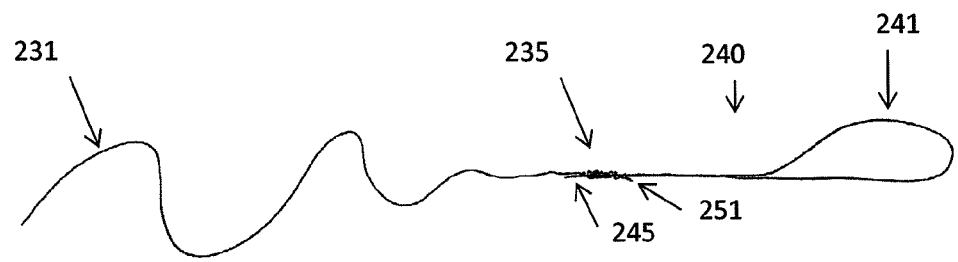
FIG. 2C shows another variation of a length of suture including a pre-tied knot formed of a leader snare similar to the one shown in FIG. 1A.
Figure 2D:
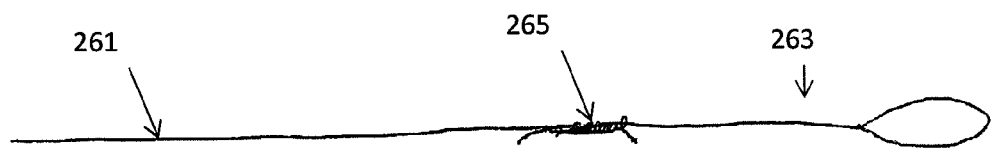
FIG. 2D shows another example of a length of suture including a pre-tied knot, where the pre-tied knot includes a leader snare similar to the one shown in FIG. 2A.
Figure 2E:
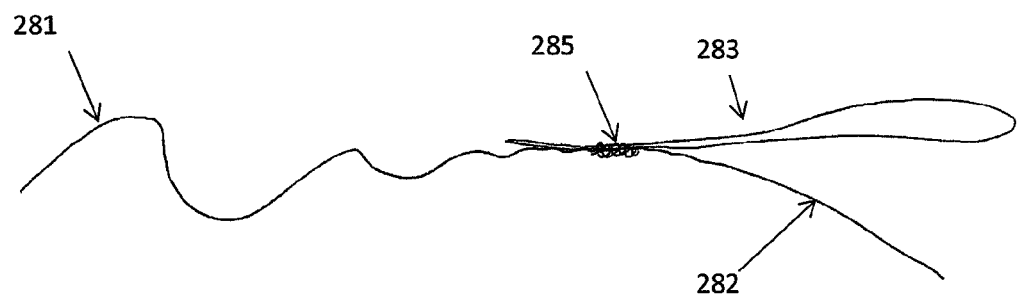
FIG. 2E shows another variation of a length of suture having a per-tied knot, wherein the pre-tied knot is located more towards the medial region of the length of suture than the distal or proximal end regions of the length of suture. Note that the direction of the bight region (to the left, or proximal end) and the direction of the tail of the leader snare may be reversed in any of the variations described herein.

FIGS. 2C-2E illustrate other variations of sutures having pre-tied knots. For example, in FIG. 2C, the length of suture 231 has a proximal and distal end, with the pre-tied knot body 235 formed at the proximal end region 251. A leader snare 240 similar to the leader snare of FIG. 1A, is knotted to the proximal end of the suture 231 by the pre-tied knot body 235, so that the bight region 241 of the leader snare extends proximally from the knot body and the tail (pull tail) 245 extends distally.

FIG. 2D shows another example of a length of suture 261 that has a pre-tied knot body near the proximal end of the length of suture. A leader snare 263, similar to the one shown in FIG. 2A, extends proximally and is tied to the suture by the pre-tied knot body 265. In this example, the leader snare has a loop formed at one end of the leader snare. In some variations the leader snare is a single (e.g., doubled-over) length of suture material forming a loop at one end, and the pull tail at the other end. In some variations the entire leader snare is a loop (closed loop) of material. In FIG. 2D, the tail of the leader snare extends distally and the loop/bight region extends proximally; however, in any of these variations this direction may be reversed, and the direction of the loop/bight may be distal while the tail is proximal.

In FIG. 2E, the pre-tied knot is located away from the proximal 282 and distal 283 ends of the length of suture, and is positioned more medially. In this example, the pre-tied knot body 285 ties the leader snare 832 to the region between the proximal 282 and distal 283 ends of the suture. Either, or both, ends of the suture may be passed through the bight region of the leader snare and pulled through the pre-tied knot body to knot the suture.

Methods of Forming, Positioning and Tying Pre-Tied Knot

As mentioned, a pre-tied knot may be formed at any region of a suture, and it may be slideable or fixed relative to the suture. The pre-tied knot is typically formed before inserting the device into the patient. The pre-tied knot may be made manually or automatically. The loops of the knot body may be formed over the leader snare by sequentially looping a length of suture over the leader snare and twisting the loop to form one or more crossings. In some variations a loop is formed by twisting a bight of suture from a length of suture and passing the leader snare through the loops; the knot body may be tightened slightly over the leader snare to hold it within the knot body.

In use, a suture having a pre-tied knot positioned at one end of the suture may be passed through tissue and an end of the suture may be pulled through the pre-tied knot by passing the end of the suture through the leader snare and pulling the tail or pull end of the leader snare to pull the entire leader snare though the knot body. The knot may be tightened. In some variations, the knot is tightened after pulling the end of the suture through the knot body by pulling one or both ends of the suture to tighten the loop. The knot body may also or alternatively be tightened down on the length of suture to complete the knot. Any loose ends of the suture can then be cut. This entire procedure may be performed minimally invasively (e.g., through a cannula and/or using an endoscope).

For example, FIGS. 3A-3G illustrate one variation of a method for repairing tissue and placing a pre-tied knot in a suture. In this example, the tissue being repaired is the knee meniscus, and the repair may be performed minimally invasively using a suture passer to pass the suture through the tissue, including positioning the pre-tied knot and using the pre-tied knot to secure the suture. Although many of the examples described herein are shown with respect to meniscus, these methods and apparatuses may be used to suture any appropriate tissue, and are not limited to meniscus.

Figure 3A:
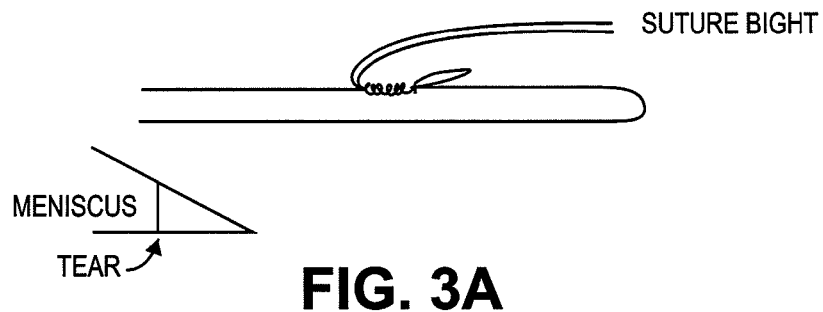
FIGS. 3A-3G illustrate one variation of a method for suturing tissue and knotting the suture with a pre-tied knot such as the pre-tied knot shown in FIG. 1C. In this example the tissue is a torn meniscus that is being repaired endoscopically to form a vertical loop repair, extending through the meniscus twice between the superior and inferior surfaces of the meniscus.
Figure 3B:
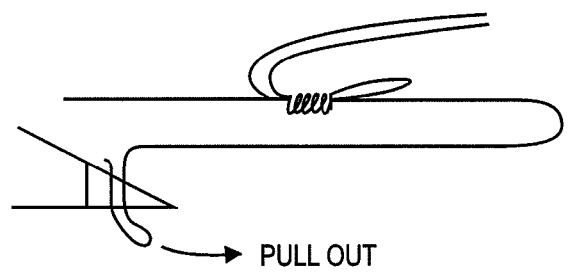
Figure 3C:
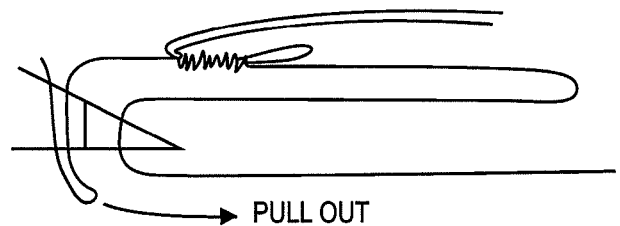
Figure 3D:
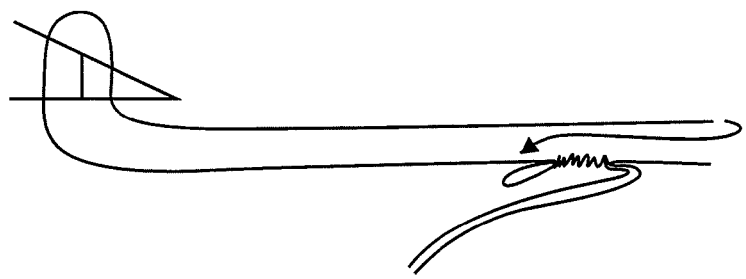

In FIG. 3A, a schematic view of a portion of a torn meniscus (shown in partial cross-section on the left) is shown. A suture including a pre-tied knot (including a leader snare, referred to as a "suture bight" in this example) is passed through the meniscus and around the tear. In FIG. 3B, the distal end of the suture is first passed through the more apical region of the meniscus from the superior to the inferior side of the meniscus, to the apical side of the tear. Thereafter, the proximal end of the suture is passed from the superior to the inferior side of the meniscus on the opposite side of the tear, as shown in FIG. 3C. In FIG. 3D, the proximal end of the suture, including the pre-tied knot, is then drawn through the meniscus tissue.

Figure 3E:
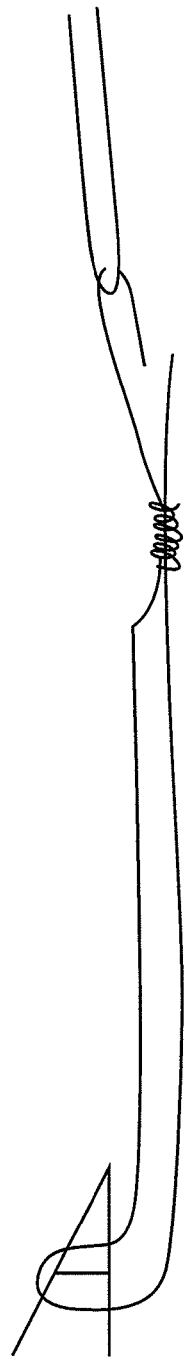
Figure 3F:
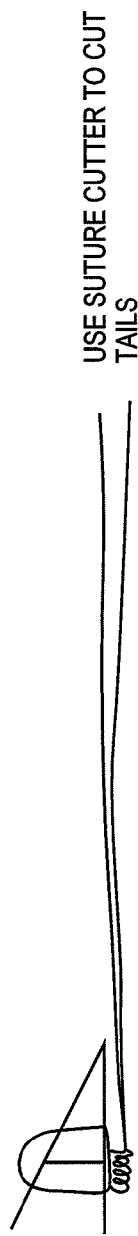
Figure 3G:
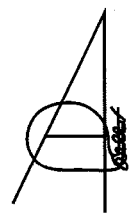

As discussed briefly above, the pre-tied knots described herein in some variations are sufficiently flexible and low-profile that they may be passed through the tissue without substantially damaging the tissue. In FIG. 3D, the pre-tied knot (including the knot body and the leader snare) is pulled through the tissue by the suture passer, which may include a tissue penetrator that can pull the suture through the tissue. Once in position, the distal end of the suture may be passed through the large loop of the leader snare, as shown in FIG. 3D. The pull end of the leader snare may then be drawn proximally, as shown in FIG. 3E, which results in the distal end of the suture passing through the knot body of the pre-tied knot. In FIG. 3F the pre-tied knot is moved towards the tissue by pulling the distal end of the suture, constricting the suture loop formed after pulling the distal end through the knot body around the tissue. Once the tissue is secured, the knot body may be tightened around the suture to tighten the knot, for example by pulling the proximal end of the suture. As shown in FIG. 3G, the ends of the suture may then be cut, leaving the tissue sutured.

Figure 4A:
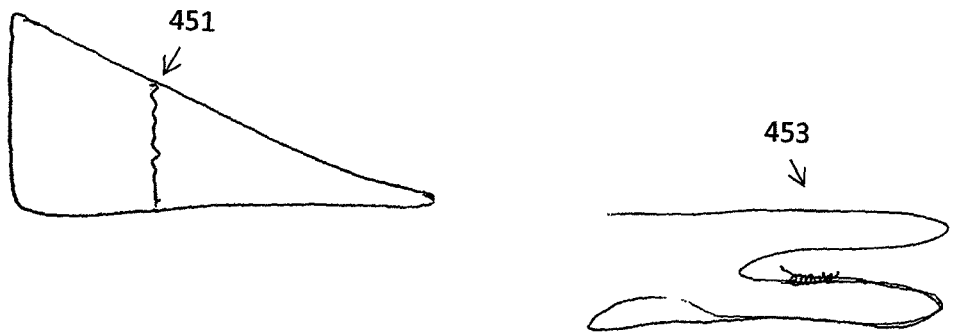
FIGS. 4A-4H show another variation of a method for arthroscopically repairing a torn meniscus by forming a loop of suture around the tear.
Figure 4B:
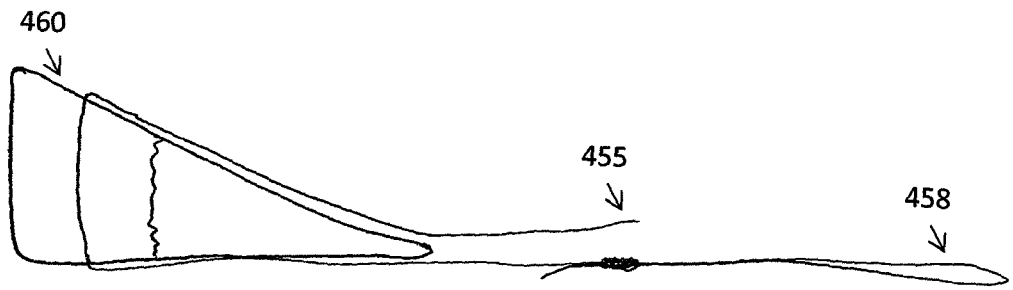
Figure 4C:
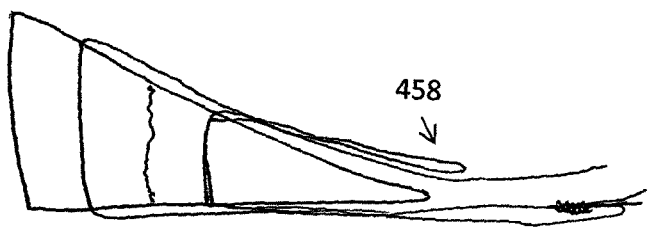

FIGS. 4A-4H illustrate another variation of a method for repairing (arthroscopically) a torn meniscus by forming a loop of suture around the tear. In this example a suture passer (as described in more detail below) may be used to pass the suture through the meniscus of the knee during an arthroscopic procedure. FIG. 4A illustrates the length of suture having a pre-tied knot (similar to that shown in FIG. 2C) that may be used to repair the torn meniscus 451. As shown in FIG. 4B, the distal end of the suture 455 may be initially passed through the meniscus (e.g., from the inferior side of the meniscus to the superior side 460 of the meniscus) on one side of the tear, as shown. In this example, the distal end of the suture may exit the knee region, so that the distal end of the suture extends from an opening in the knee (or out of a cannula, if one is used). The loop region (bight region) of the leader snare may be loaded in to the suture passer (not shown) and passed through the meniscus on the opposite side of the tear, as shown in FIG. 4C. In this example, the bight region is passed from the inferior to the superior surfaces of the meniscus. All or a portion of the bight region may also extend out of the knee (e.g., out of the access opening made into the knee) or it may remain within the tissue. Similarly, a portion of the suture, including the knot body and/or the tail of the leader snare, may extend from the knee so that it can be easily manipulated. Alternatively, it may be within the tissue and manipulated using one or more arthroscopic tools.

Figure 4D:
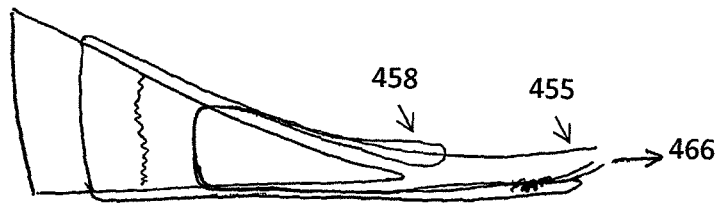
Figure 4E:
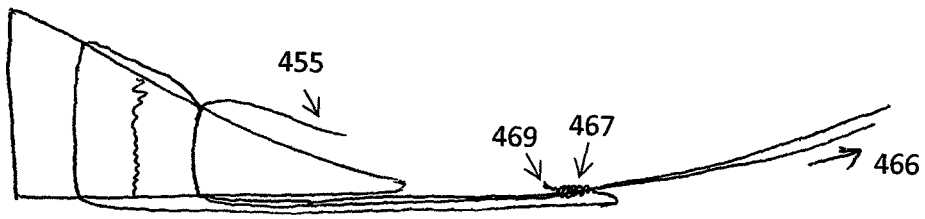
Figure 4F:
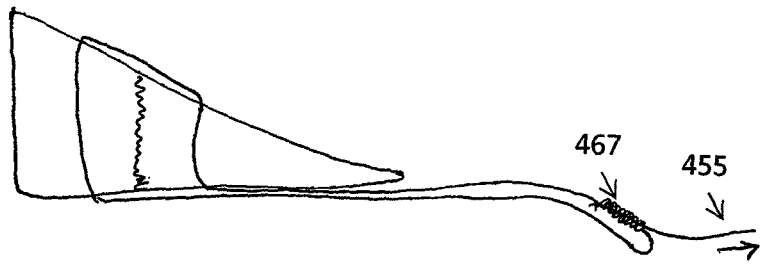
Figure 4G:
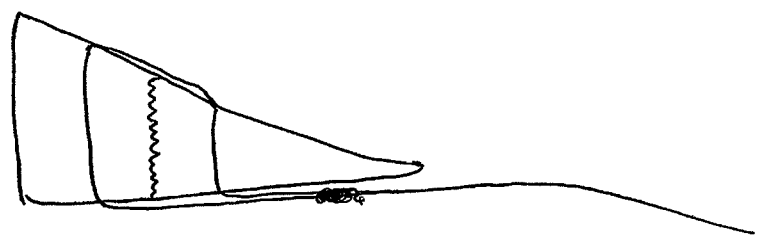
Figure 4H:
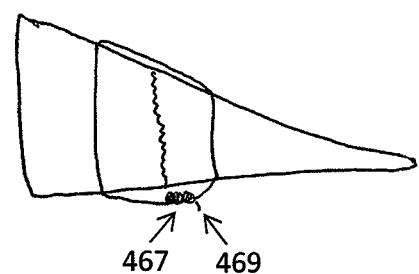

The distal end of the suture 455 may then be passed through the loop of the bight region 458, as shown in FIG. 4D, and thereafter the tail of the leader snare may then be pulled (proximally in this example, as shown by arrow 466) to draw the bight region and the captured distal end of the suture back through the meniscus in the same path already taken by the bight region of the leader snare, as shown in FIG. 4E. Finally, in FIG. 4F, the entire snare leader has been removed, pulling the distal end of the suture through the pre-tied knot body. The distal end of the suture 455 then extends proximally from the knot body in this example. The knot loop formed my then be cinched around the meniscus as shown in FIGS. 4G and 4H. In this example, the loop is cinched by pulling either (or both) pulling on the distal end of the suture 455 and/or pushing on the knot body 467. Once cinched, the pre-tied knot body may also be tightened. For example, one end 469 of the pre-tied knot body may be pulled to tighten the pre-tied knot body. The loose ends of the suture may be cut off, to leave the knot body on the inferior surface of the meniscus, with the loop of suture extending from the superior to the inferior surfaces and back, surrounding the torn region.

Figure 5A:
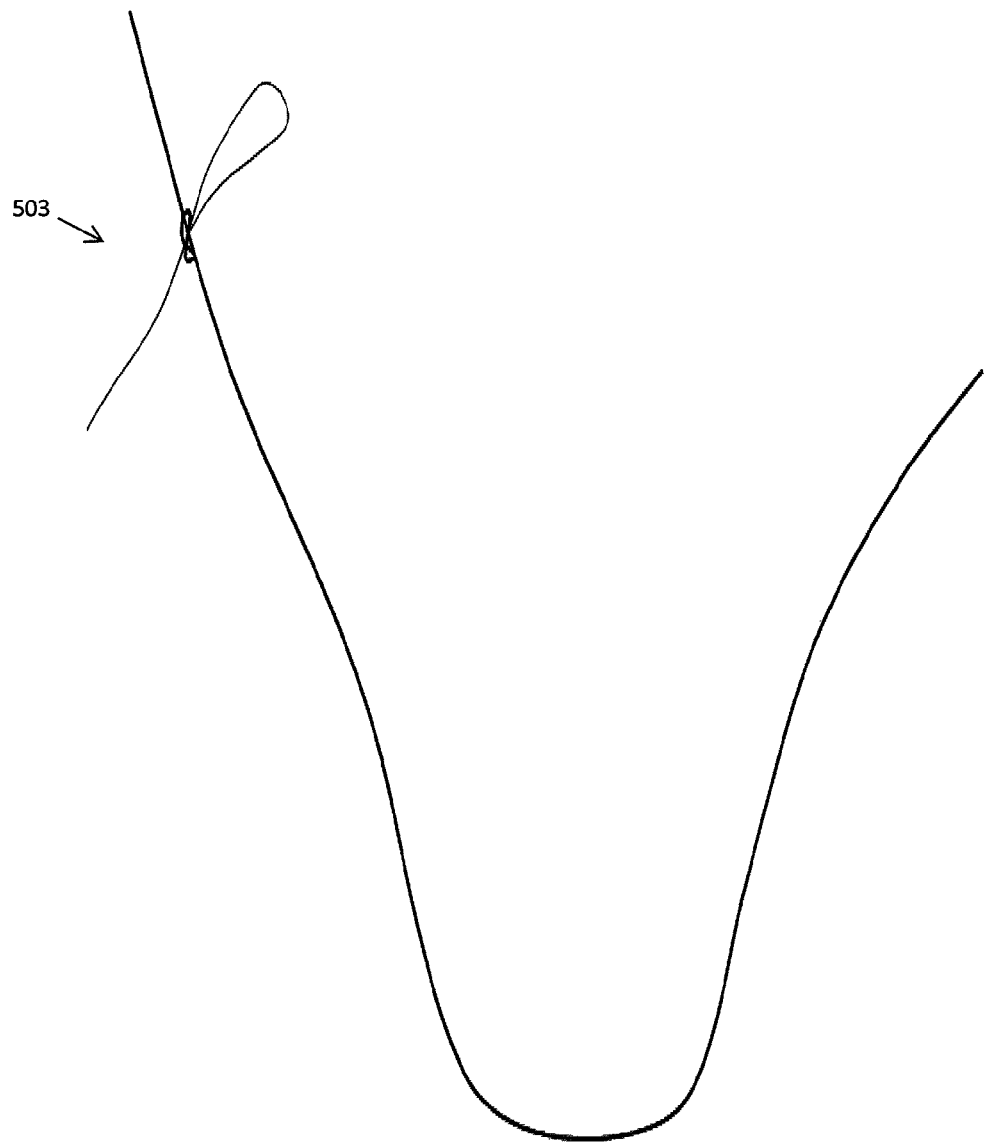
FIGS. 5A-5K illustrate another variation of a pre-tied knot.

Another example of a pre-tied suture is shown in FIG. 5A. In this example a pre-tied sliding knot is positioned around a pull string 503 so that the opposite end of the suture can be easily pulled through the pre-tied knot. One or both suture strands of the suture can be passed through or around tissue. As mentioned above, the pre-tied knot and pull string can together travel through the tunnel made by the tissue penetrator.

Figure 5B:
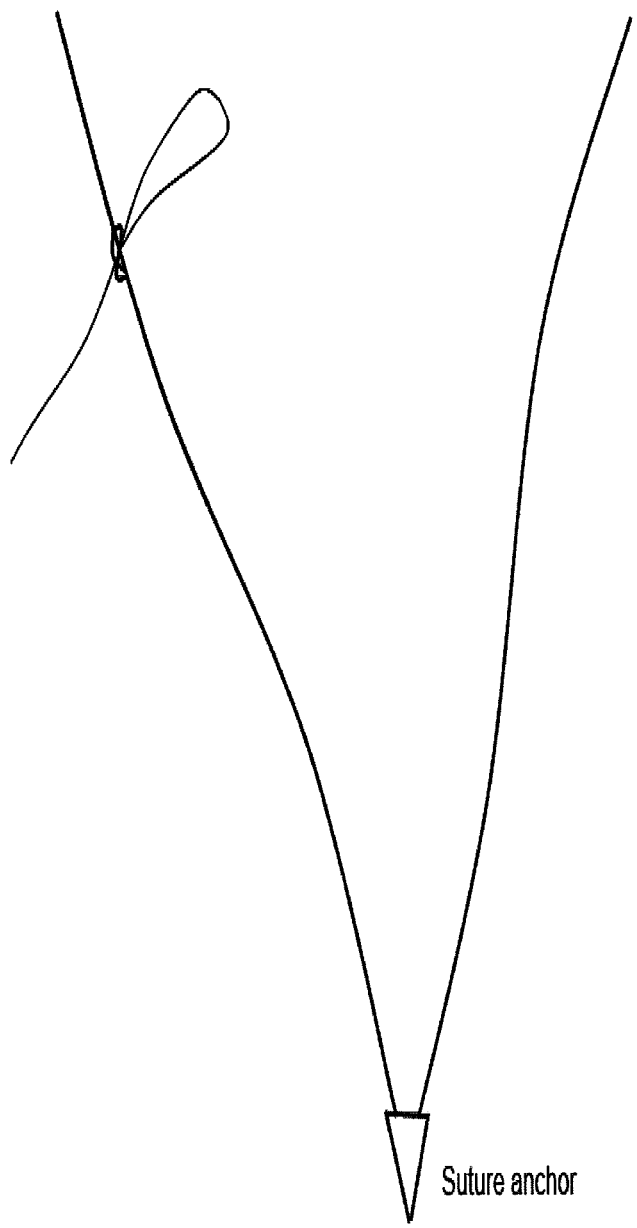

In some variations, the pre-tied knot is used with an anchor, as shown in FIG. 5B. In this example a suture anchor includes a length of suture extending from it, and a pre-tied knot is positioned at the proximal end of one length of suture, as shown.

Figure 5C:
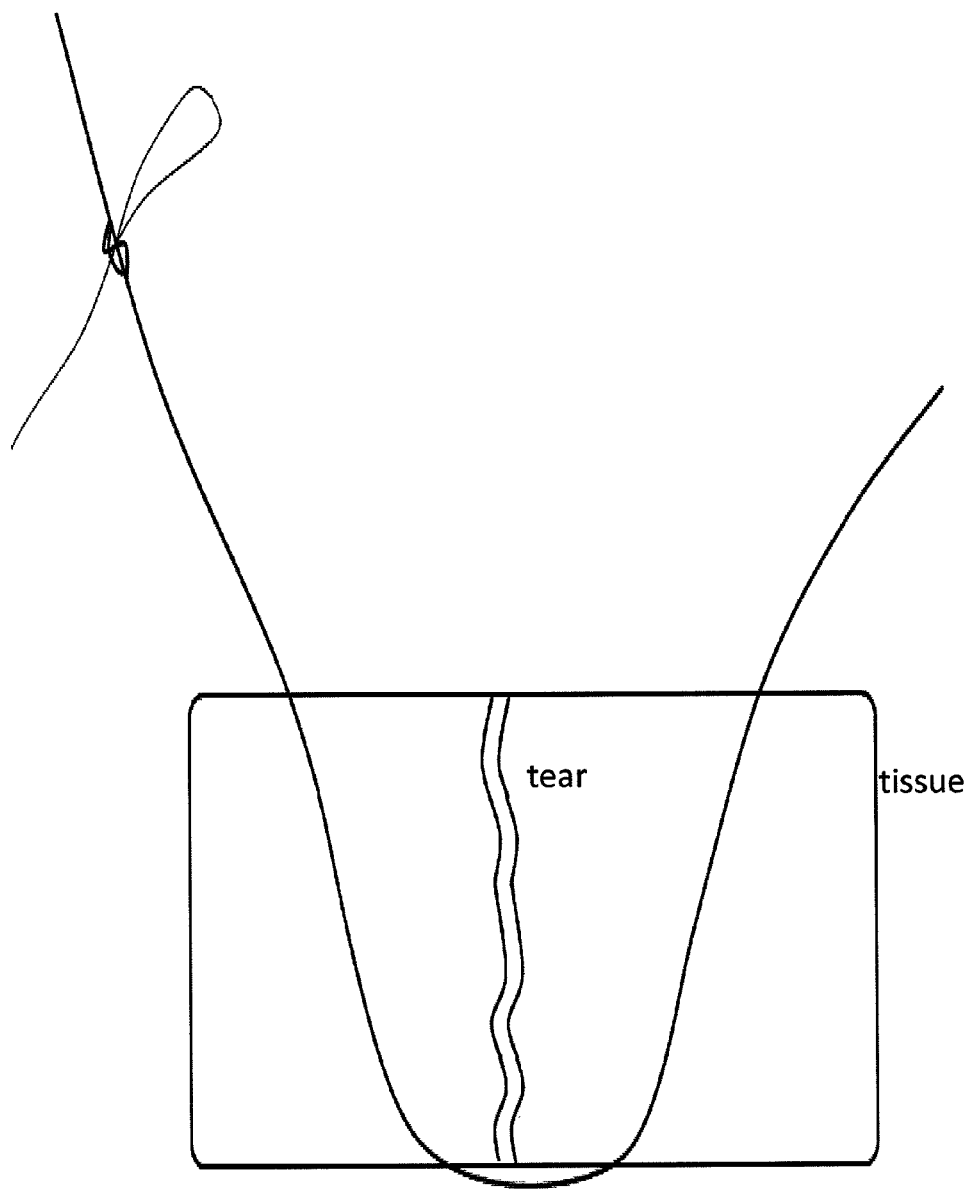
Figure 5D:
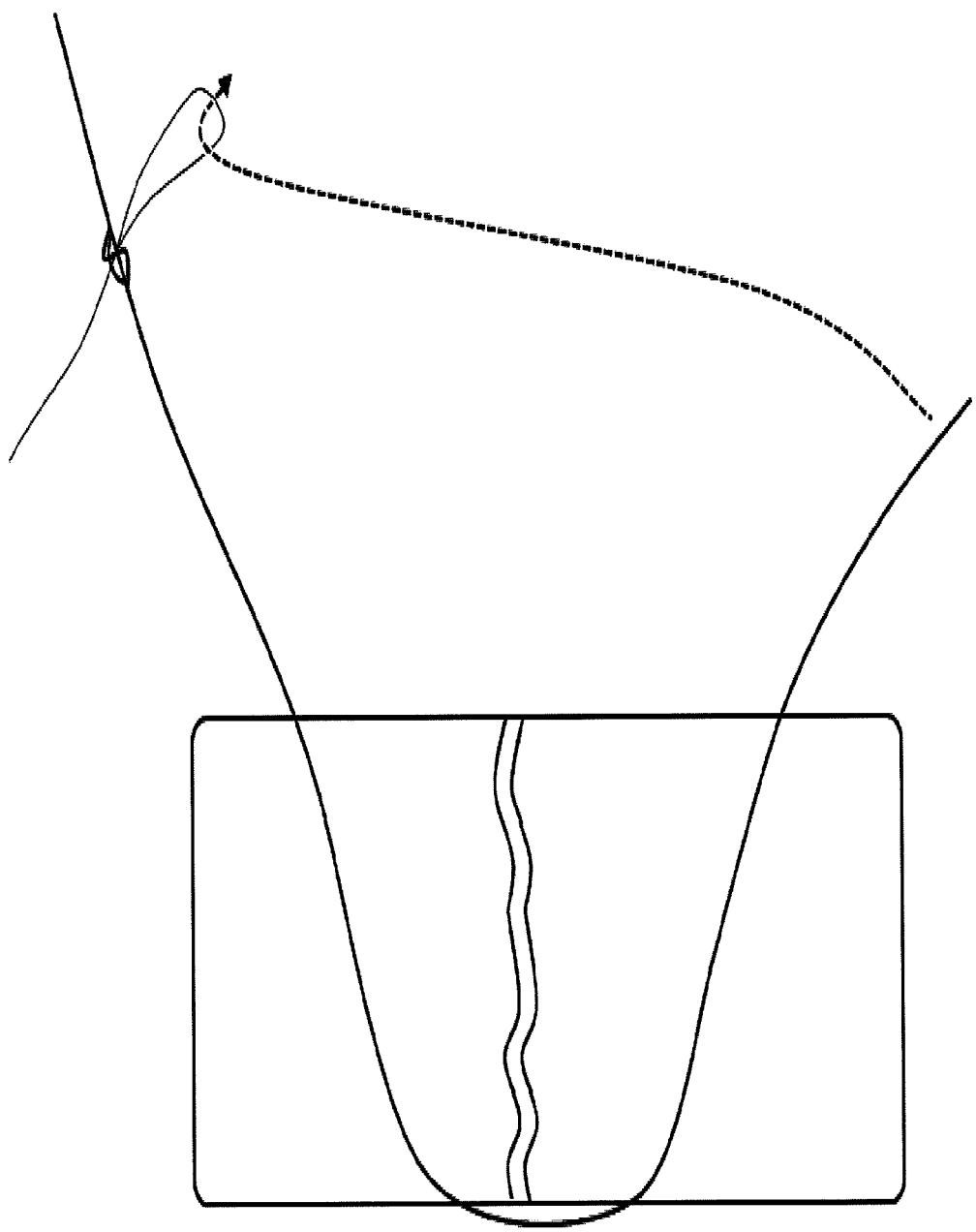
Figure 5E:
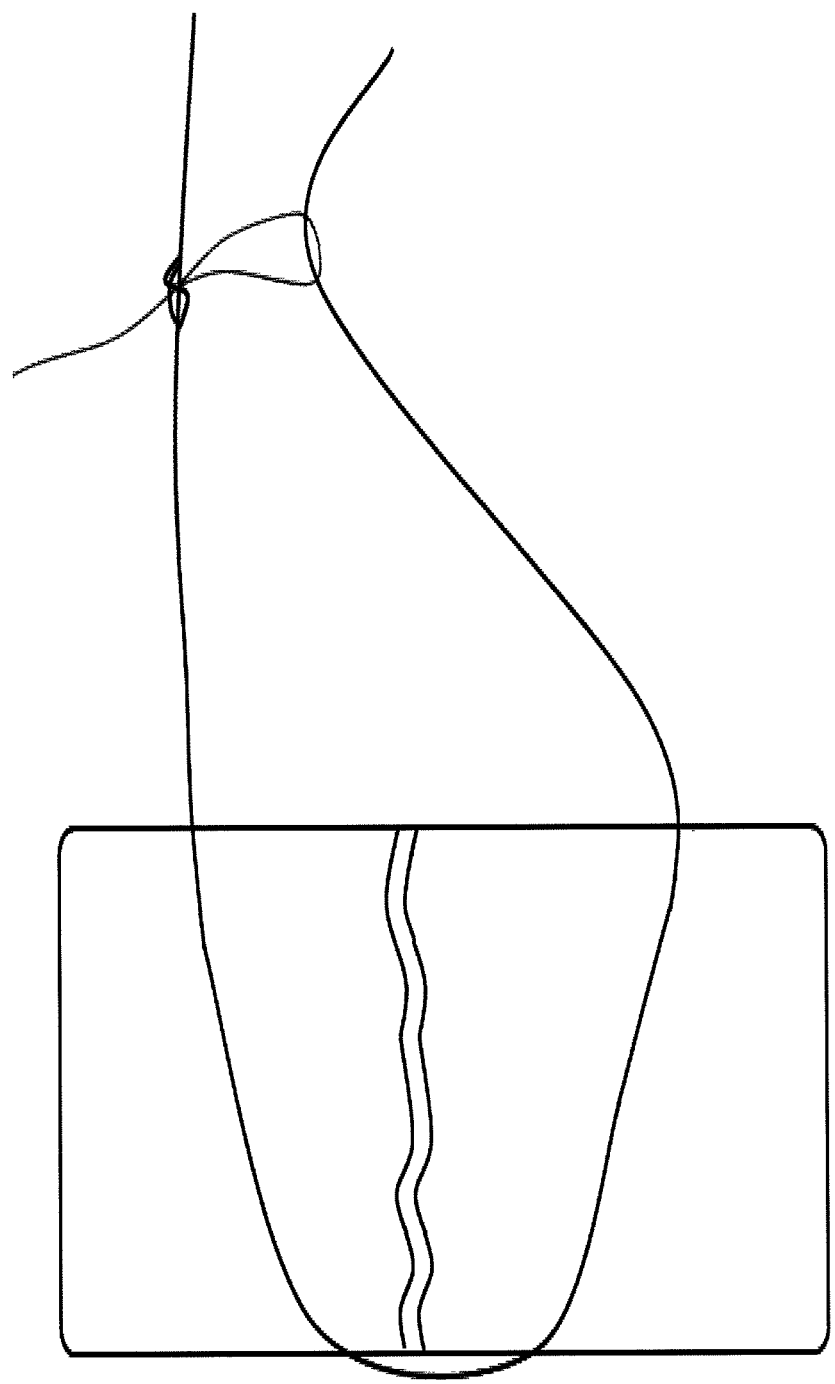
Figure 5F:
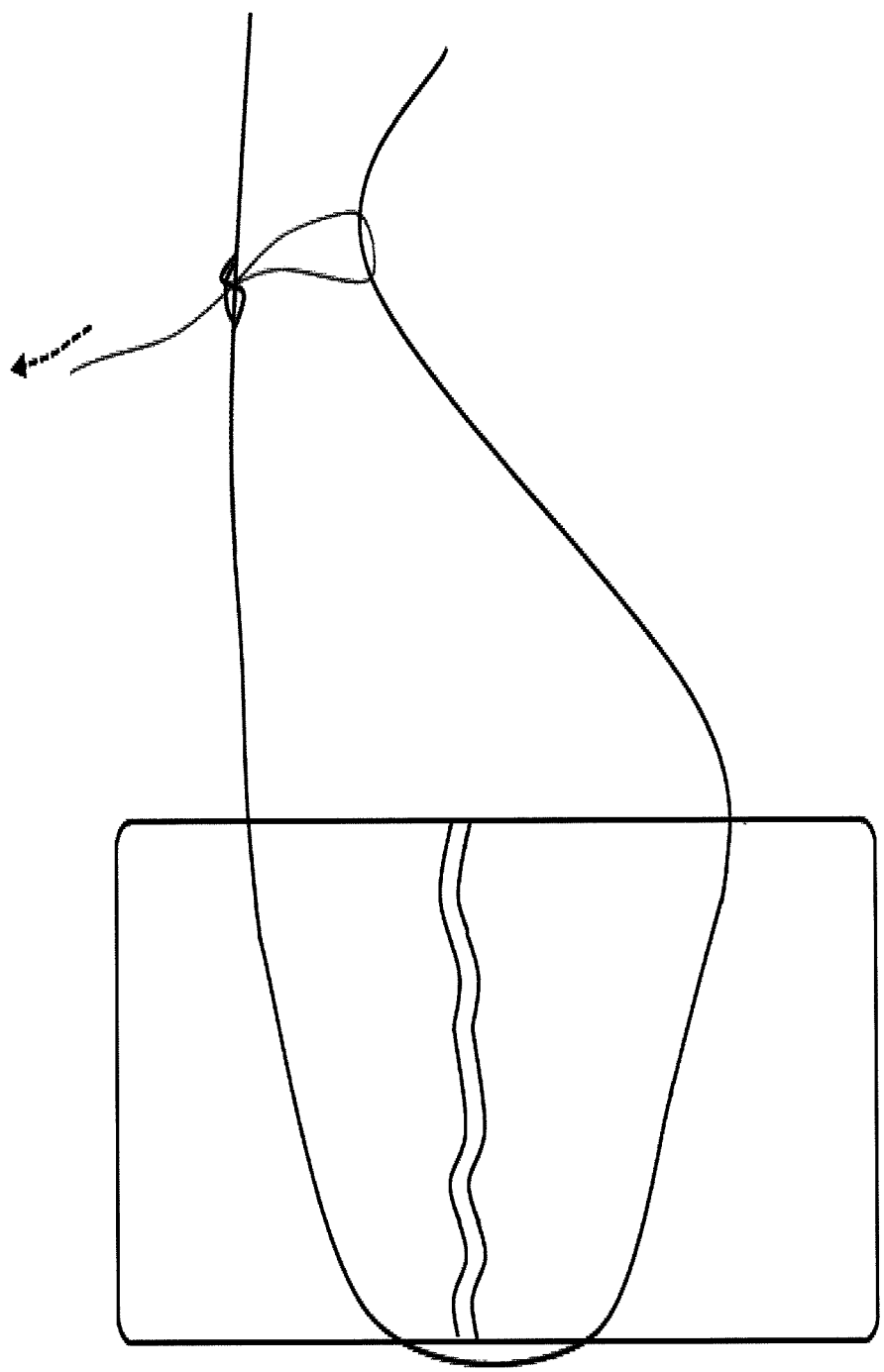
Figure 5G:
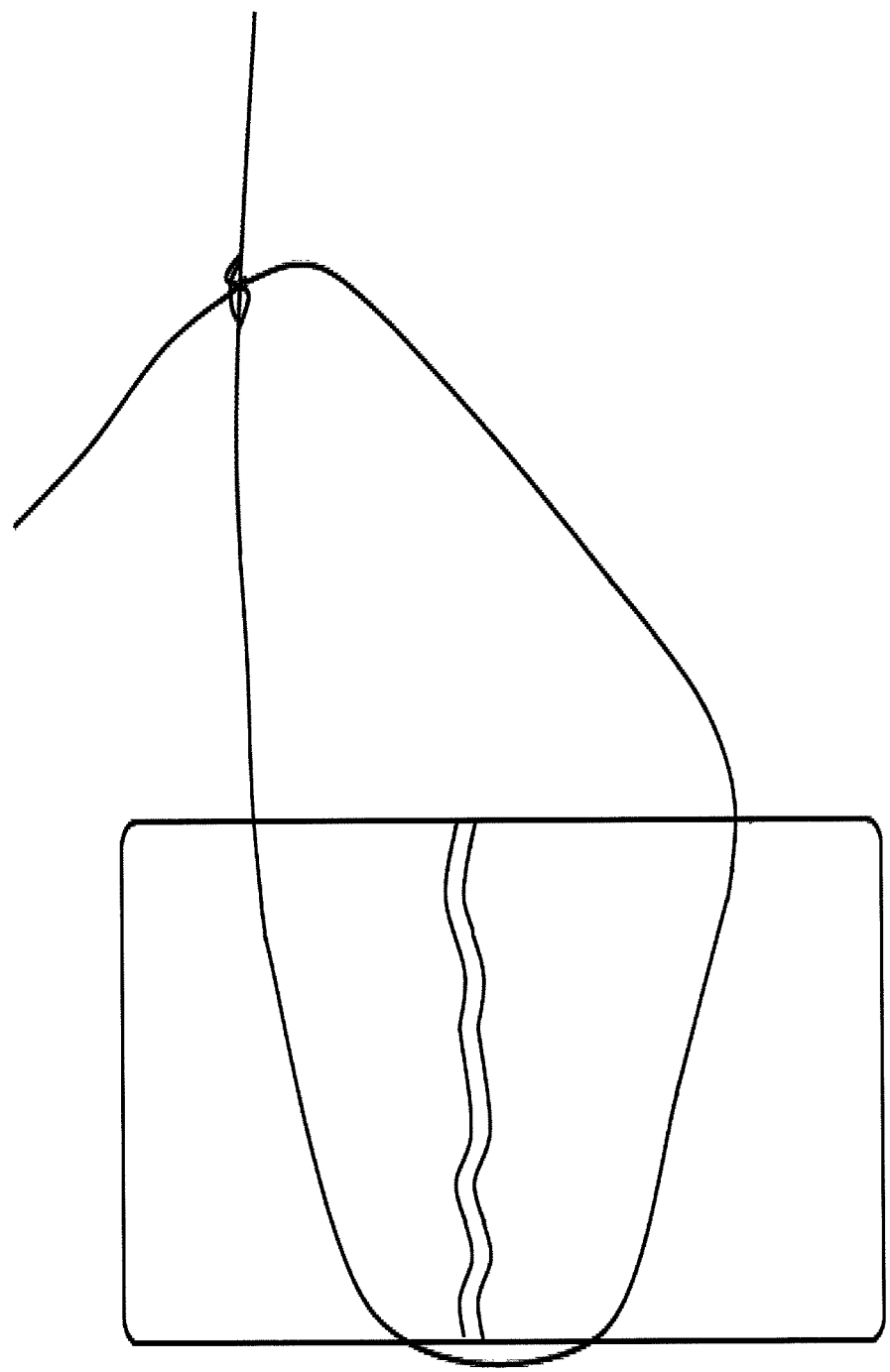
Figure 5H:
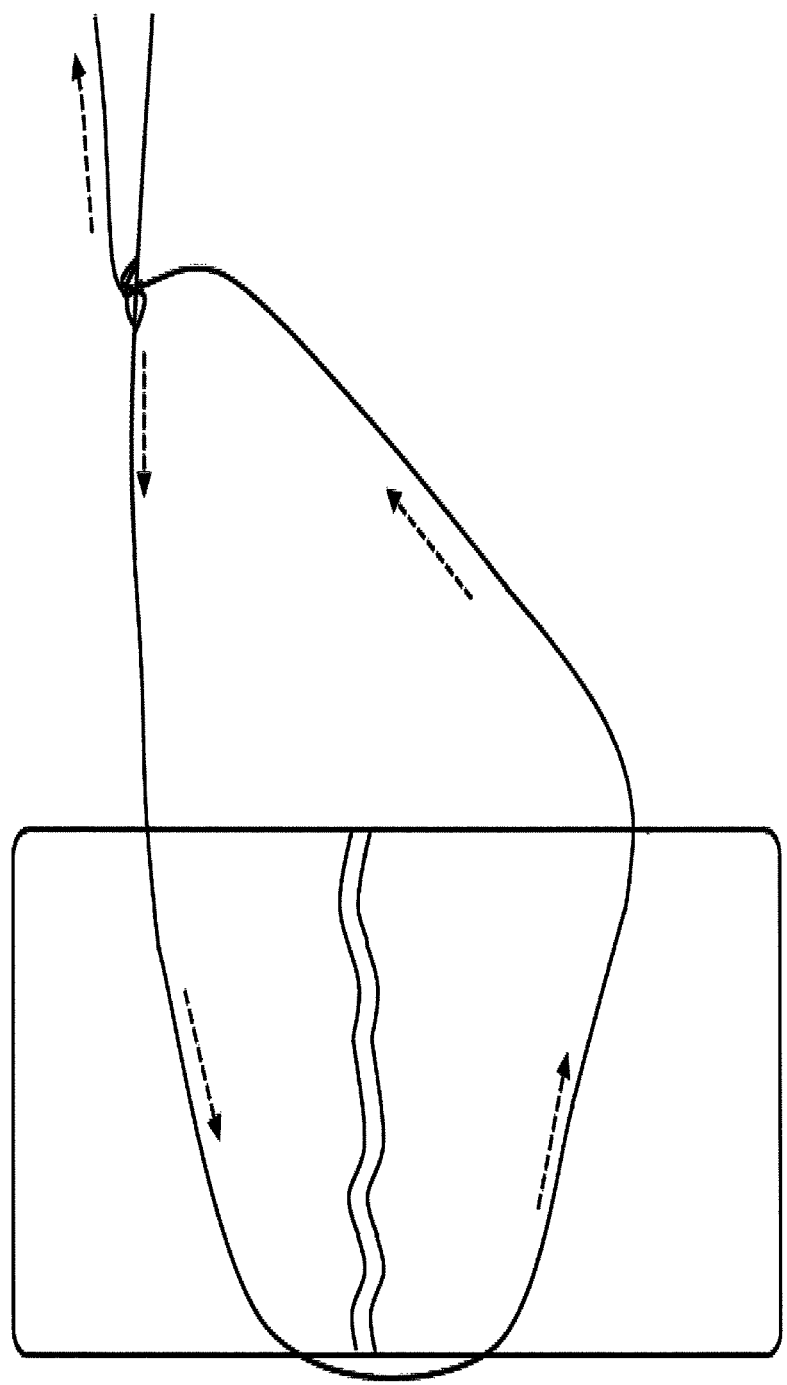
Figure 5I:
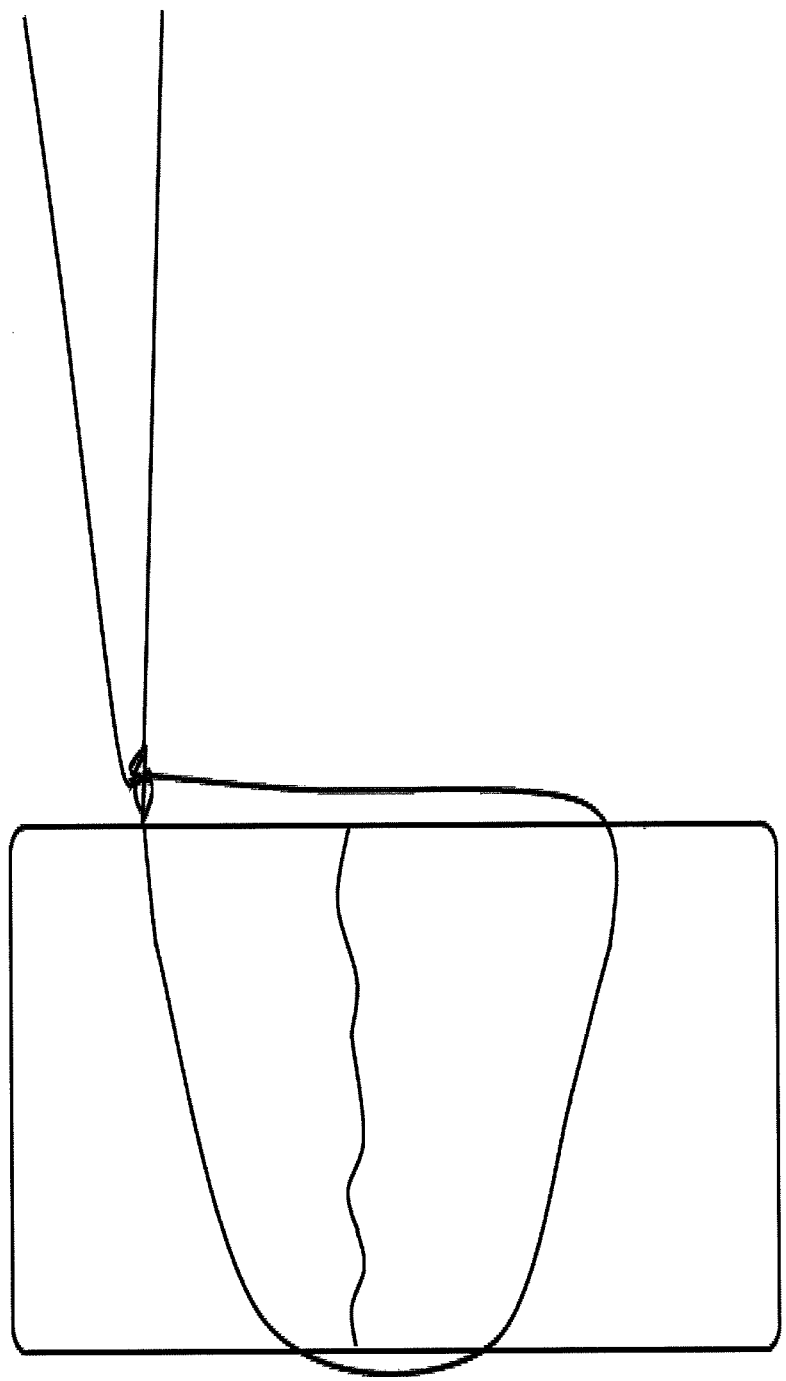
Figure 5J:
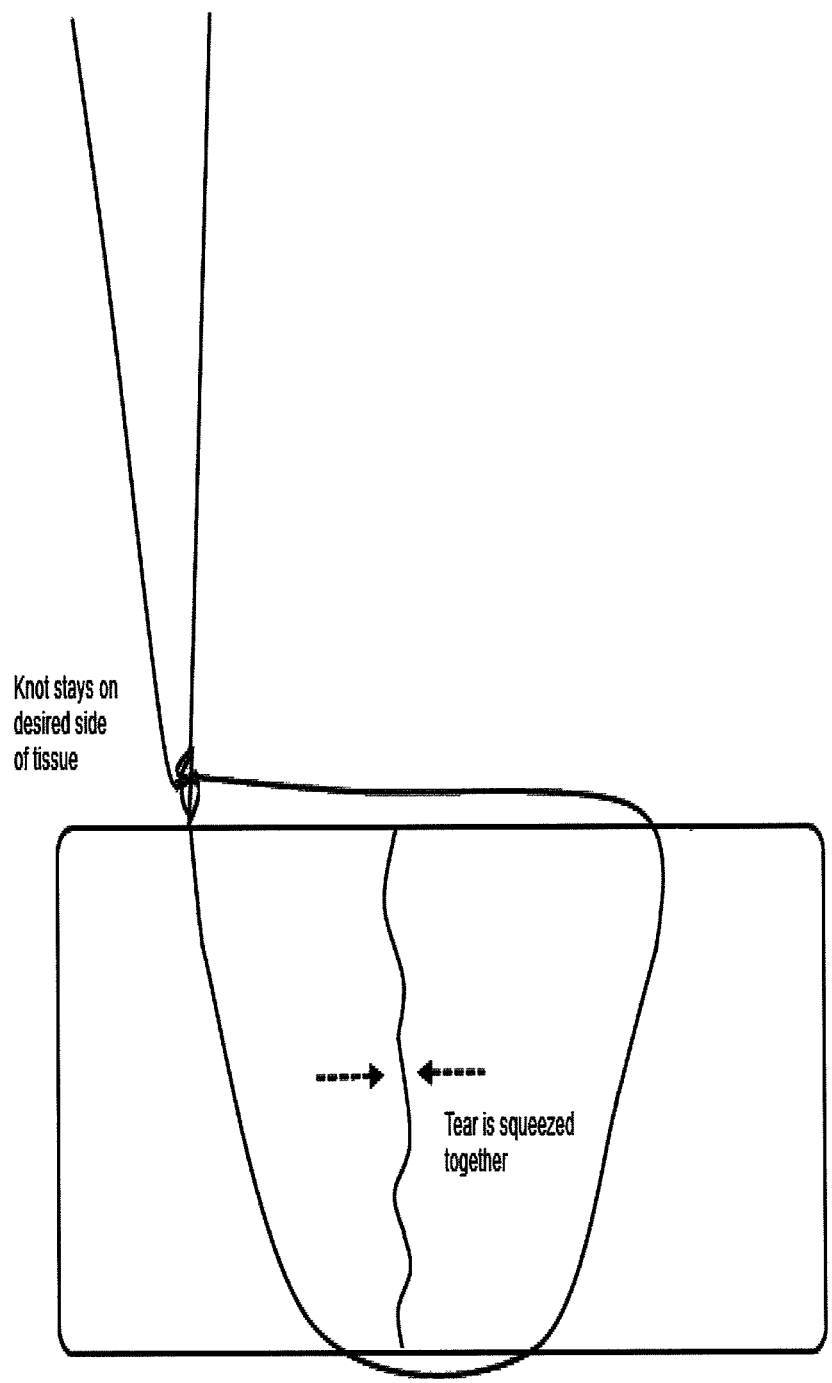

FIG. 5C illustrates one method of using a pre-tied knot to secure tissue. In this example, a suture including a pre-tied knot at one end has been passed through a region of tissue (around a tear in the tissue). As shown in FIG. 5D-5E, the end of the suture opposite from the pre-tied knot may be drawn through the loop of the leader snare. In FIG. 5F, the pull end of the leader snare may then be pulled (arrow) to draw the end of the suture through the knot body, as shown, until the suture has been completely pulled through the knot body, and the leader snare removed from the suture, as shown in FIG. 5G. In FIG. 5H, the arrows indicate that the suture may be cinched down onto the tissue by pulling on the end of the suture that has been pulled through the knot body, as shown in FIG. 5I, resulting in jointing the torn tissue. The tissue may be secured with whatever tightness is desired. The knot may be tightened by pulling on the opposite end of the suture as mentioned, above, and the loose suture ends may be cut off. This entire procedure may be performed percutaneously.

Figure 5K:
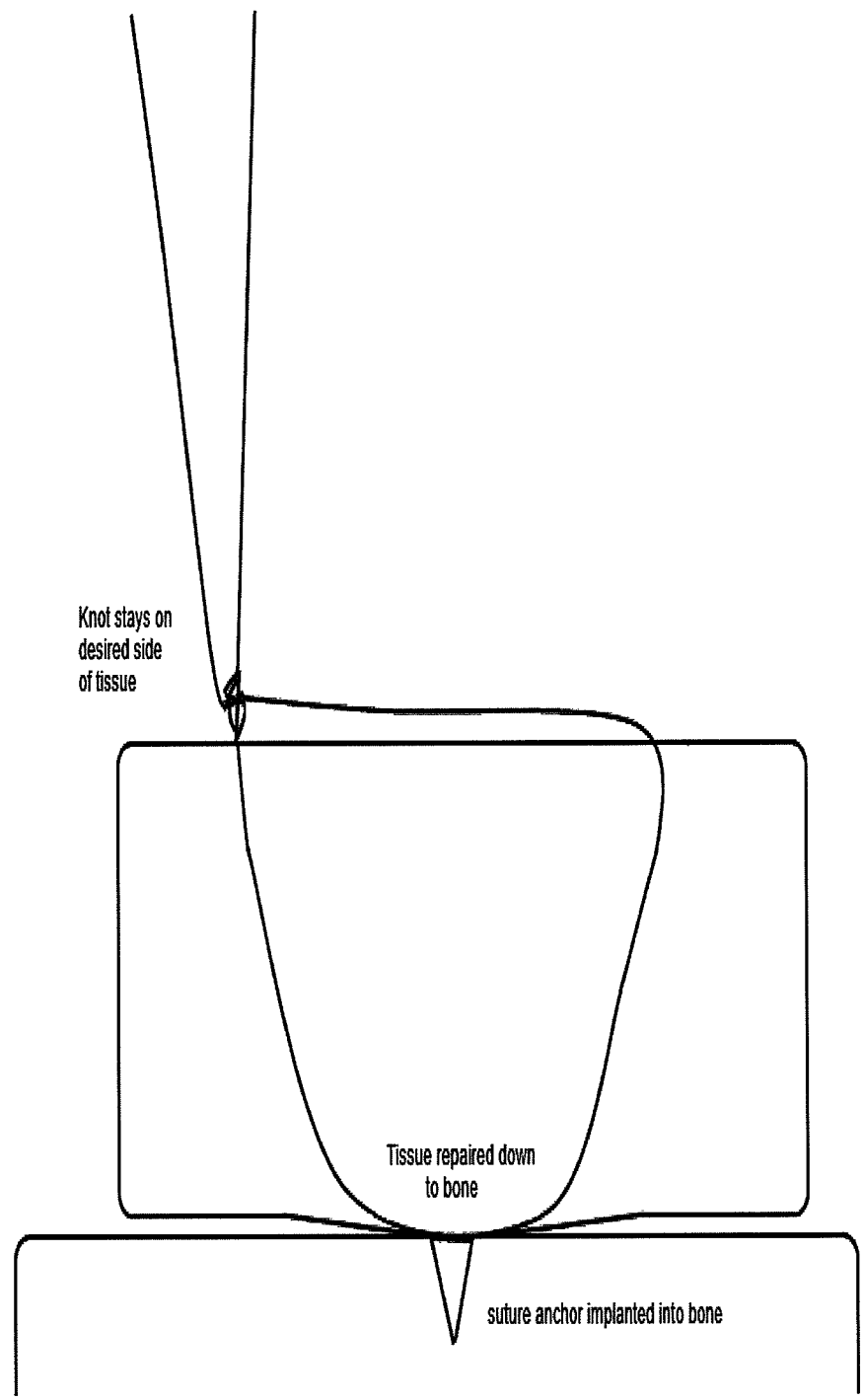

FIG. 5K shows a similar variation in which the suture is connected to an anchor that has been secured to the bone.

The examples shown above include pre-tied knots formed by looping a portion of a length of suture around itself one or more times to form the knot body which can be tightened over a leader snare and then used to secure a second region or length of suture through the knot body by cinching the knot body. In some variations the knot body forming a pre-tied knot is not formed (or not just formed) of a loop of suture length, but includes a suture trap region which permits only one-way movement of a length of suture through the knot body (e.g., suture trap).

Figure 6A:
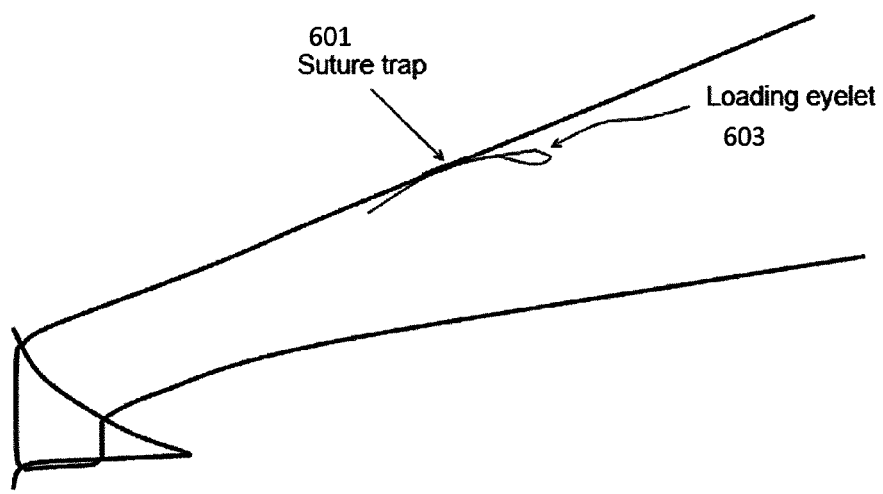
FIGS. 6A-6I illustrates another variation of a method for suturing tissue in which the pre-tied knot region is configured as a suture trap including a leader snare.

FIG. 6A illustrates one variation in which a knot body is formed of a suture trap that allows one-way passing (sliding) of a suture length. In this example, the suture trap 601 is coupled to the suture length and a leader snare 603 (which may also be referred to as a loading eyelet). The suture trap may be formed into the body of the suture, or it may be secured over or in the suture material. For example, the suture material may include a central lumen that may be opened at least partially to form a one-way channel for passage of a leader snare and/or suture length.

A one-way channel for a length of suture may be formed by including angled fibers, filaments, barbs, etc. within the channel that engage a suture to prevent its motion only when the suture is passing in a second direction; as the suture passes in a first direction the suture. For example, the suture trap may include internal barbs, cleats, rubber, braid, or other interference fit modifications that engage with a suture in a first direction, so that when suture is within, it cannot easily come out.

As illustrated above, a suture trap does not necessarily have to be a one-way channel for a suture length, but may be a constrictable channel that prevents withdrawal of a suture within the channel when under tension, but not when relaxed, similar to a woven finger-trap or finger-puzzle design. For example, a suture trap may be a modified section of a suture that acts as a 'finger trap' that constricts over a length of suture when under tension. The example shown above in FIGS. 3A-5K show variations such as this, in which the knot body is at least partially constricted around the leader snare.

As mentioned above a leader snare may be formed of a fine nitinol wire with a loop on the end or any string material.

Figure 6B:
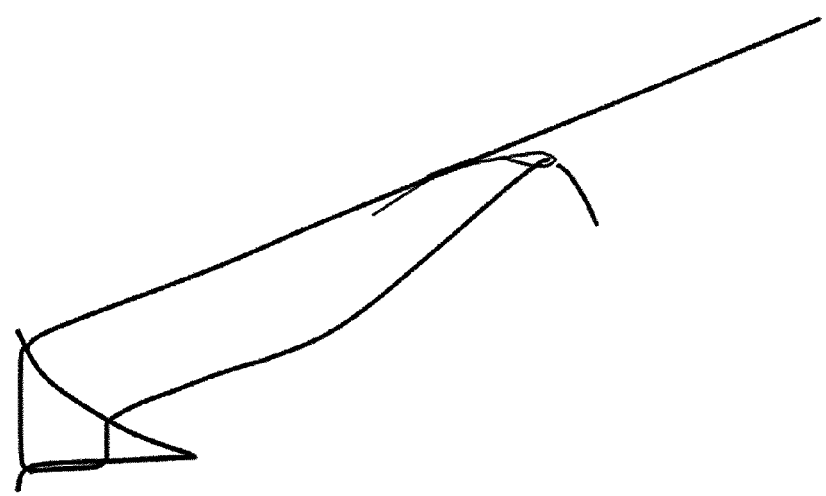
Figure 6C:
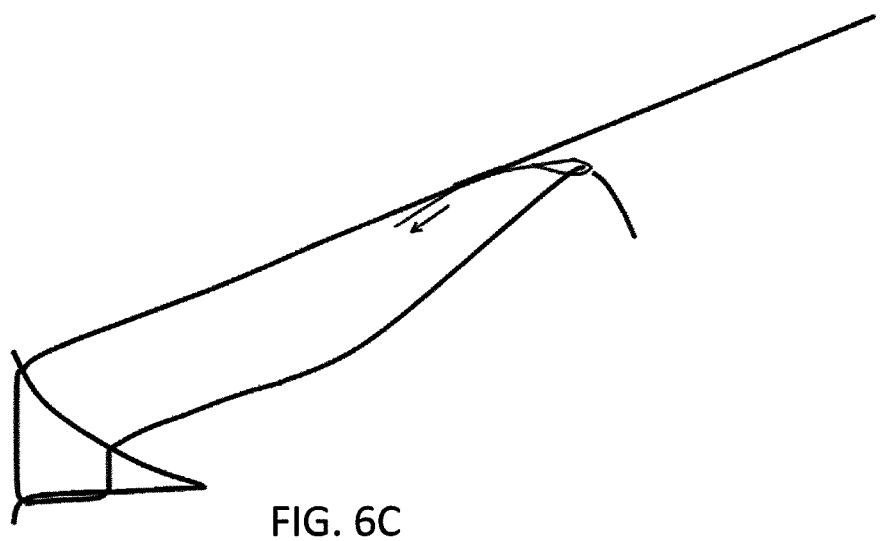
Figure 6D:
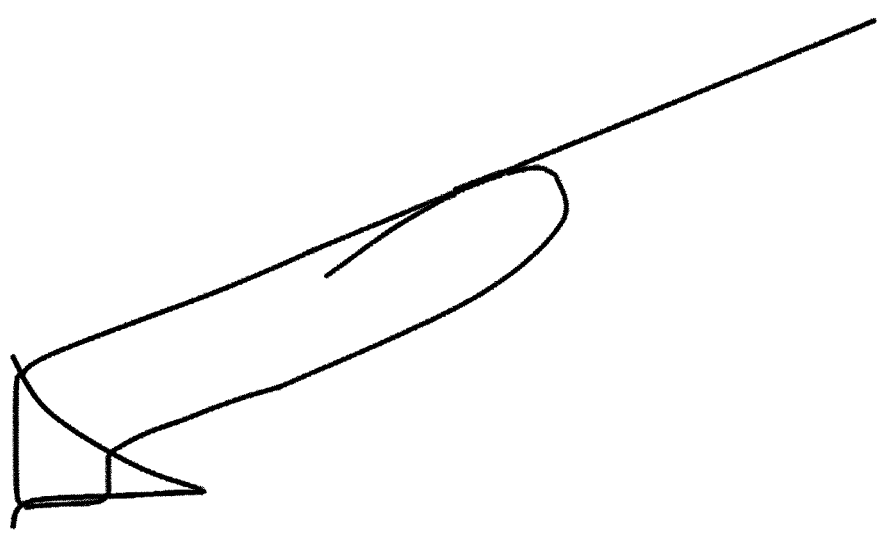

In FIG. 6A, the suture 600 includes a suture trap 601 connected to the suture. The suture body forms an enlarged region on the length of the suture, and a leader snare 603 passes through the suture trap. In some variations, the suture trap is formed from the suture length. For example, the suture length may be a woven material, and the suture trap (e.g., knot body) may be a passage into the woven body of the suture, along a length of a lumen within the woven body, and back out of the woven body. Once the suture has been passed through the tissue, as already shown in FIG. 6A, a second length of suture, in this case an opposite end of the suture passing through the tissue, may be passed through the eyelet of the leader snare, as shown in FIG. 6B. In FIG. 6C, the leader snare is then drawn through the knot body (suture trap), drawing the length of suture that has been passed through the eyelet of the leader snare. This length of suture material is thus left passing through the knot body, as shown in FIG. 6D.

As mentioned above, in some variations the suture trap variation of a knot body is configured to permit only sliding of the suture in a single direction (e.g., the direction of the arrow in FIG. 6C), so that the leader snare and the opposite suture length may be pulled to tighten or constrict the suture on the tissue, while preventing loosening of the loop formed by the suture. Thus, a suture strands may be secured within a suture trap in a one-way manner. For example, a suture trap may be formed as a twisting or braiding pathway within a channel through a region of the suture (defining the knot body), or a low-profile modified accessory may form the suture trap, which may be connected to the length of suture. Thus the knot body (suture trap) may include a pathway that will only allow a length of suture to be pulled into it and tightened in a one way manner. In some variations the suture trap may also include barbs within the tunnel in the suture at the 'suture trap' region, a rubbery material, glue or any interference fit or material could also be included. This may provide a knotless means of securing a suture. In some variations, as mentioned above, the knot body region (e.g., suture trap) may be passed through the tissue using a suture passer (e.g., following a needle hole created by a device, instrument or needle).

Figure 6E:
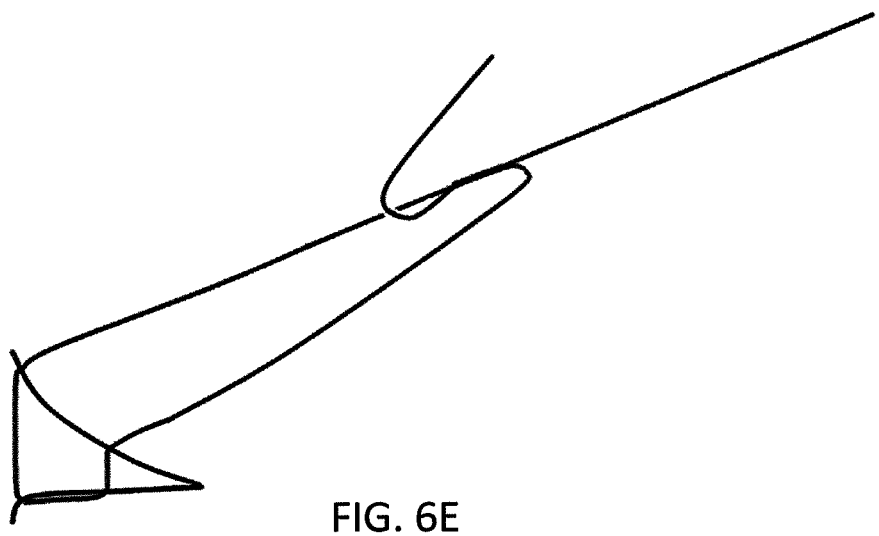
Figure 6F:
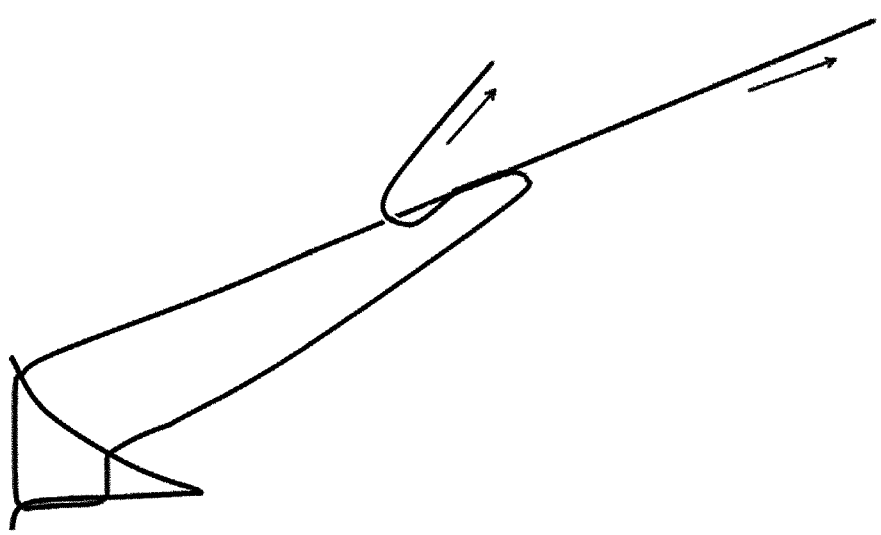
Figure 6G:
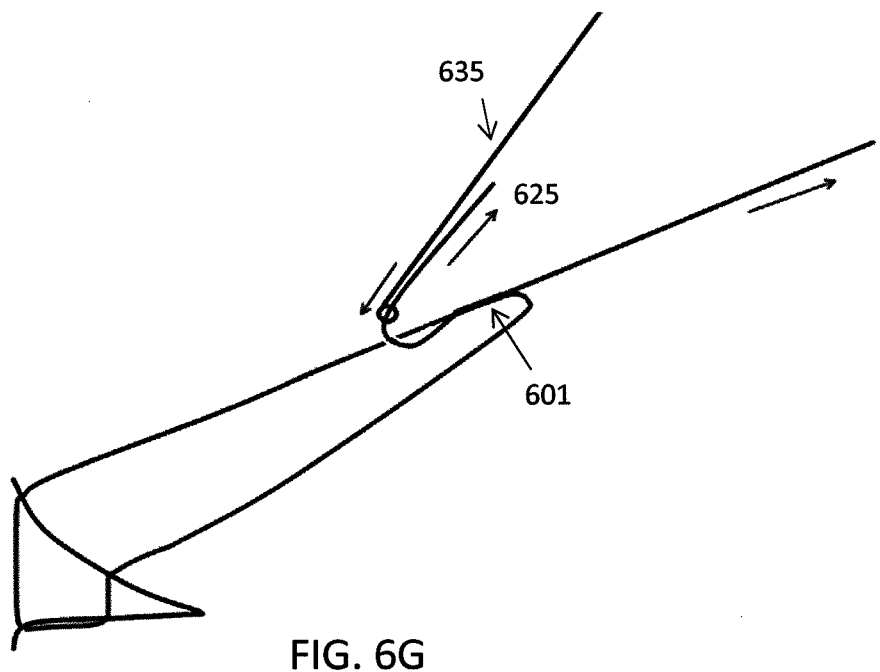
Figure 6H:
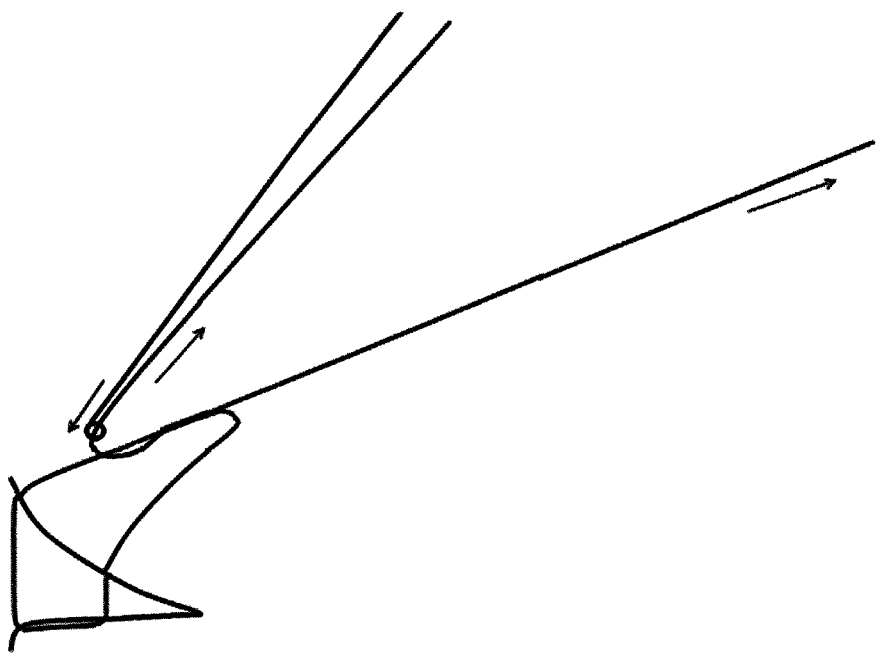
Figure 6I:
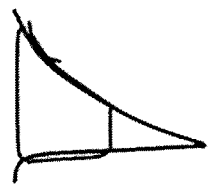

For example, in FIG. 6E the suture length that just passed through the suture trap may be pulled distally (as shown in FIG. 6F) to tighten the loop of suture around the tissue. In FIGS. 6G and 6H the distal end of the suture may be pulled 625, and the pre-tied knot (e.g., the suture trap region of the knot body) 601 may be pushed using a tool such as a knot pusher 635 to slide the trap region down to the tissue surface and tighten the loop of suture. FIG. 6I shows the completed loop tied around the tissue.

In any of the variations described herein, a knot pusher may be used to assist in tying or knotting the suture. In general, the knot pusher may be used to push a pre-tied knot body down the leg or length of suture (while holding the leg or length taut); once pushed to the tissue near where it is to be secured, the second length or leg of suture may be pulled to tighten the knot.

Figure 6J:
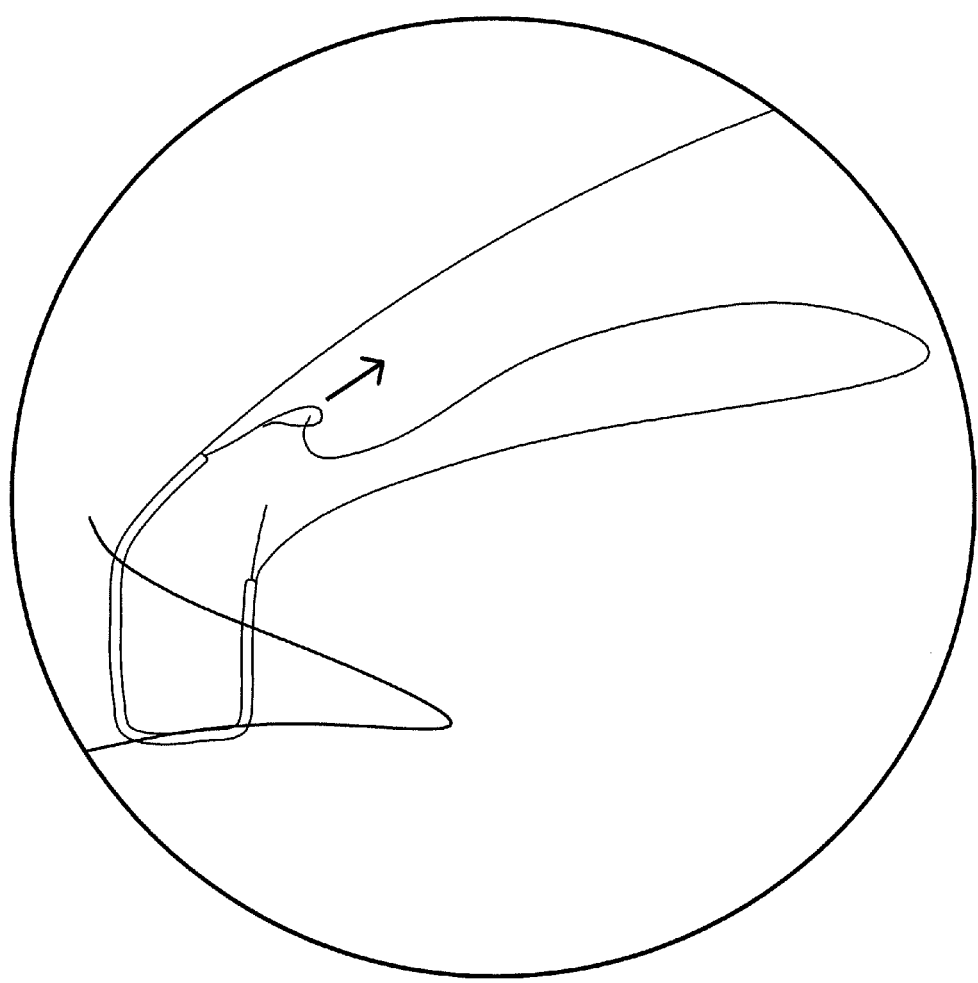
FIG. 6J shows another variation of a suture trap and leader snare for forming pre-tied knot with a suture.

A pre-tied knot may be any appropriate length. For example, a knot body of a pre-tied knot may be short (e.g., a few loops of suture, as described above), or it may be long. FIG. 6J shows one variation of a pre-tied knot body, configured as a suture trap, that is very long, and that has been passed through the tissue. In this example, as in FIGS. 6A-6I, the exemplary tissue is shown as knee meniscus, though these pre-tied knots may be used with any appropriate tissue. Passing the entire suture trap/knot body through the tissue in this manner may provide a very strong loop.

Any of the pre-tied knots described above may be pre-packaged within a suture anchor, or loadable into a suture anchor, for use in, as a non-limiting example, rotator cuff repair or labral repair in the shoulder, hip or any soft tissue that needs to be anchored to bone.

Although the description above is broken into parts and includes specific examples of variations of pre-tied knots, any of the features or elements described in any particular example or section may be incorporated into any of the other embodiments.

Pre-tied knots may also be used to suture tissue in another manner as described below. In particular, pre-tied knots may be used by the suture passer to help coordinate passage of the pre-tied knot and suture through the tissue.

Figure 7C:
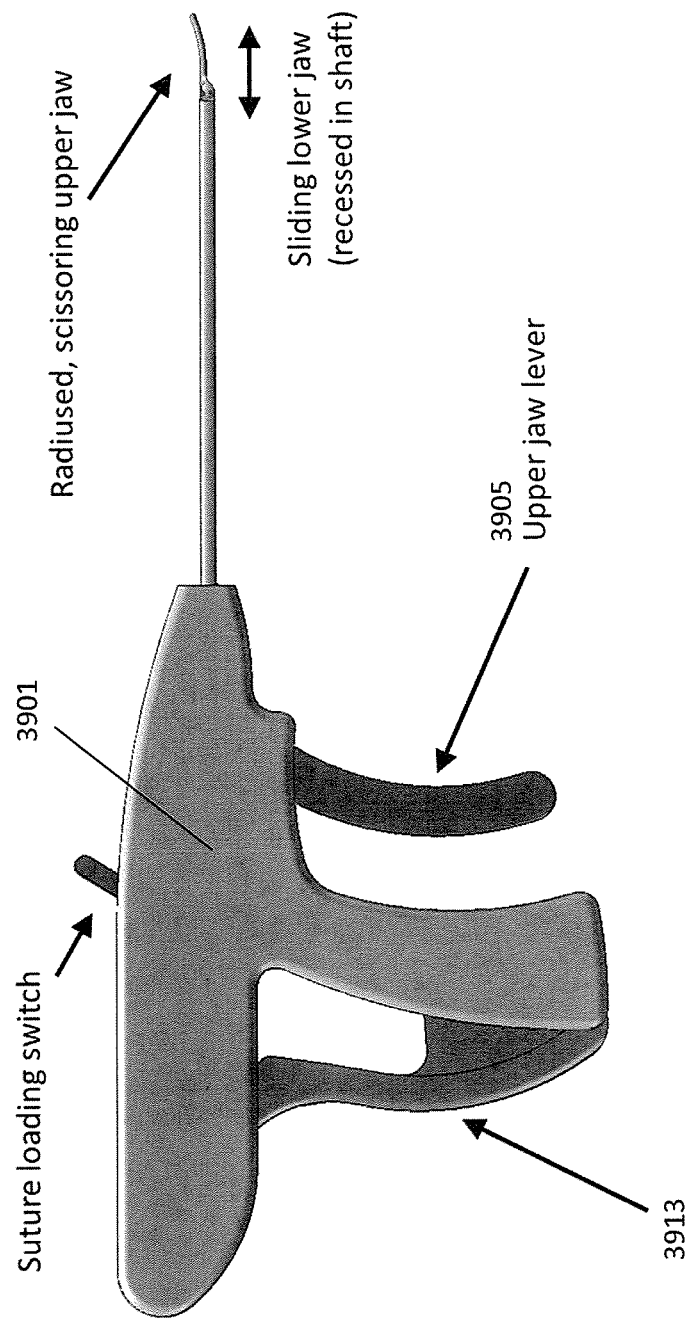

FIGS. 7A-7C illustrate one variation of a suture passer that may be used to place a suture having a pre-tied knot, as described above. Further, a suture passer such as the suture passer shown in FIGS. 7A-7C may also be adapted to suture tissue using one or more lengths of suture that includes a knot, so that the knot is passed through the tissue by the suture passer.

The suture passer of FIGS. 7A-7C has a tissue penetrator that extends distally from a distal opening in the upper jaw. The tissue penetrator travels in a sigmoidal path from the lower to upper jaw. In this variation, two lengths of a suture (including two lengths of the same suture, e.g., two ends of the same suture) can be loaded into the lower jaw and sequentially passed from the lower jaw, through different regions of the tissue and retained in the upper jaw, to pass a length of suture through the tissue. The suture passer show in FIGS. 7A-7C is also configured so that the upper jaw member can pivot to assume a different angle relative to the elongate body of the device, and the lower jaw member is axially extendable distally from the distal end of the elongate member to form a distal-facing mouth with the upper jaw member. The proximal handle includes a plurality of controls for controlling the pivoting of the upper jaw member, the axial sliding of the lower jaw member, and the extension/retraction of the tissue penetrator from the lower jaw member.

FIG. 7B shows the device of FIG. 7A with the outer housing of the proximal handle 3901 removed, revealing some of the connections between the controls and the device. In FIG. 7B, the distal most control 3905, the proximal handle is configured as a trigger or lever that controls the motion of the upper jaw member ("upper jaw control"). The upper jaw control may be pulled to reduce the angle of the upper jaw relative to the long axis of the elongate member 3907. In this variation the upper jaw control is pinned and allowed to drive a tendon in the elongate member distally when compressed to drive the upper jaw down (reducing the angle between the upper jaw and the long axis of the elongate member). This pivoting motion may also be referred to as scissoring (scissoring motion).

A distal control 3913 is also configured as a lever or trigger, and may be squeezed or otherwise actuated to extend and/or retract the lower jaw to form a distal-facing mouth with the upper jaw, as shown in FIGS. 7A-7B. In some variations the control is further configured to control deployment of the tissue penetrator in the sigmoidal path. For example, in some variations squeezing the distal control after completely extending the lower jaw may deploy the tissue penetrator from the lower to the upper jaw so that the distal end of the tissue penetrator extends out of the upper jaw. As it extends between the upper and lower jaw, the tissue penetrator may carry a first length (bight) of suture through the tissue. Upon reaching the opposite jaw member, the suture may be removed from the tissue penetrator and held (e.g., by a stripper) in the upper jaw. Upon release of the distal control, the tissue penetrator may withdraw back into the lower jaw. Actuating (e.g., squeezing) the distal control 3913 again may result in the extending the tissue penetrator (along with any second length of suture) back through the tissue from the lower jaw to the upper jaw, where the second length of suture can be retained. Alternately, in some variations, the controls (e.g., to control motion of the upper and/or lower jaw) may be separate from each other, and/or from extending/withdrawing the tissue penetrator. Additional controls may also be included in the proximal handle, include a suture loading control (e.g., switch, toggle, etc.) for loading and/or tensioning the suture within the lower jaw member.

FIGS. 8A-8D show an enlarged view of the distal end of the device of FIGS. 7A-7C. For example, in FIGS. 8A and 8B the upper jaw 4003 is thin and slightly radiused (e.g., curved), and is hinged to the elongate shaft region of the device. The upper jaw is also connected to a control (handle, etc.) on the proximal handle by a push/pull member (tendon, wire, rod, etc.), allowing adjustment of the angle of the upper jaw member relative to the elongate member.

Figure 8A:
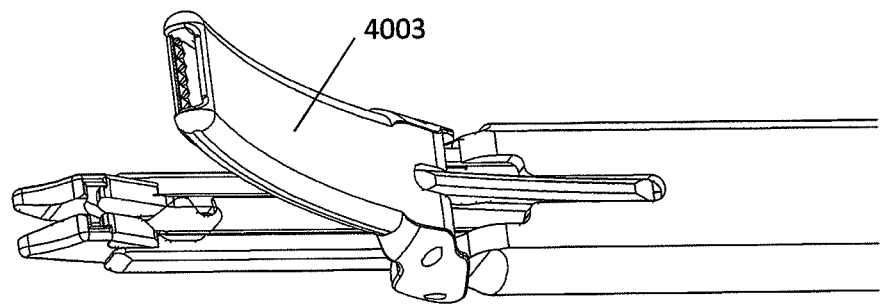
FIGS. 8A, 8B, and 8D show top and two side perspective views, respectively of the distal end of the suture passer shown in FIG. 7A.
Figure 8B:
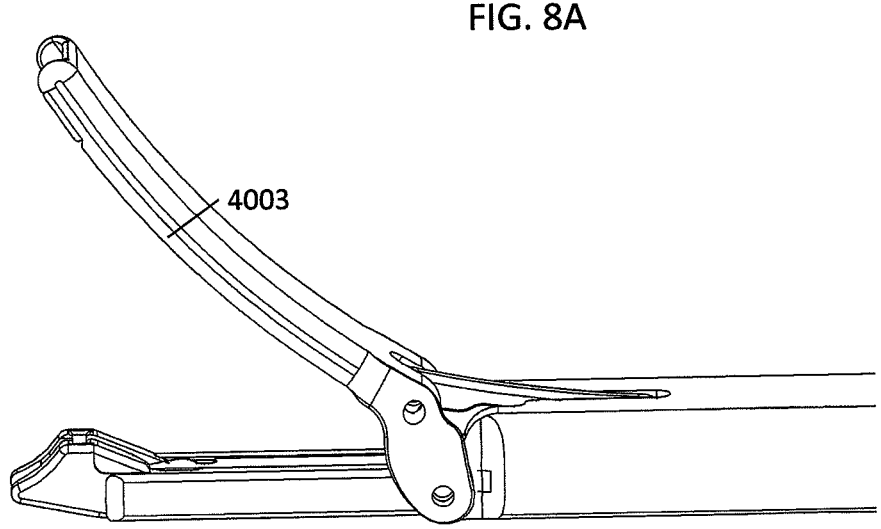
Figure 8C:
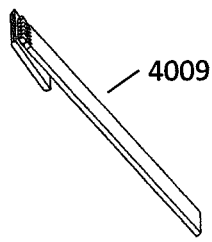
FIG. 8C illustrates the arrangement of the tissue penetrator and suture stripper in the distal end region of the suture passer of FIG. 7A.
Figure 8C:
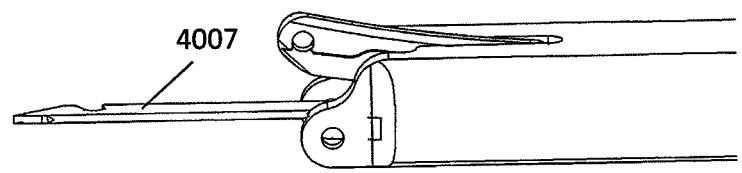
Figure 8D:
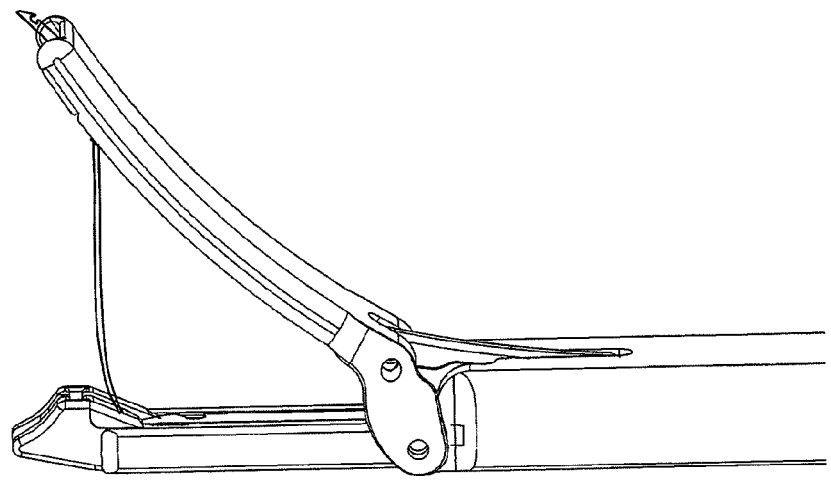
Figure 10A:
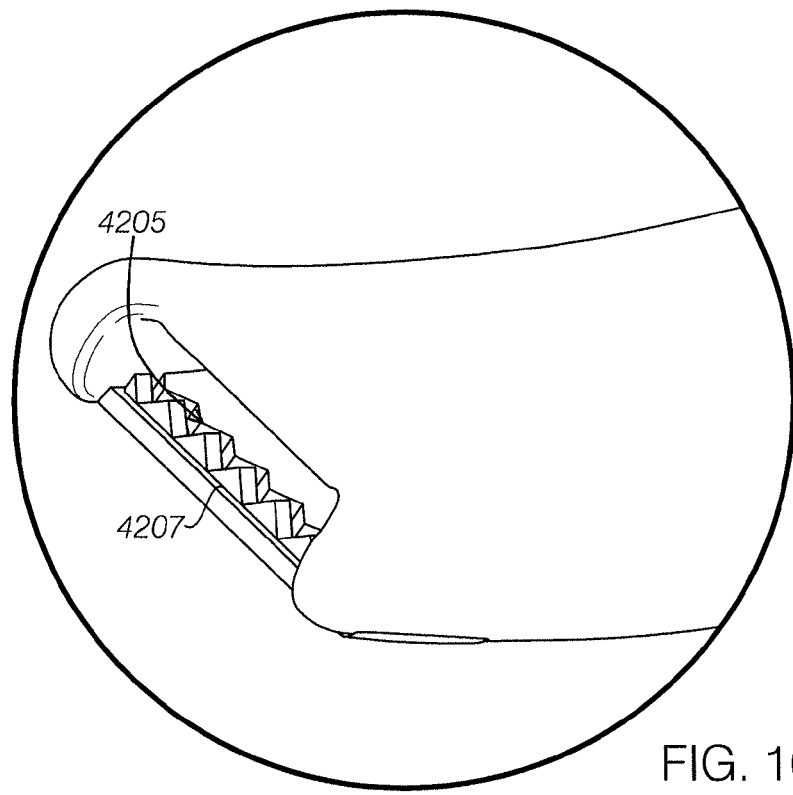
FIGS. 10A and 10B show side perspective views of the distal end region of a jaw member including a suture stripper.
Figure 10B:
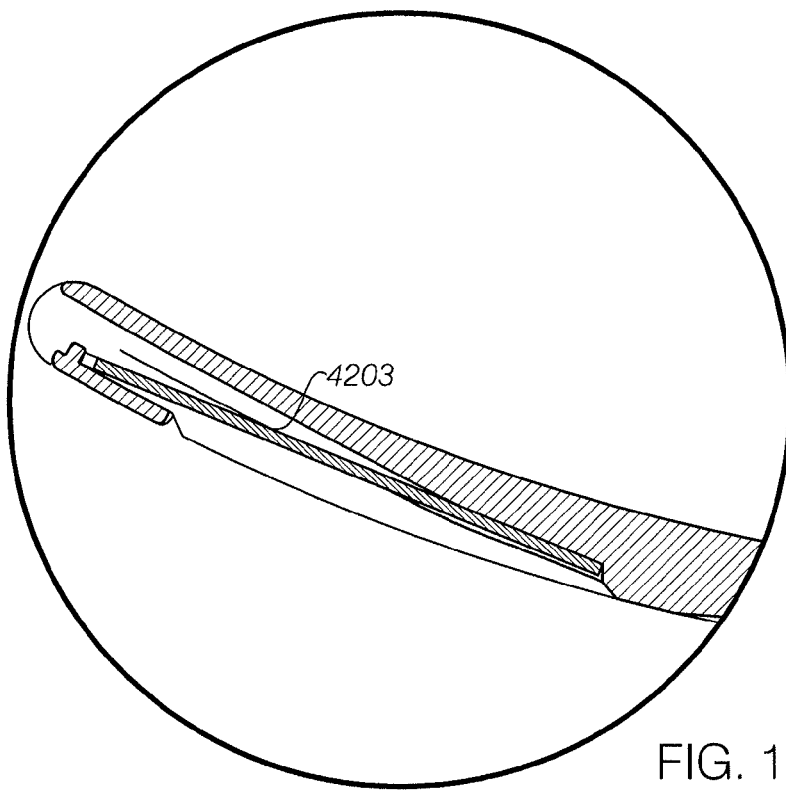

In FIG. 8C, the upper and lower jaw members have been removed from the distal end of the device shown in FIG. 8B, revealing the tissue penetrator 4007 within the lower jaw and the stripper 4009 in the upper jaw. FIG. 8D shows the distal end of the device of FIG. 8B after the tissue penetrator has been extended across the distal-facing mouth. FIGS. 10A and 10B illustrate one variation of an upper jaw region having a suture stripper. In FIG. 10A, the suture stripper is visible from the distal opening at the distal end of the jaw member. In this example, the stripper includes a stripper plate 4203 with a saw-toothed edge 4205. The jaw member also includes a receiver region for the stripper plate having a sawtooth edge 4207.

Figure 9A:
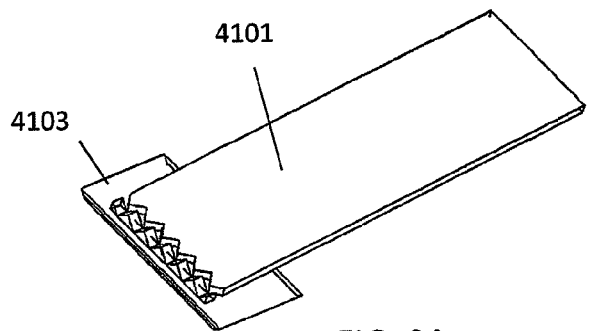
FIGS. 9A-9C show a suture stripper including a stripper plate (FIG. 9B) and base (FIG. 9C).
Figure 9C:
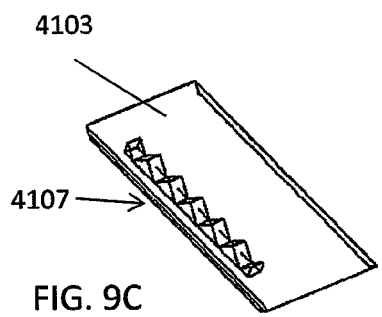
Figure 9B:
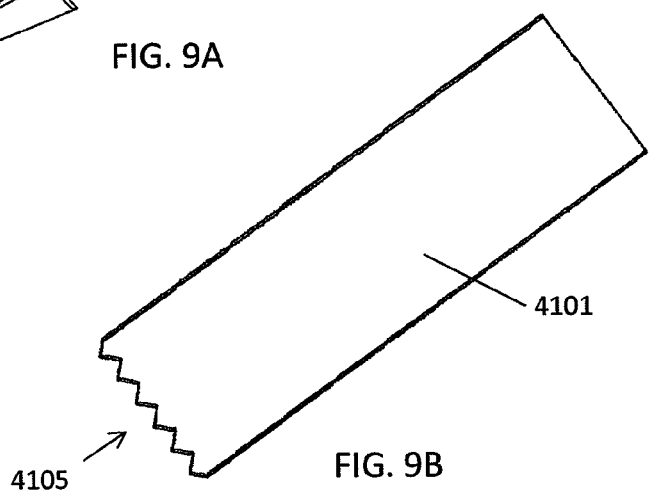

FIGS. 9A-9C show greater detail on one variation of a suture stripper that may be used. This variation is the same as the variation shown in FIGS. 10A and 10B. Although the examples provided herein show the suture stripper in the upper jaw member, in some variations a suture stripper may be present on the lower jaw member (e.g., where the tissue penetrator is configured to pass a length of suture from the upper jaw to the lower jaw). In FIG. 9A, the stripper includes a flexible plate 4101 that is fixed at the proximal end (e.g. to the upper jaw member), and pressed against a receiving plate 4103 at the distal end 4105. In some variations the receiver is not a separate receiving plate, but merely a region of the jaw member. Either or both the suture stripper plate 4101 and the receiver 4103 may include an edge that is adapted to catch the suture. In FIGS. 9A-9C, both the plate 4101 and receiver 4103 include edges having teeth 4105 and 4107. In this example the teeth are saw-tooth structures that are adjacent (or abutting) in the upper jaw member. The tissue penetrator may pass between the plate 4101 and the receiver 4103 by deflecting the plate 4101; as the end of the tissue penetrator passes the edges 4105 and 4107, a length of suture held by the tissue penetrator may be caught by the stripper and held between the plate and receiver as the tissue penetrator is withdrawn.

In practice, a suture passer having a distally-extending tissue penetrator (including a pre-tied knot) may be used to repair a tissue such as the meniscus of the knee. FIGS. 11A-11F illustrate one method of repairing a torn meniscus using a suture passer such as the one shown above in FIGS. 7A-7C.

The devices and methods described herein may be used to pass a loop of suture and specifically, may be used to form a vertical or horizontal stitch to repair tissue. When repairing the meniscus, a vertical stitch typically provides the strongest repair with the least amount of displacement relative to horizontal stitches or other "all-inside" approaches. The devices and methods described herein may also be referred to as "all-inside" devices and meniscal repair techniques allow the meniscus to be sutured directly. The suture passers described herein may place a fully-circumferential, vertical stitch around meniscal tears. This stitch may provide uniform compression along the entire height of the meniscus and maintain coaptation of the tear at both the inferior and superior meniscal surfaces. Further, because of the jaw and needle configuration, the distal extending tissue penetrator does not penetrate the capsule wall, reducing or eliminating risk to posterior neurovascular structures. These features may allow a greater healing response due to complete tissue coaptation along the entire substance of the tear, improved clinical outcomes due to the greater healing response and to the anatomic reduction and fixation of the meniscus tear, may avoid scalloping or puckering of the meniscus, and may result in less extrusion or peripheralization of the meniscus caused by over-tensioning of suture or hybrid tensioners to the capsule. These devices can also be used to treat radial, horizontal, flap, and other complex tears in addition to longitudinal tears.

In some variations, the suture passer devices described herein can be fired blindly where arthroscopy camera access is poor, as knee structures are protected from the needle path.

Returning now to FIGS. 7A-7C, as mentioned above, the device (e.g., in FIG. 7C) has a scissoring upper jaw that is curved (radiused). This curve may be configured to follow the radius of the femoral condyle. The lower jaw in this example is straight. The lower jaw may be recessed into the shaft, and may slide proximal-to-distal in order to slide under the meniscus along the tibial plateau after the upper jaw is in place along the superior surface of the meniscus. The lower jaw contains a flexible needle, which moves vertically from the lower to upper jaw.

Figure 11A:
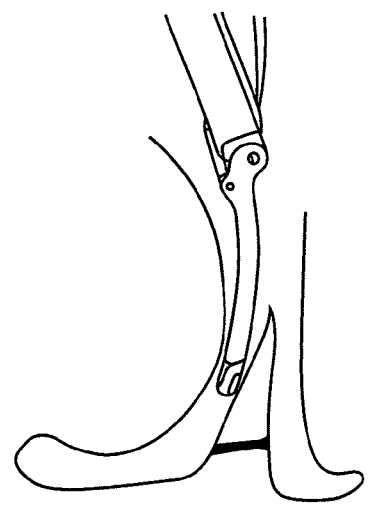

FIGS. 11A-11F illustrate one method of using a suture passer as illustrated in FIGS. 7A-7C to repair a torn meniscus. As mentioned, the upper jaw of the suture passer may be positioned between the superior surface of the meniscus and the femoral condyle, as shown in FIG. 11A. The thin and slightly curved upper jaw follows the curve of the femoral condyle. The lower jaw is retracted within the elongate body, and has been loaded with two lengths of suture (from end regions of the same suture).

Figure 11B:
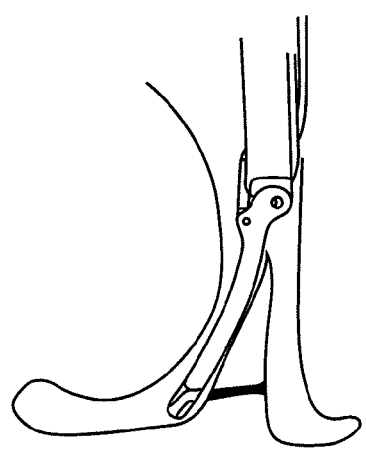
Figure 11C:
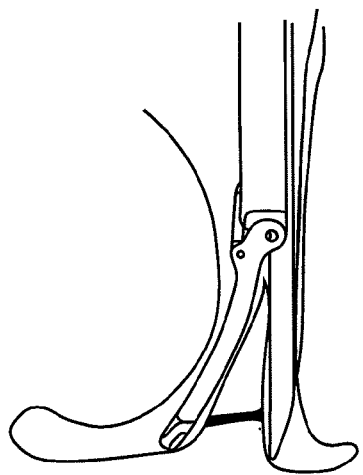
Figure 11D:
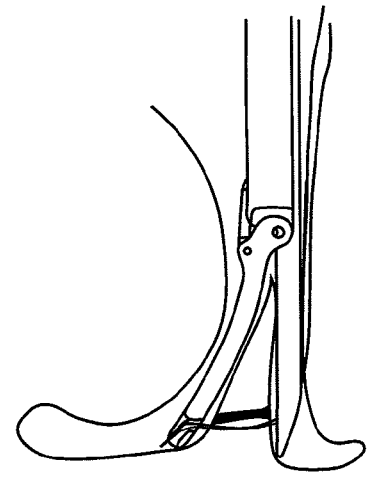
Figure 11E:
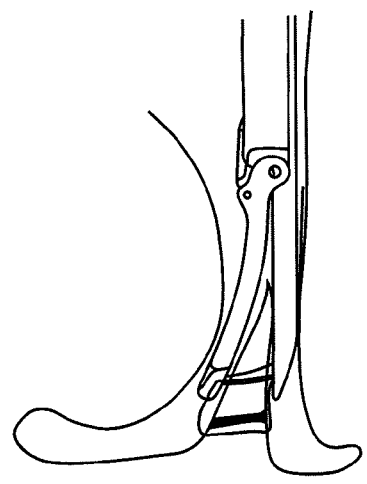

In FIG. 11B, the lower arm is initially retracted; after the upper arm is positioned adjacent to the torn region to be sutured, the lower jaw is extended underneath the meniscus, as shown in FIG. 11C. The sliding lower jaw may more easily accommodate the spatial constraints of the knee than a fixed or scissoring lower jaw. As described above, the lower jaw member in this exemplary device houses a flexible tissue penetrator (e.g., needle) that can be advanced through the meniscus to deliver suture bights from the lower jaw to the upper jaw. Once the device is in position distal to a longitudinal tear or adjacent to a radial tear, the tissue penetrator is advanced from the lower arm to the upper arm. The tissue penetrator pulls one end of the suture strand from the lower jaw to the upper jaw, where it is retained. The tissue penetrator does not pass through the upper jaw, so the femoral condyle remains protected; instead the tissue penetrator extends from a distal opening in the upper jaw, as shown in FIG. 11D. The tissue penetrator is withdrawn into the lower jaw where it engages the opposite end of the suture strand. The device is then repositioned for the second bight, either proximal of a longitudinal tear (see FIG. 11E) or to the other side of a radial tear (not shown in the example). Once in position, the tissue penetrator is advanced to deposit the remaining suture bight in the upper jaw, as shown in FIG. 11E.

Figure 11F:
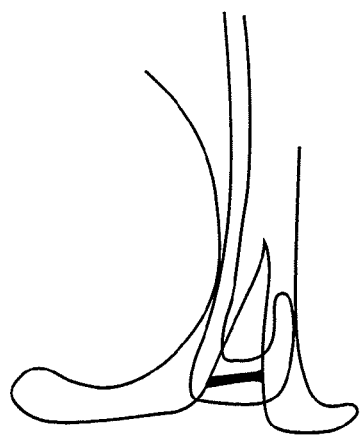
Figure 11G:
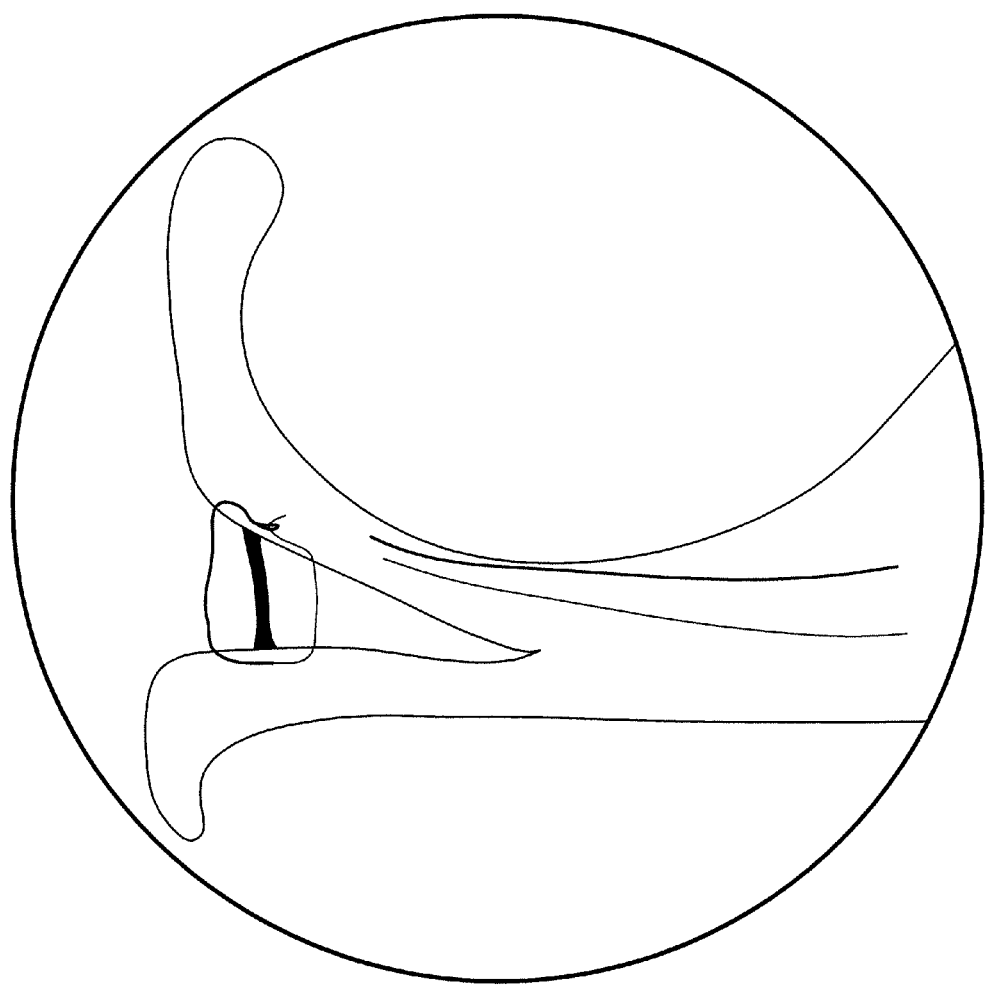

The tissue penetrator can then be brought back into the lower jaw, the lower jaw retracted, and the device may be withdrawn from the knee, leaving a suture loop surrounding the tear, as shown in FIG. 11F, with both ends exiting on the femoral side. A surgeon may then tie and advance a sliding knot (or individual throws) percutaneously, and the loose ends cut, as shown in FIG. 11G. Since both suture-ends may be retrieved through the same track, a cannula is not required to prevent tissue bridging. This may result in a fully-circumferential, vertical stitch around the tear, as shown in FIG. 11G. This vertical stitch completely surrounds the meniscal tear, bringing the superior and inferior margins of the tear in apposition along with the meniscal area in between. FIG. 12A shows a perspective view of a portion of a meniscus repaired in this manner. FIGS. 12B and 12C illustrate how the device and methods described above may also be used to suture more complex meniscal tears, including those having a radial tear.

Figure 13A:
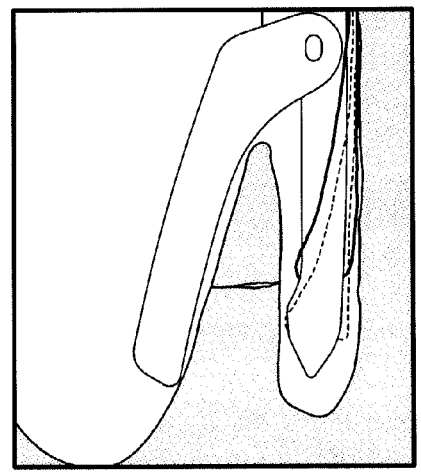
FIGS. 13A-13L show another illustrate of a method for suturing meniscal tissue similar to that shown in FIGS. 11A-11G.
Figure 13B:
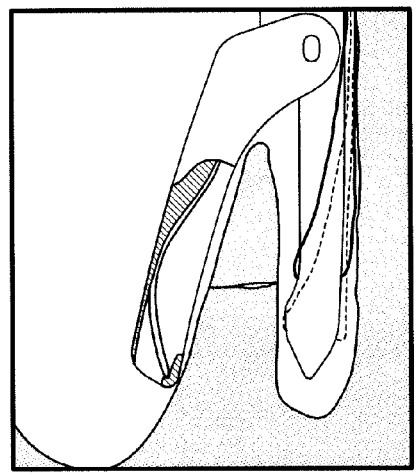
Figure 13C:
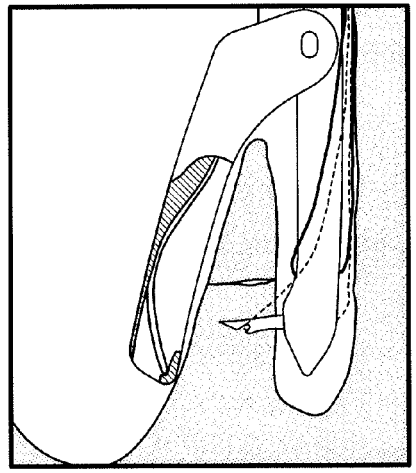
Figure 13D:
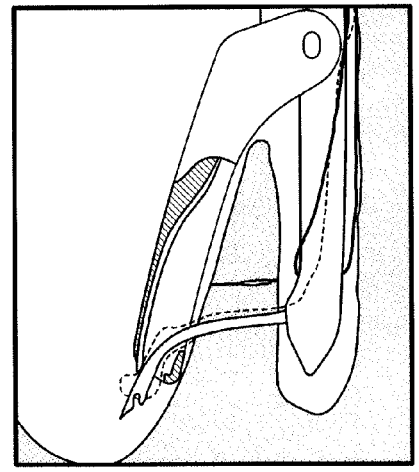
Figure 13E:
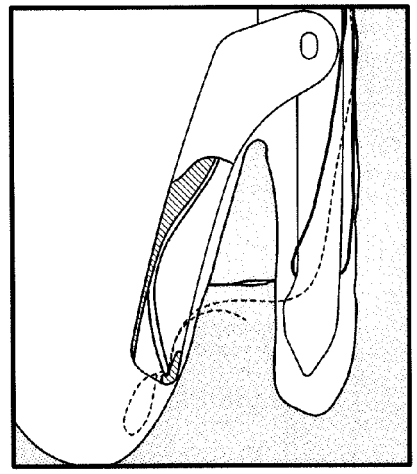

FIGS. 13A-13L illustrate another example of a method for suturing a torn meniscus by passing a loop of meniscus. As just described, the exemplary device shown in FIGS. 13A-13C may be used or other variations of the suture passer devices described herein may be used to suture a torn meniscus. In this example, two regions of a suture are initially loaded into the suture passer in the lower jaw. For example, the first length of suture may be loaded into the tissue penetrator and a second length of suture may be held in a holding region of the lower jaw; the lower jaw may be configured so that once the first length of suture has been passed into the upper jaw member and the tissue penetrator has been retracted, the second length of suture may be loaded into the tissue penetrator for passing through the tissue. In FIG. 13A, the ends of the suture are shown loaded into the lower jaw. In FIG. 13B and subsequent FIGS. 13C-13K, the upper jaw has been removed from the device shown in FIG. 13A to show the deflecting surface and suture stripper (a sheet of metal) in the upper jaw. In FIG. 13C, the tissue penetrator may then be extended from the lower jaw, carrying a length of suture, and pushed through the meniscus towards the upper jaw. The suture passer may then enter into the upper jaw and be deflected by the deflector region within the upper jaw so that it extends distally out of the upper jaw member, as shown in FIG. 13D. In this example, as the tissue penetrator pushes up into the upper jaw it pushes the stripper out of the way, allowing the suture to advance beyond the end of the stripper. In FIG. 13E, retracting the tissue penetrator leaves the suture held by the stripper in the upper jaw. The stripper places a downward force on the tissue penetrator as it retracts, this force strips the suture off of the tissue penetrator and then pins the suture length in the upper jaw.

Figure 13F:
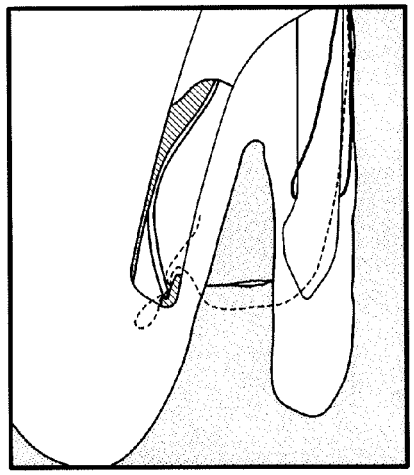
Figure 13G:
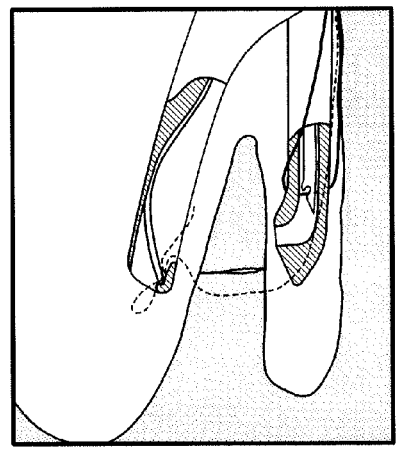

As shown in FIG. 13F, the device may then be repositioned to fire a second time. The device is moved to the second location. Moving the device does not dislodge the suture from the upper jaw, as it is secured by the stripper. Retracting the tissue penetrator into the lower jaw may cause the second end of the suture to be loaded into the tissue penetrator, as shown in FIG. 13G.

Figure 13H:
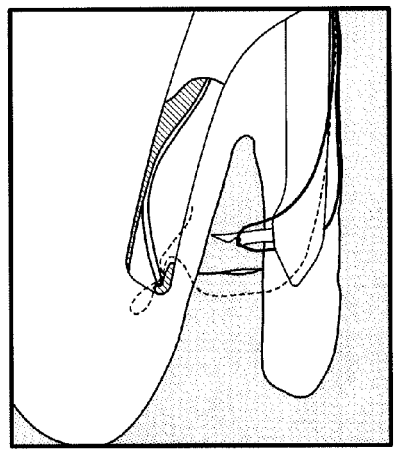
Figure 13I:
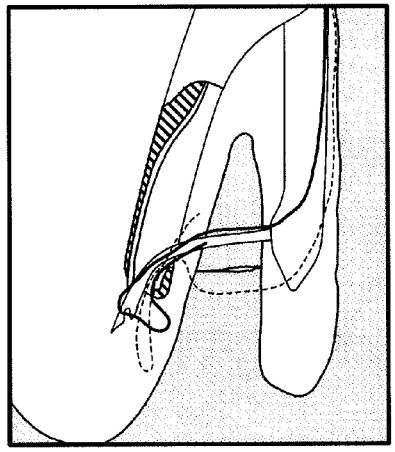
Figure 13J:
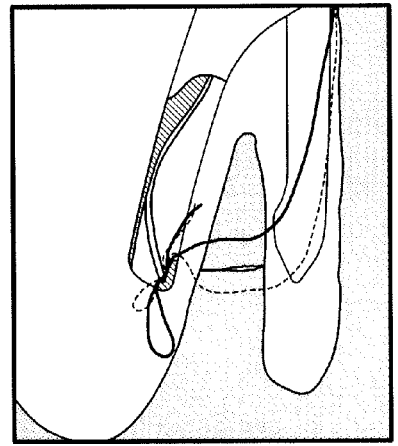
Figure 13K:
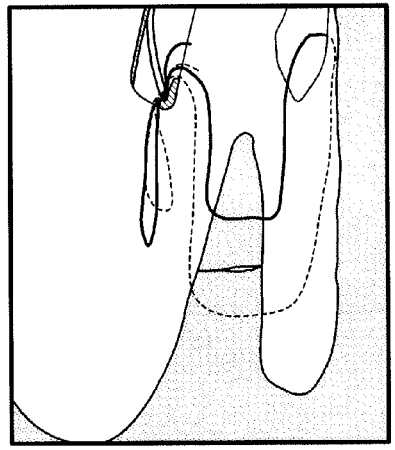
Figure 13L:
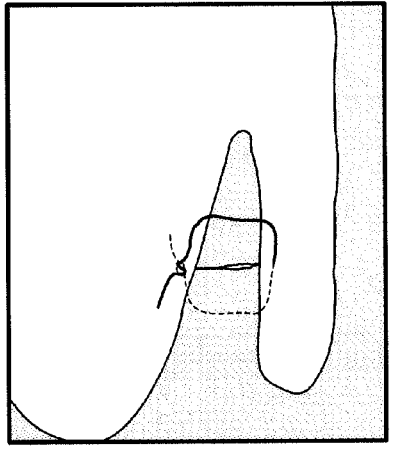

The tissue penetrator can then be extended back across the tissue from the second position on the opposite side of the meniscal tear, as shown in FIG. 13H. The tissue penetrator carries the second length of suture with it to the upper jaw, and past the stripper again, as shown in FIG. 13I. As before, withdrawing the tissue penetrator after extending it out of the distal end of the upper jaw so that the second length of suture extends beyond the stripper results in the stripper retaining the second length of suture along with the first length of suture, as shown in FIG. 13J. The device may then be retracted with both sutures pinned in the upper jaw, as shown in FIG. 13K. The device may be fully retraced, and the ends of the suture tied, as shown in FIG. 13L. As discussed above, the suture may be tied using a pre-tied knot. Thus, one or the other loop of suture lengths (bights) passed through the tissue as described above for FIGS. 13C/13D and 13H/13I may include a pre-tied knot that is passed with the length of suture.

Alternatively, in some variations a knot of suture may be passed through tissue using a suture passer as describe above in which a pre-tide knot is used to help secure the length of suture being passed to the device. For example, in some variations an end region of one or both (in variations in which two lengths of suture are being passed) lengths of suture are knotted, and this pre-tied knot may be passed through the tissue by the tissue penetrator. The pre-tied knot may or may not include a leader snare as described above. For example, in some variations two lengths of suture (from the same elongate suture) may be passed through a tissue; both lengths may be pre-knotted, however only one of the pre-tied knots may include a leader snare and be configured to allow another length of suture to be pulled through.

FIGS. 14A-14J illustrate a method of passing a suture (two length of suture in this example, though a single pass may also be performed) using a knot capture method in which the lengths of suture are knotted near their ends and the knots of suture are passed by a suture passer. In this example a plastic piece is used to represent tissue. Although these figures describe pre-knotted ends, in some variations the "knots" are formed by non-suture materials, or by means other than tying the suture. For example, as mentioned above in the general case, a "knot" may be formed exclusively from loops of suture, or it may be formed without looping the suture, and/or from non-suture material. For example, in FIGS. 14A-14J, the knots at the ends of the suture may be formed by heating the suture ends to create an enlarged region (e.g., a "mushroom head" feature), by crimping a metal piece that helps facilitate suture trapping, by creating an eye splice or eyelet in the ends of the suture which interact with the needle, etc. One or both knots in the suture may be formed in this manner. In general, such knots are formed by an enlarged region relative to the rest of the length of the suture.

Figure 14A:
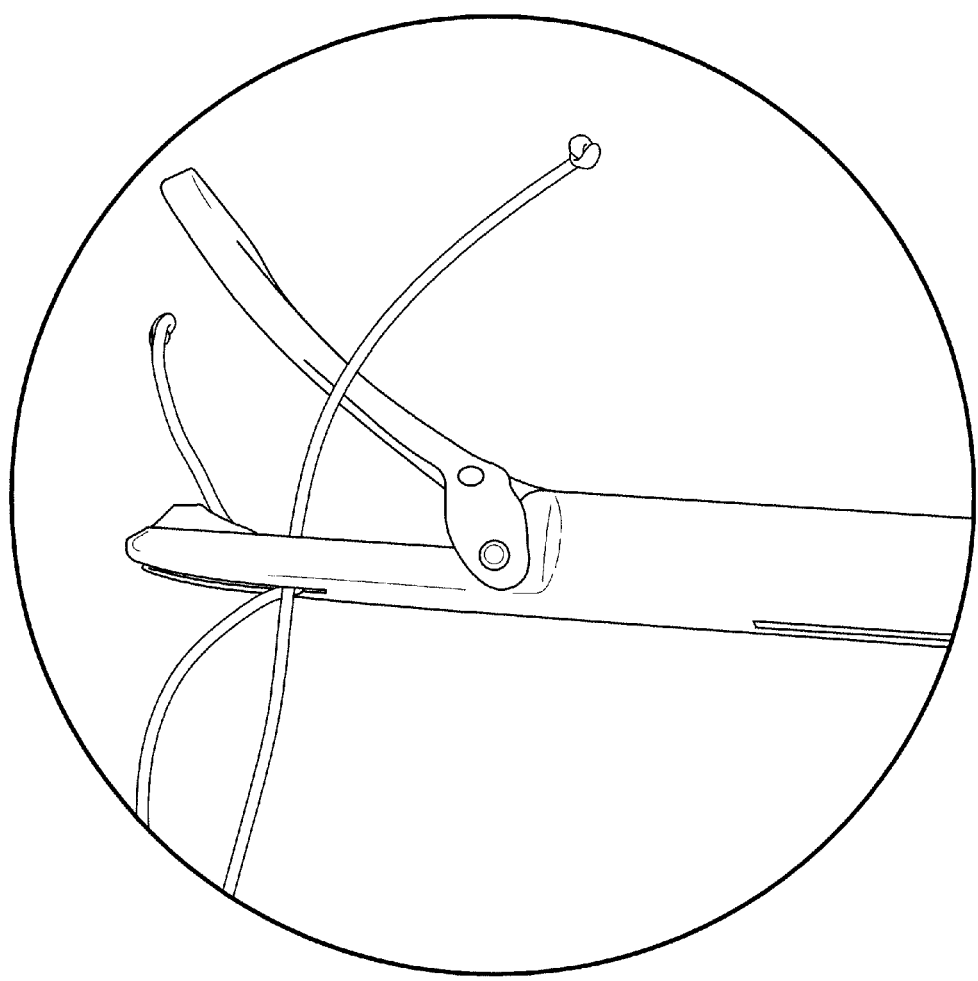
FIGS. 14A-14J illustrate one method of passing a suture having knotted ends as described herein.
Figure 14B:
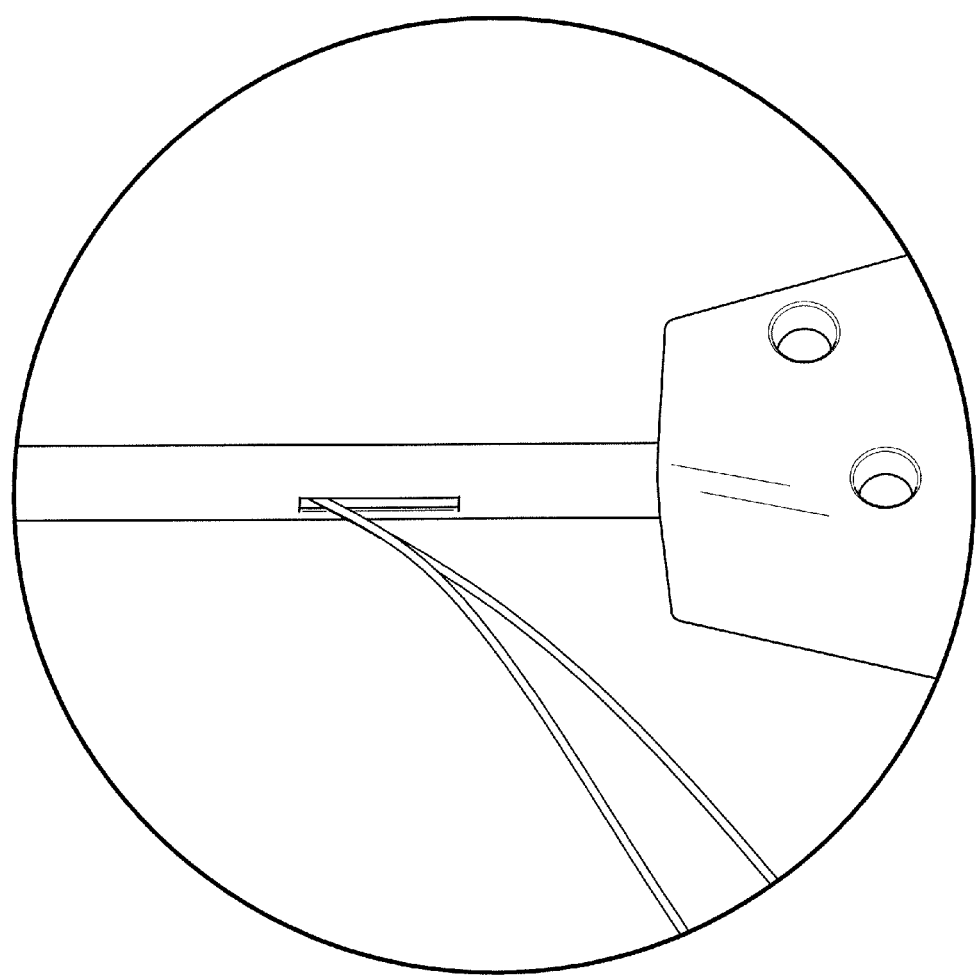

For example, in FIG. 14A an elongate line of suture is knotted at both ends, and these ends are loaded into the suture passer. In this example, the suture passer is similar to the variation shown above (e.g., in FIGS. 7A-7C), and the suture knots are pre-loaded into the lower law member, which is adapted to hold them. In some variations the entire line of suture is pre-loaded into the lower jaw. The tissue penetrator may include a suture retainer comprising a hooked region into which the narrower region of the suture (behind the knot at the end of the suture) may fit. The hook region may be smaller than the diameter of the knot. Thus, the suture end may be held securely in the hook region while passing the suture end through the tissue, and it may be uncoupled from the tissue penetrator when it is withdrawn in the opposite direction.

As mentioned above, in this example, the suture may be held within the tissue penetrator (e.g., in the body of the device) to protect it as it is being used. For example in FIG. 14B the suture extends through the lower jaw and through the elongate length of the member until it exits near the distal handle. Thus, the suture may be held within the body of the device either completely or partially. The knotted ends may be pulled taught into the lower jaw (FIG. 14C); the knotted ends may be completely pulled into the lower jaw, as shown in FIG. 14D. Once the device is pre-loaded with suture, the lower jaw may be retracted; the suture may be pulled taut proximally so that the distal knots remain in the lower jaw, even as it is retracted axially.

The device may be similar to the device described above, but may be adapted to hold one or (as shown in this example) more (e.g., 2) knots at the ends of the suture length.

Figure 14C:
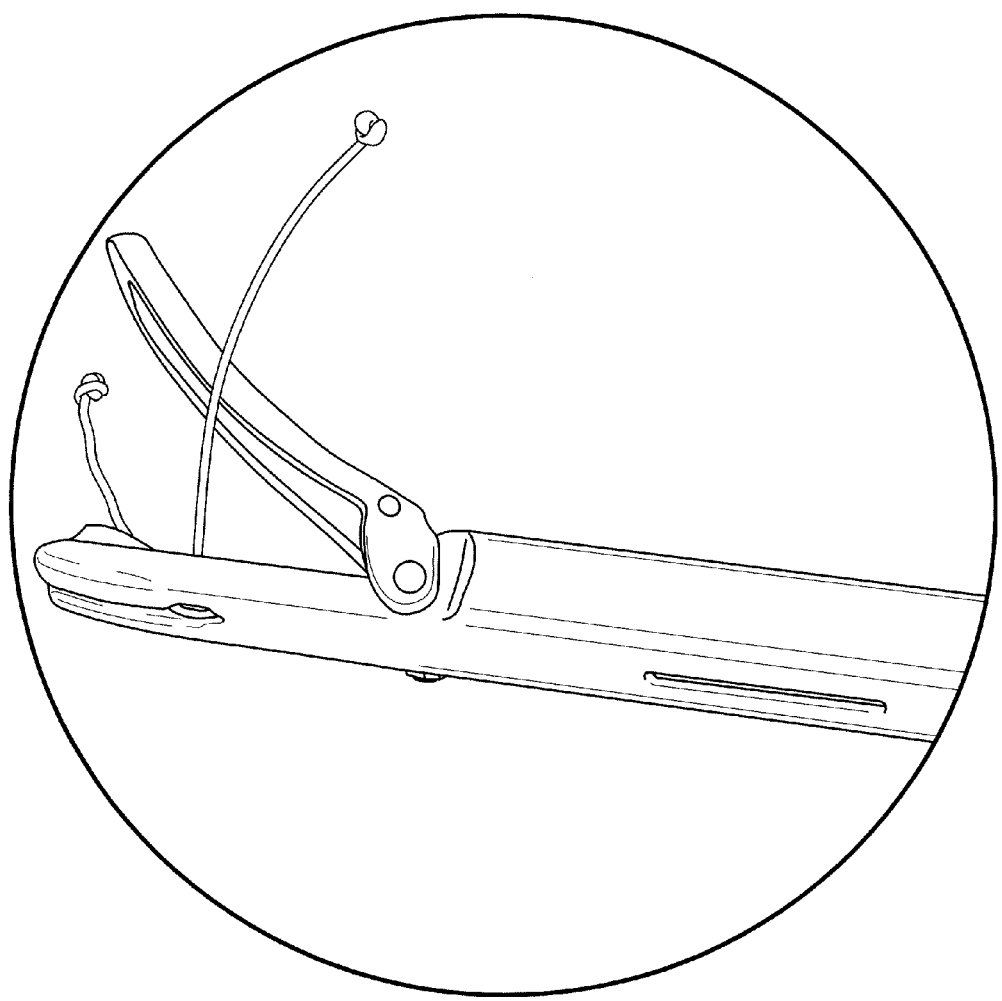
Figure 14D:
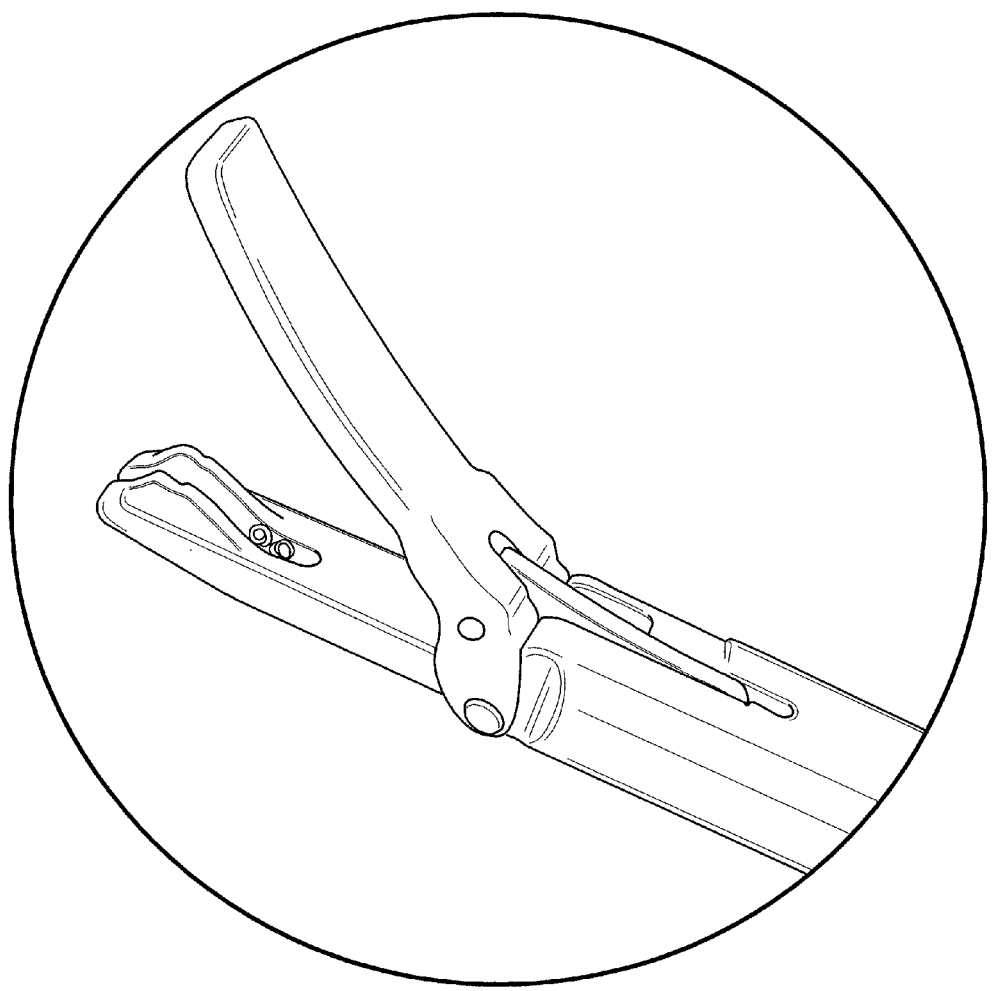
Figure 14E:
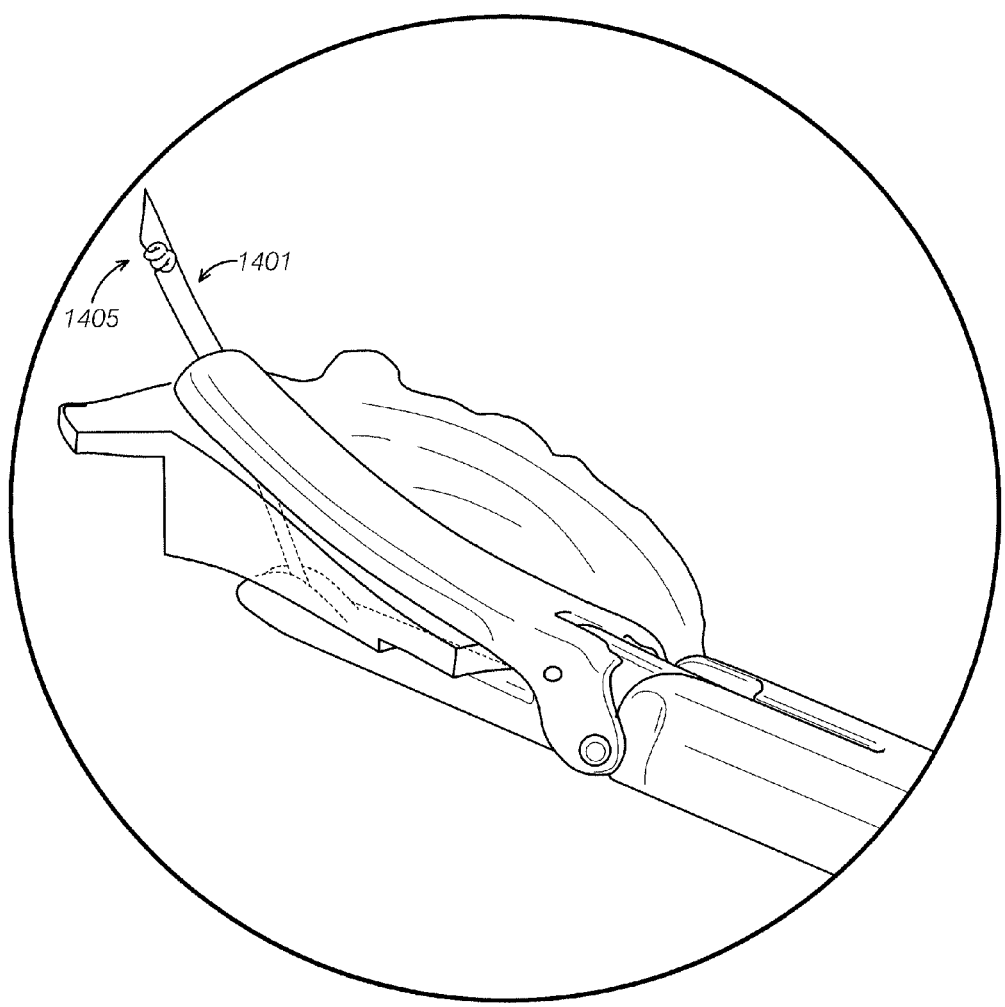

The device may be placed over the tissue as described above (e.g., by adjusting the angle of the upper jaw, and extending/retracting the lower jaw as necessary to surround the tissue to be sutured in the distal-facing opening, as shown in FIG. 14E. In this example, the tissue penetrator extends from the lower jaw, carrying a first knotted end of the suture through the tissue and up into the upper jaw and distally out of the upper jaw. The suture is held in the tissue penetrator 1401 and the knot 1405 prevents it from pulling out, as illustrated in FIG. 14E. Thus, the tissue penetrator picks up on the knot and drags the suture line (and knot) through the tissue and up into and through the upper jaw. In some variations the knot and suture may be held in the upper jaw and the tissue penetrator may extend up and pull the knot down to the lower jaw, instead.

Figure 14F:
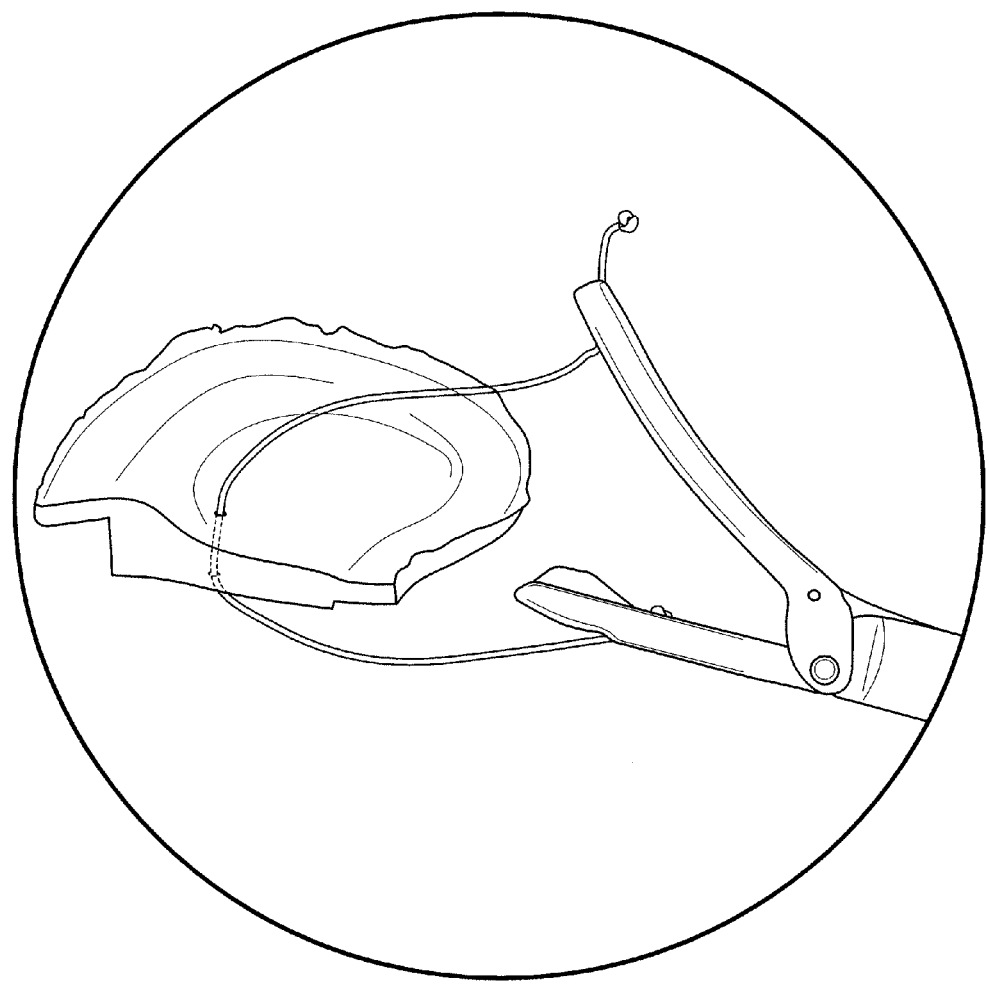
Figure 14G:
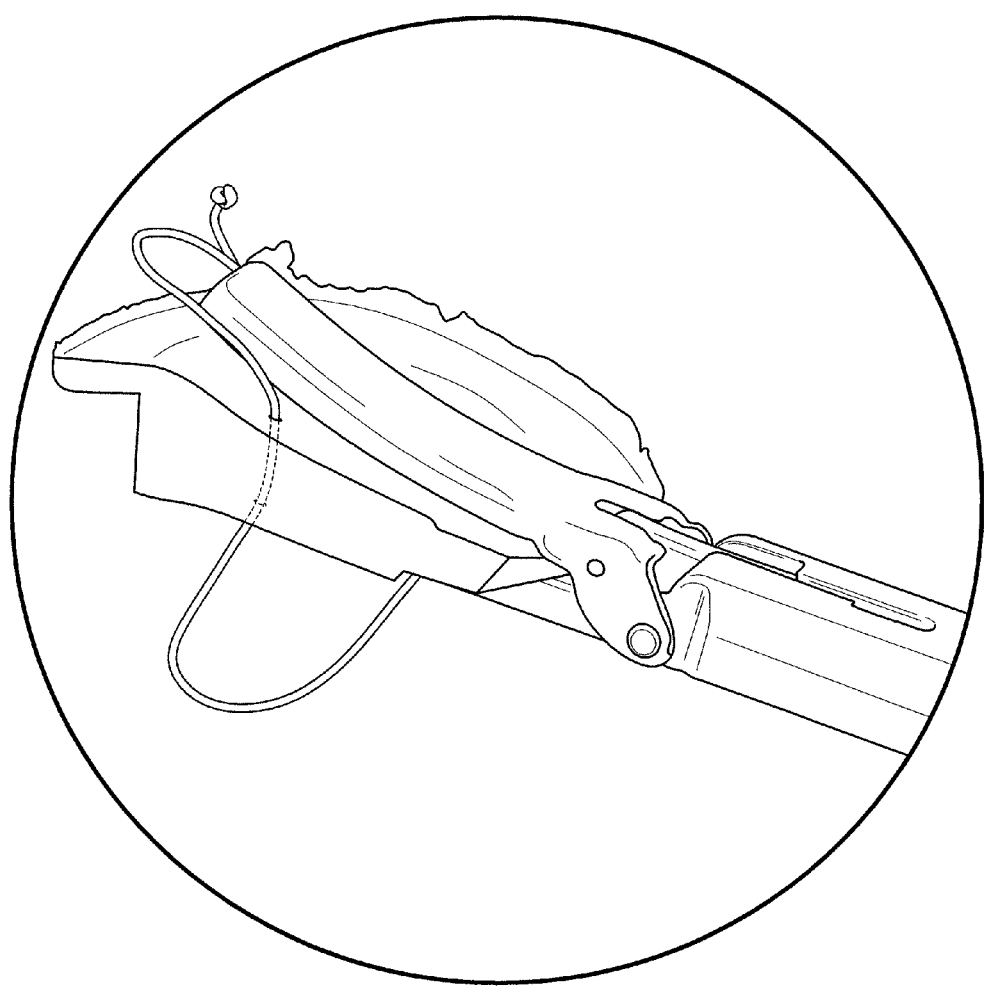

After passing the knot to the upper jaw, the knot may be retained by a strip mechanism in the upper jaw (not visible, but see, e.g., FIG. 9A), and the tissue penetrator retracted. In some variations the retainer in the tissue penetrator (e.g., cut-out region, opening, etc.) is angled so that withdrawing the tissue penetrator readily allows the suture to exit the tissue penetrator, although when driving the suture through the tissue the suture remains seated in the tissue penetrator. In FIG. 14F the device has been withdrawn from the tissue model to illustrate the single pass of the suture after retraction of the tissue penetrator. In practice, the suture passer device may remain on the tissue, although the position may be adjusted, and it does not need to be completely withdrawn from the tissue to reload another suture end. The device may thus be repositioned on the tissue to make the second pass of the suture, without removing the device from the body (or far from the tissue).

The tissue penetrator may be extended again across the tissue to pass the second end of the suture. The second end of the suture may be automatically reloaded into the tissue penetrator. For example, the second end and knot may be held in a holding region of the lower jaw; once the tissue penetrator returns to the lower jaw and the suture retainer in the tissue penetrator is empty, the second suture length (the second end) behind the knot may enter the suture retainer.

Figure 14H:
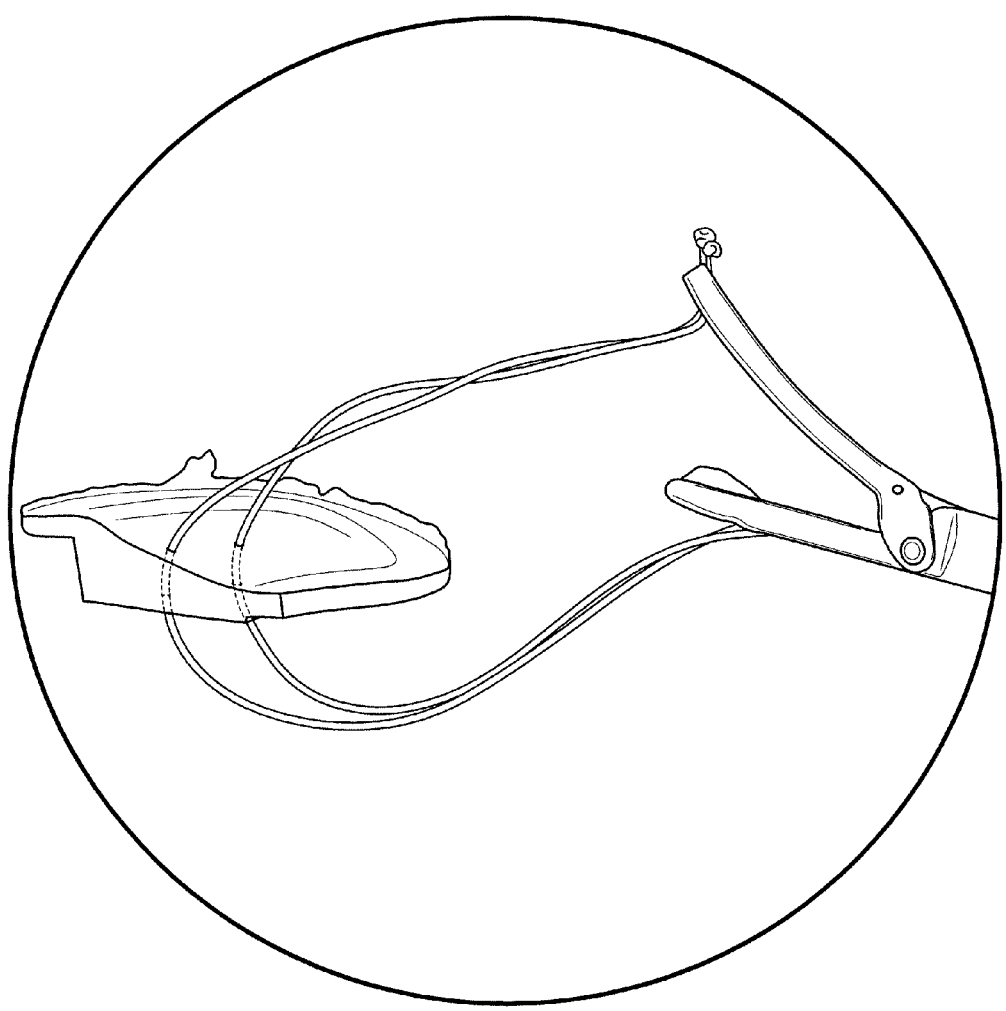
Figure 14I:
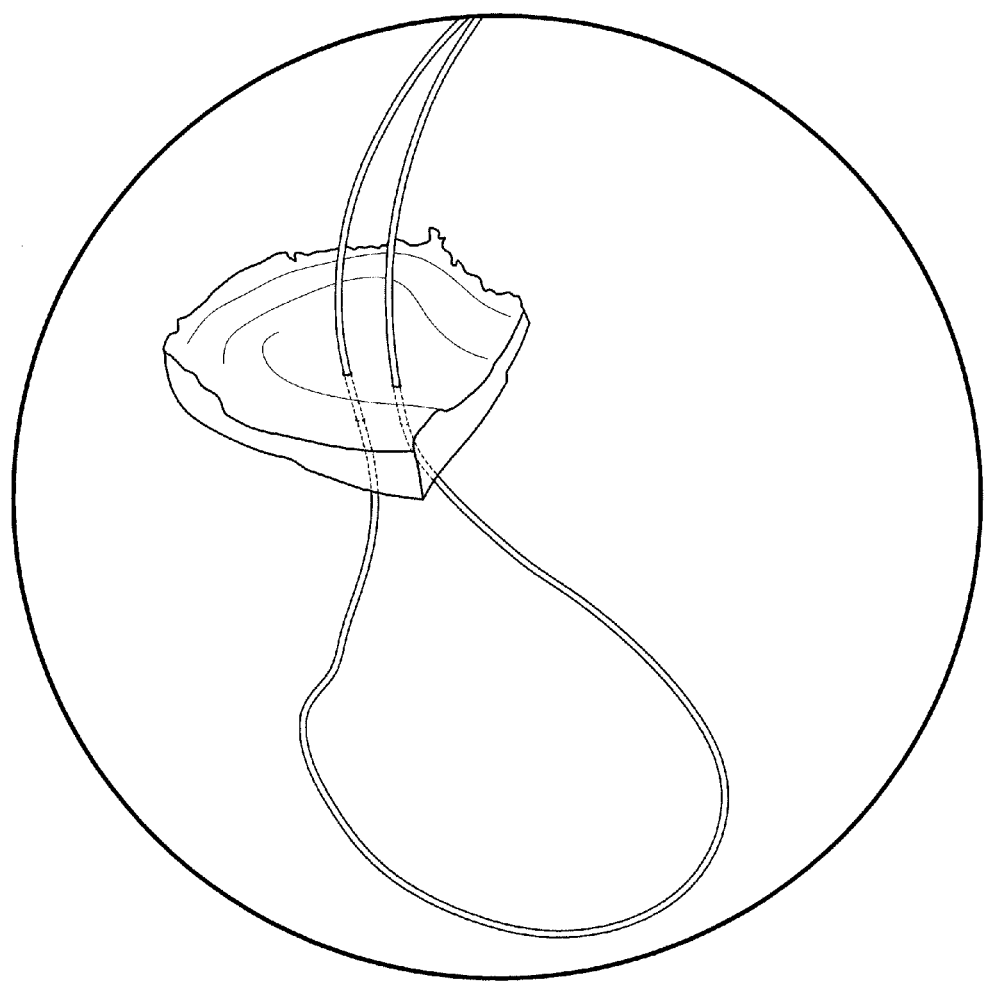
Figure 14J:
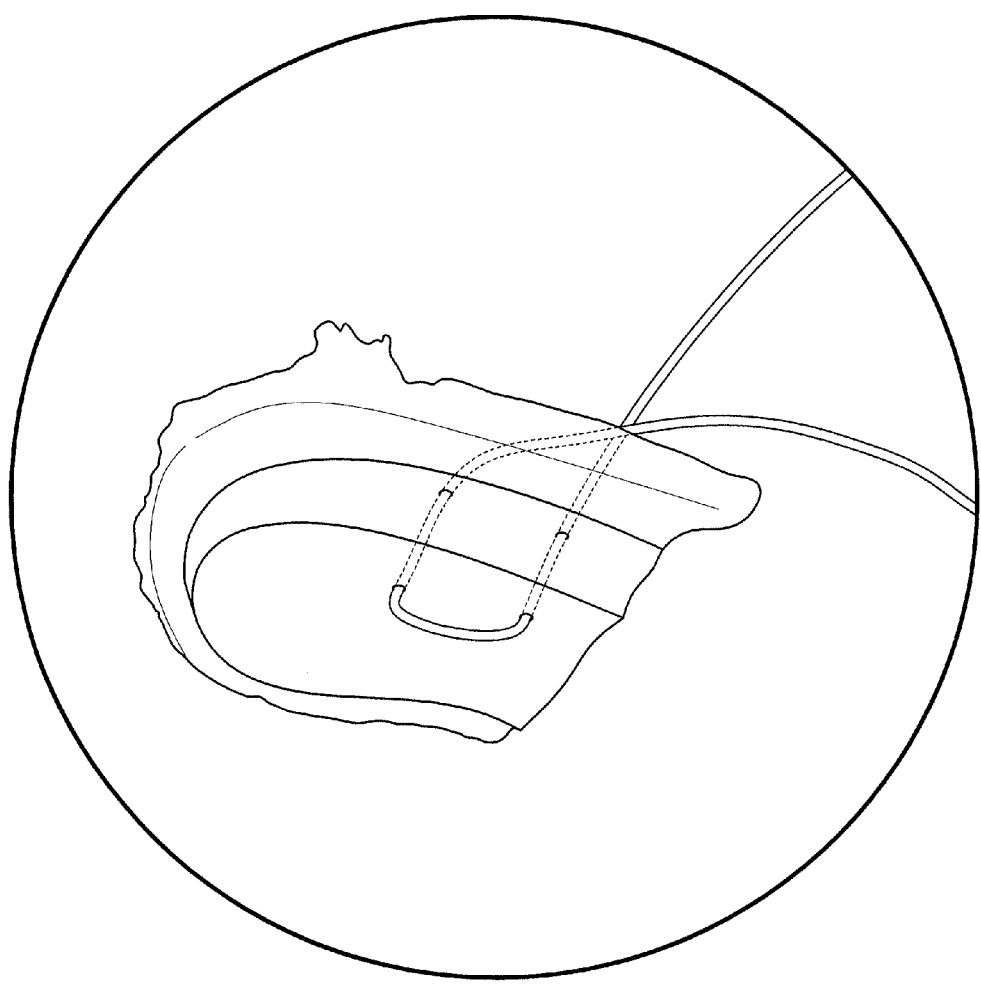

In FIG. 14C, the second end of the suture is passed through the model tissue by again advancing the tissue penetrator. The second knot is passed from the lower jaw member, through the tissue, and up and into the upper jaw. Because the suture is knotted it is held securely by the upper jaw (e.g., the strip mechanism in the upper jaw). Knots are not able to come back through the upper jaw strip mechanism. Once both ends (or lengths) of the suture have been passed, the suture passer device may be removed from the tissue as shown in FIG. 14H. In FIG. 14H the device has been removed without retracting the lower jaw, however in general, the lower jaw may be retracted and the upper jaw bent as necessary to remove the device from within a narrow region of tissue (e.g., the knee). The suture will be left behind in the tissue and the preloaded suture may be pulled from the lower jaw to allow the device to be retracted fully, leaving the loop of suture passed through the tissue, as shown in FIG. 14I. This loop may be pulled taught, as shown in FIG. 14J. Finally, the ends of the suture removed from the tissue penetrator and the loop knotted or tied.

In some variations the ends of the suture (knots) are cut from the suture passer. In some variation, a release mechanism may release the knots from the mechanism (e.g., strip mechanism) in the upper jaw holding them. For example, a release on the handle may remove tension from the strip mechanism, allowing the knots to be released from the upper jaw. In some variations at least one of the knots may be a pre-tied knot as described above, or an additional pre-tied knot may be located proximally to one of the end knots. Thus, a pre-tied knot may be used to tie the two ends together to secure the loop within the tissue.

In general, a device that passes a knot through the tissue may be referred to as a knot capture device, since it is configured to capture and pass knots that are tied to a length of suture (particular near the end or ends of the suture length).

Although the description above is broken into parts and includes specific examples of variations of suture passers, any of the features or elements described in any particular example or section may be incorporated into any of the other embodiments. Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of percutaneously tying a loop of suture around a meniscus tissue using a pre-tied knot, wherein the suture has a proximal end, a distal end, and a pretied knot body formed between the proximal and distal ends, wherein the pre-tied knot body is tied around a leader snare so that a loop of the leader snare extends from the pre-tied knot body in a first direction and a tail of the leader snare extends from the pre-tied knot body in a second direction, the method comprising:
   percutaneously passing the distal end of the suture through the meniscus tissue;
   percutaneously passing the leader snare through the meniscus tissue;
   passing the distal end of the suture through the loop of the leader snare;
   forming a loop of suture by pulling the tail of the leader snare to draw the suture through the pre-tied knot body while removing the leader snare from the pre-tied knot body;
   and
   cinching the loop of suture around the meniscus tissue;
   wherein percutaneously passing the distal end of the suture comprises percutaneously passing the distal end of the suture from the inferior to the superior side of a meniscus or from the superior to the inferior side of the meniscus.

2. The method of claim 1, wherein percutaneously passing the distal end of the suture comprises using a suture passer to pass the distal end of the suture.

3. The method of claim 2, wherein percutaneously passing the leader snare comprises using the suture passer to pass the leader snare.

4. The method of claim 1, wherein percutaneously passing the leader snare comprises percutaneously passing the loop of the leader snare through the meniscus tissue.

5. The method of claim 1, wherein cinching comprises pulling the distal end of the suture.

6. The method of claim 1, wherein cinching comprises tightening the pre-tied knot body over the suture.

7. The method of claim 1, wherein the pre-tied knot body is formed from the suture.

8. A method of percutaneously forming a loop of suture around a tear in a meniscus using a pre-tied knot, wherein the suture has a proximal end, a distal end, and a pre-tied knot body formed between the proximal and distal ends, wherein the pre-tied knot body is tied around a leader snare so that a loop of the leader snare extends from the pre-tied knot body in a first direction and a tail of the leader snare extends from the pre-tied knot body in a second direction, the method comprising:
   percutaneously passing the distal end of the suture from an inferior surface to a superior surface of the meniscus;
   percutaneously passing the leader snare from the inferior surface to the superior surface of the meniscus;
   passing the distal end of the suture through the loop of the leader snare;
   forming a loop of suture by pulling the tail of the leader snare to draw the distal end of the suture from the superior surface to the inferior surface and through the pre-tied knot body while removing the leader snare from the pre-tied knot body; and
   cinching the loop of suture around the meniscus.

9. A method of knotting a suture, the method comprising:
   passing a suture through a meniscus tissue, wherein the suture comprises a pre-tied knot at a first end region of the suture, the pre-tied knot comprising a knot body having one or more loops of the suture around a leader snare, wherein each loop has at least one crossing point, and further wherein the leader snare comprises a bight region formed of a length of linear and flexible material extending from a first end of the knot body and a pull tail extending from a second end of the knot body;
   passing the bight region of the leader snare through the meniscus tissue;
   passing a second end of the suture through the bight region;
   pulling the pull tail of the leader snare to draw the second end of the suture through the knot body while removing the leader snare from the knot body;
   and
   tightening the knot body around the second end of the suture, wherein passing the suture comprises passing the suture from the inferior to the superior side of a meniscus or from the superior to the inferior side of the meniscus.

10. The method of claim 9, wherein passing the suture through the meniscus tissue further comprises passing the knot body through the tissue.

11. The method of claim 9, further comprises sliding the knot body along the suture.

12. The method of claim 9, wherein tightening the knot body comprises pulling the first and second ends of the suture.

13. The method of claim 9, further comprising cutting the suture to remove free ends of the suture from a subject's body.

14. The method of claim 9, wherein passing the suture through the meniscus tissue comprises endoscopically passing the suture using a suture passer.

15. The method of claim 9, wherein passing the suture comprises passing the suture through the meniscus.

16. The method of claim 9, wherein passing the suture comprises passing the second end of the suture through a first region of the meniscus tissue and passing the first end of the suture and the knot body through a second region of the meniscus tissue.

17. The method of claim 9, wherein the bight region of the leader snare extends from the knot body in the direction of the second end of the suture and the pull tail of the leader snare extends from the knot body in the direction of the first end of the suture.

* * * * *